United States Patent
Cao

(10) Patent No.: US 10,968,474 B2
(45) Date of Patent: Apr. 6, 2021

(54) DEVICES FOR DETECTING TARGET BIOLOGICAL MOLECULES FROM CELLS AND VIRUSES

(71) Applicant: University of Florida Research Foundation, Inc., Gainesville, FL (US)

(72) Inventor: Yunwei Charles Cao, Gainesville, FL (US)

(73) Assignee: University of Florida Research Foundation Inc., Gainesville, FL (US)

( * ) Notice: Subject to any disclaimer, the term of this patent is extended or adjusted under 35 U.S.C. 154(b) by 40 days.

(21) Appl. No.: 16/366,731

(22) Filed: Mar. 27, 2019

(65) Prior Publication Data

US 2019/0323069 A1    Oct. 24, 2019

Related U.S. Application Data

(62) Division of application No. 15/355,306, filed on Nov. 18, 2016, now Pat. No. 10,301,667.

(60) Provisional application No. 62/256,747, filed on Nov. 18, 2015.

(51) Int. Cl.
| | |
|---|---|
| *C12Q 1/6816* | (2018.01) |
| *B01L 3/00* | (2006.01) |
| *G01N 33/543* | (2006.01) |
| *G01N 33/58* | (2006.01) |
| *B01L 7/00* | (2006.01) |
| *G01N 35/10* | (2006.01) |

(52) U.S. Cl.
CPC ...... *C12Q 1/6816* (2013.01); *B01L 3/502761* (2013.01); *G01N 33/54313* (2013.01); *G01N 33/587* (2013.01); *B01L 7/00* (2013.01); *B01L 2200/0631* (2013.01); *B01L 2200/0636* (2013.01); *B01L 2200/0647* (2013.01); *B01L 2200/10* (2013.01); *B01L 2300/087* (2013.01); *B01L 2300/0867* (2013.01); *B01L 2400/0424* (2013.01); *B01L 2400/0487* (2013.01); *G01N 35/1097* (2013.01)

(58) Field of Classification Search
CPC .......... G01N 33/587; G01N 33/54313; G01N 35/1097; B01L 3/502761; B01L 2200/0647; B01L 2200/10; B01L 2200/0631; B01L 2300/0867; C12Q 1/6816
See application file for complete search history.

(56) References Cited

U.S. PATENT DOCUMENTS

| | | | |
|---|---|---|---|
| 2003/0211488 A1* | 11/2003 | Mirkin | C12Q 1/6816 435/6.12 |
| 2004/0175842 A1 | 9/2004 | Roitman | |
| 2004/0209354 A1 | 10/2004 | Mathies | |
| 2006/0234248 A1 | 10/2006 | Sun | |

(Continued)

*Primary Examiner* — Joseph G. Dauner
(74) *Attorney, Agent, or Firm* — Thomas Horstemeyer, LLP

(57) ABSTRACT

Described herein are fluid-manipulation-based devices and methods of use. Fluid manipulations according to devices and methods as described herein can be configured to perform assays on biological samples. Devices and methods as described herein can manipulate and analyze nanoliter volumes of fluid, microliter volumes of fluid, milliliter volumes of fluid, or greater. Embodiments of the present disclosure can enable random biological assays and rapid, simultaneous analysis of multiple biological samples.

7 Claims, 34 Drawing Sheets

Specification includes a Sequence Listing.

(56) References Cited

U.S. PATENT DOCUMENTS

2008/0160634 A1    7/2008   Su
2009/0148933 A1    6/2009   Battrell

* cited by examiner

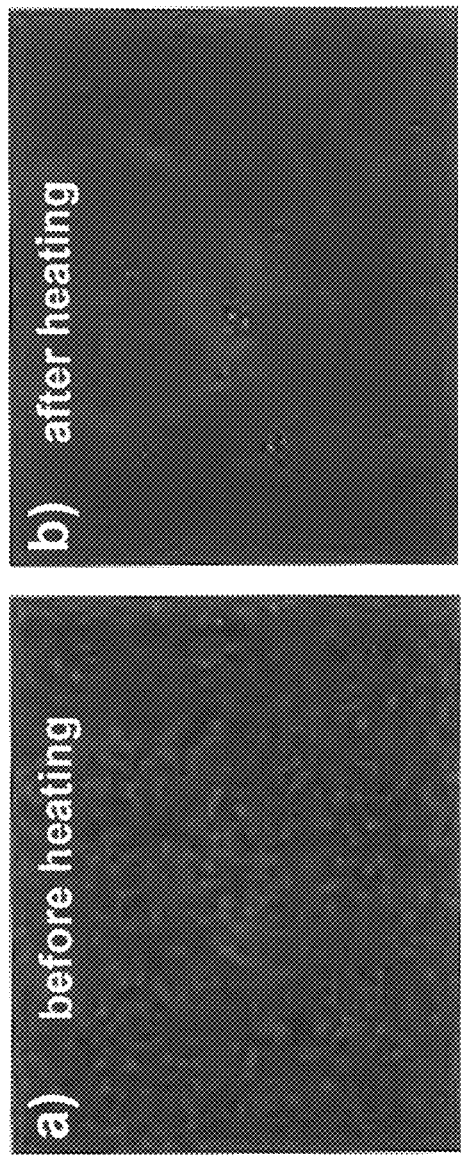

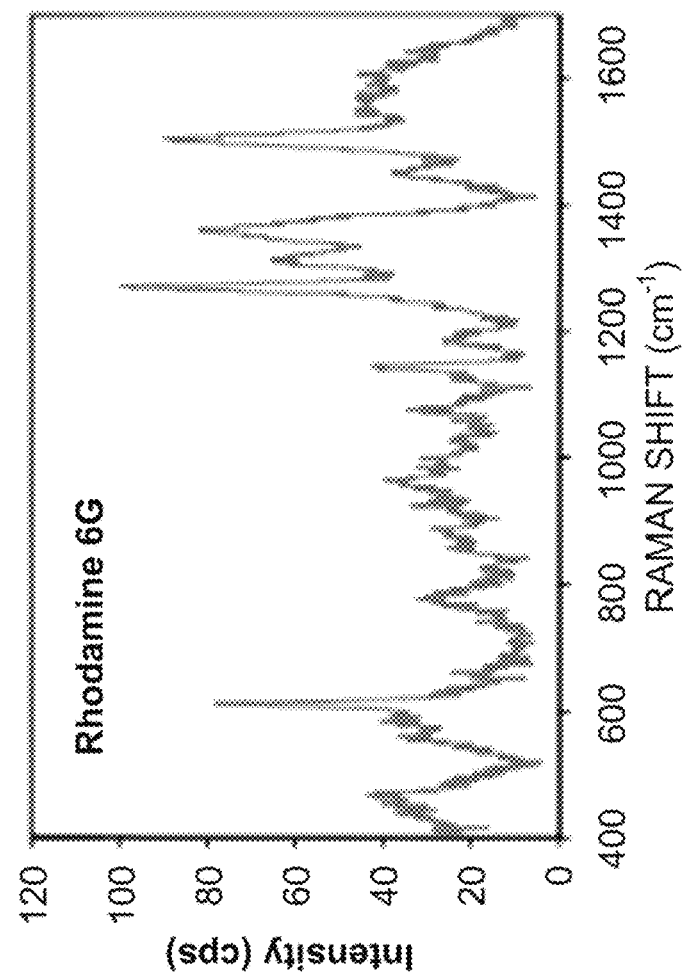
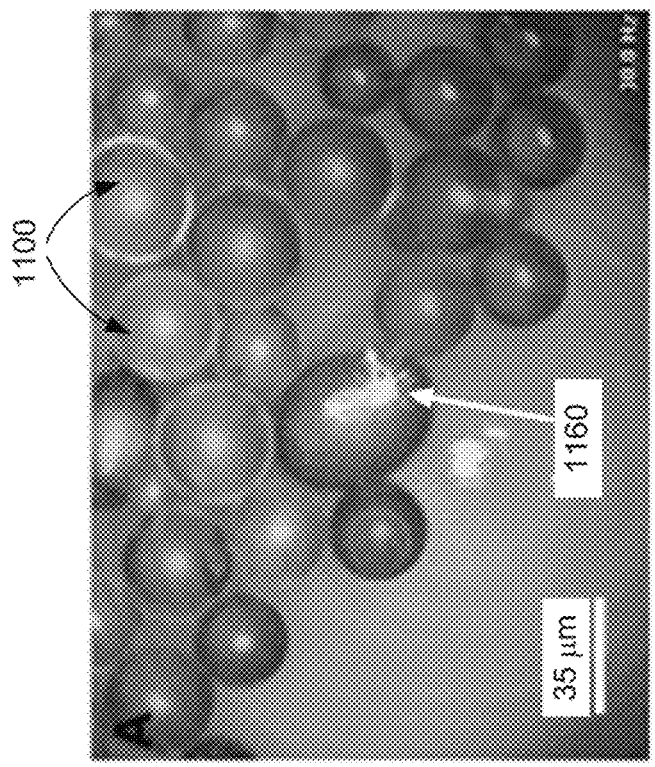
Fig. 11B
Fig. 11A

SEQUENCE LISTING

```
<160> NUMBER OF SEQ ID NOS: 14

<210> SEQ ID NO 1
<211> LENGTH: 42
<212> TYPE: DNA
<213> ORGANISM: Artificial Sequence
<220> FEATURE:
<223> OTHER INFORMATION: 44-mer double strand DNA positive control
      target

<400> SEQUENCE: 1
gtgagagtag gatcatatac cgttagatgc tgctggcgtt at                          42

<210> SEQ ID NO 2
<211> LENGTH: 43
<212> TYPE: DNA
<213> ORGANISM: Artificial Sequence
<220> FEATURE:
<223> OTHER INFORMATION: negative control DNA

<400> SEQUENCE: 2
gtcactctag gatcatatac cgttacttcg acgtggcgat atg                         43

<210> SEQ ID NO 3
<211> LENGTH: 36
<212> TYPE: DNA
<213> ORGANISM: Artificial Sequence
<220> FEATURE:
<223> OTHER INFORMATION: BA-Target

<400> SEQUENCE: 3
acagagggat tattgttaaa tattgataag gatata                                 36

<210> SEQ ID NO 4
<211> LENGTH: 18
<212> TYPE: DNA
<213> ORGANISM: Artificial Sequence
<220> FEATURE:
<223> OTHER INFORMATION: BA-Probe-Strand

<400> SEQUENCE: 4
taacaataat ccctctgt                                                     18

<210> SEQ ID NO 5
<211> LENGTH: 18
<212> TYPE: DNA
<213> ORGANISM: Artificial Sequence
<220> FEATURE:
<223> OTHER INFORMATION: BA-Capture Strand

<400> SEQUENCE: 5
tatatcctta tcaatatt                                                     18

<210> SEQ ID NO 6
<211> LENGTH: 36
```

```
<212> TYPE: DNA
<213> ORGANISM: Artificial Sequence
<220> FEATURE:
<223> OTHER INFORMATION: VEE-Target

<400> SEQUENCE: 6
tgacaagacg ttcccaatca tgttggaagg gaagat                             36

<210> SEQ ID NO 7
<211> LENGTH: 18
<212> TYPE: DNA
<213> ORGANISM: Artificial Sequence
<220> FEATURE:
<223> OTHER INFORMATION: VEE-Probe Strand

<400> SEQUENCE: 7
attgggaacg tcttgtca                                                 18

<210> SEQ ID NO 8
<211> LENGTH: 18
<212> TYPE: DNA
<213> ORGANISM: Artificial Sequence
<220> FEATURE:
<223> OTHER INFORMATION: VEE-Capture Strand

<400> SEQUENCE: 8
atcttccctt ccaacatg                                                 18

<210> SEQ ID NO 9
<211> LENGTH: 39
<212> TYPE: DNA
<213> ORGANISM: Artificial Sequence
<220> FEATURE:
<223> OTHER INFORMATION: YP-Target

<400> SEQUENCE: 9
agagtaggat catataccccg ttagatgctg ctggcgtta                         39

<210> SEQ ID NO 10
<211> LENGTH: 21
<212> TYPE: DNA
<213> ORGANISM: Artificial Sequence
<220> FEATURE:
<223> OTHER INFORMATION: YP-Capture Strand

<400> SEQUENCE: 10
taacgccagc agcatctaac g                                             21

<210> SEQ ID NO 11
<211> LENGTH: 18
<212> TYPE: DNA
<213> ORGANISM: Artificial Sequence
<220> FEATURE:
<223> OTHER INFORMATION: YP-Probe Strand

<400> SEQUENCE: 11
ggtatatgat cctactct                                                 18

<210> SEQ ID NO 12
<211> LENGTH: 30
<212> TYPE: DNA
<213> ORGANISM: Artificial Sequence
<220> FEATURE:
<223> OTHER INFORMATION: example target strand sequence

<400> SEQUENCE: 12
```

```
taggaatagt tataaattgt tattagggag                                              30

<210> SEQ ID NO 13
<211> LENGTH: 15
<212> TYPE: DNA
<213> ORGANISM: Artificial Sequence
<220> FEATURE:
<223> OTHER INFORMATION: example capture strand sequence

<400> SEQUENCE: 13
atccttatca atatt                                                              15

<210> SEQ ID NO 14
<211> LENGTH: 16
<212> TYPE: DNA
<213> ORGANISM: Artificial Sequence
<220> FEATURE:
<223> OTHER INFORMATION: example probe strand

<400> SEQUENCE: 14
taacaataat ccctca                                                             16
```

DEVICES FOR DETECTING TARGET BIOLOGICAL MOLECULES FROM CELLS AND VIRUSES

CROSS-REFERENCE TO RELATED APPLICATIONS

This application is a Divisional Application of U.S. application Ser. No. 15/355,306, having the title "DEVICES FOR DETECTING TARGET BIOLOGICAL MOLECULES FROM CELLS AND VIRUSES", filed Nov. 18, 2016, which application claims the benefit of and priority to U.S. Provisional Application Ser. No. 62/256,747, having the title "DEVICES FOR DETECTING TARGET BIOLOGICAL MOLECULES FROM CELLS AND VIRUSES," filed on Nov. 18, 2015, the disclosures of both of which are incorporated herein in by reference in their entireties.

GOVERNMENT SUPPORT

This invention was made with government support under Contract No. W911SR-12-C-0054 awarded by the US Army Edgewood Chemical and Biological Center (ECBC). The government has certain rights in the invention.

SEQUENCE LISTING

This application contains a sequence listing filed in electronic form as an ASCII.txt file entitled UF#-16041 (22109-1261) 222109_1260_patentin_ST25_2.txt, created on Jul. 27, 2018. The content of the sequence listing is incorporated herein in its entirety.

BACKGROUND

Stationary nucleic acid strands have previously been analyzed on a fixed substrate, such as a fixed glass slide conventional micro array. Some instruments that have been used to analyze nucleic acid include Caliper Life Sciences-Perkin Elmer Sciclone NGSx, Zephyr NGS Workstation, and JANUS NGS Express, LabChip GX and LabChip DS, and LabChip XT; Illumina HiScan and iScan; Nanosphere Verigene System; and Applied Biosystems Ion PGM, 3500 Series Genetic Analyzers, and Ion Torrent Sequencing System.

Disadvantages of existing instruments such as those listed above for analyzing biological agents include: (1) lack of: integrated sample purification, biomolecule isolation, biomolecule detection, and lack of sensitivity; (2) long detection times; and (3) high cost of ownership. Additionally, these laboratory instruments are large in size and are not able to be down-scaled to handheld or other portable use in the field. Accordingly, there is a need to address the aforementioned deficiencies and inadequacies.

SUMMARY

Described herein are devices for manipulating fluids, which can comprise: an assay mixing module configured to mix isolated biological targets with a plurality of microbead complex components contained in one more reagents to generate one or more non-stationary microbead complexes; a flow path in fluidic communication with the assay mixing module and configured to receive the one or more non-stationary microbead complexes; and an analysis region configured to analyze the one or more non-stationary microbead complexes.

In additional embodiments, the plurality of microbead complex components in devices as described herein can further comprise: one or more microbeads with one or more capture molecules coupled thereto; one or more nanoparticles with one or more probe molecules coupled thereto by way of a label; and wherein the capture molecule and probe molecule are configured to bind to one or more isolated biological targets. Embodiments of devices as described herein can additionally comprise: a biological target purification module configured to receive products of cell lysis and isolate biological targets, wherein the biological target purification module comprises one or more reagent vessels; and wherein the biological target purification module is in fluidic communication with the assay mixing module and configured to send isolated biological targets to the assay mixing module.

A sample lysis module configured to receive one or more biological samples can also be present in devices as described herein, wherein the module is configured to lyse cells and create products of cell lysis, the products of cell lysis comprising biological targets, wherein the sample lysis module is configured to send biological targets to the biological target purification module. Sample lysis modules can be configured for thermal or enzymatic lysis.

Further embodiments of devices as described herein can further comprise a sample isolation module containing one or more micro-scale filters configured to isolate biological samples of a desired size, wherein the sample isolation module is in fluidic communication with the cell lysis module, wherein the sample isolation module is configured to receive samples containing biological samples from outside of the device and configured send biological samples of a desired size to the cell lysis module. More than one of any of the above modules can be integrated into a single device or system.

Devices as described herein can comprise one or more valves operatively coupled to a controller, a computing device, or both, wherein the one or more valves are configured to direct or restrict flow between the modules of the device, vessels within a module, or both.

Devices as described herein can comprise one or more pumps operationally coupled to the device and configured to provide positive fluid pressure, negative fluid pressure, or both in the device. One or more pumps as described herein can be operatively coupled to a controller, a computing device, or both. One or more pumps as described herein can be syringe pumps, dielectrophoresis pumps, solid chemical propellant pumps, individually or in combination.

Fluids of devices as described herein can be femtofluids, picofluids, nanofluids, microfluids, or fluids of a greater volume.

Isolated biological targets as described herein can be nucleic acids.

Labels as described herein can be a spectroscopic dye.

One or more non-stationary microbead complexes as described herein can have a maximum dimension of a size to fit within a focal point or diameter of the cross-sectional area of a laser beam configured to analyze the bead complex.

Microbeads as described herein can be at least two orders of magnitude larger than the one or more nanoparticles.

One or more microbeads and one or more nanoparticles as described herein can be within respective separate solutions or are contained within a common solution.

Devices as described herein can further comprise: at least two microbeads having at least two different respective capture molecules coupled thereto; and at least two nanoparticles having at least two different respective probe molecules coupled thereto via different respective labels, the different respective capture molecules and different respective probe molecules configured to be, respectively, coupled together via different respective biological targets to form a random array of at least two non-statoinary microbead complexes in random locations in a fluid.

Labels as described herein can be configured to provide a Raman spectrum to a portable Raman spectrometer.

Capture molecules as described herein can be one or more DNA or RNA molecules configured to bind to a biological target of a biowarfare agent.

One of the one or more capture molecules and one or more probe molecules as described herein can be an aptamer, antibody, or nucleic acid.

One or more microbeads as described herein can have multiple capture molecules coupled thereto, wherein the multiple capture molecules are the same or different.

Nanoparticles as described herein can be a gold nanoparticle and can have one or more silver nanoparticles attached thereto.

Described herein are methods of detecting a biological target. Embodiments of methods as described herein can comprise: providing one or more isolated biological targets; forming one or more non-stationary microbead complexes from the one or more isolated biological targets and a plurality of microbead complex components in a volume of fluid; and detecting the one or more non-stationary microbead complexes with an analysis platform.

One or more non-stationary microbead complexes used in methods as described herein can comprise: one or more microbeads with one or more capture molecules coupled thereto; one or more nanoparticles with one or more probe molecules coupled thereto by way of a label; and wherein the capture molecule and probe molecule are configured to bind to one or more isolated biological targets.

Methods as described herein can utilized a volume of fluid being a femtoliter volume, a picoliter volume, a nanoliter volume, or microliter volume.

Methods as described herein can isolate one or more isolated biological targets from products of cell lysis.

Methods as described herein can lyse one or more biological cells to generate products of cell lysis, the products of cell lysis comprising one or more biological targets.

Methods as described herein can process (e.g. separate components thereof by size, for example) a biological sample containing one or more biological cells to isolate the one or more biological cells.

BRIEF DESCRIPTION OF THE DRAWINGS

The foregoing will be apparent from the following more particular description of example embodiments of the present disclosure, as illustrated in the accompanying drawings in which like reference characters refer to the same parts throughout the different views. The drawings are not necessarily to scale, emphasis instead being placed upon illustrating embodiments of the present disclosure.

FIG. 1B shows an example target sequence (SEQ ID No. 12), an example capture strand (SEQ ID No. 13), and an example probe strand (SEQ ID No. 14).

FIG. 3A is a micrograph illustration of a *Bacillus anthracis* (BA) spore solution before heating.

FIG. 3B is a micrograph illustration of the spore solution of FIG. 3A after heating.

FIG. 11A is a micrograph of a 30 µm diameter glass microbead sample showing a position of a 5 µm diameter laser beam for measurement of SERS spectrum.

FIG. 11B is a graph showing and a SERS spectrum obtained from the glass microbeads sample of FIG. 11A. The glass microbeads sample included oligonucleotide functionalized microbeads containing a dye Rhodamine 6G (R6G) (known in the art of spectroscopy) as the probe dye.

DETAILED DESCRIPTION

Figure 1A:
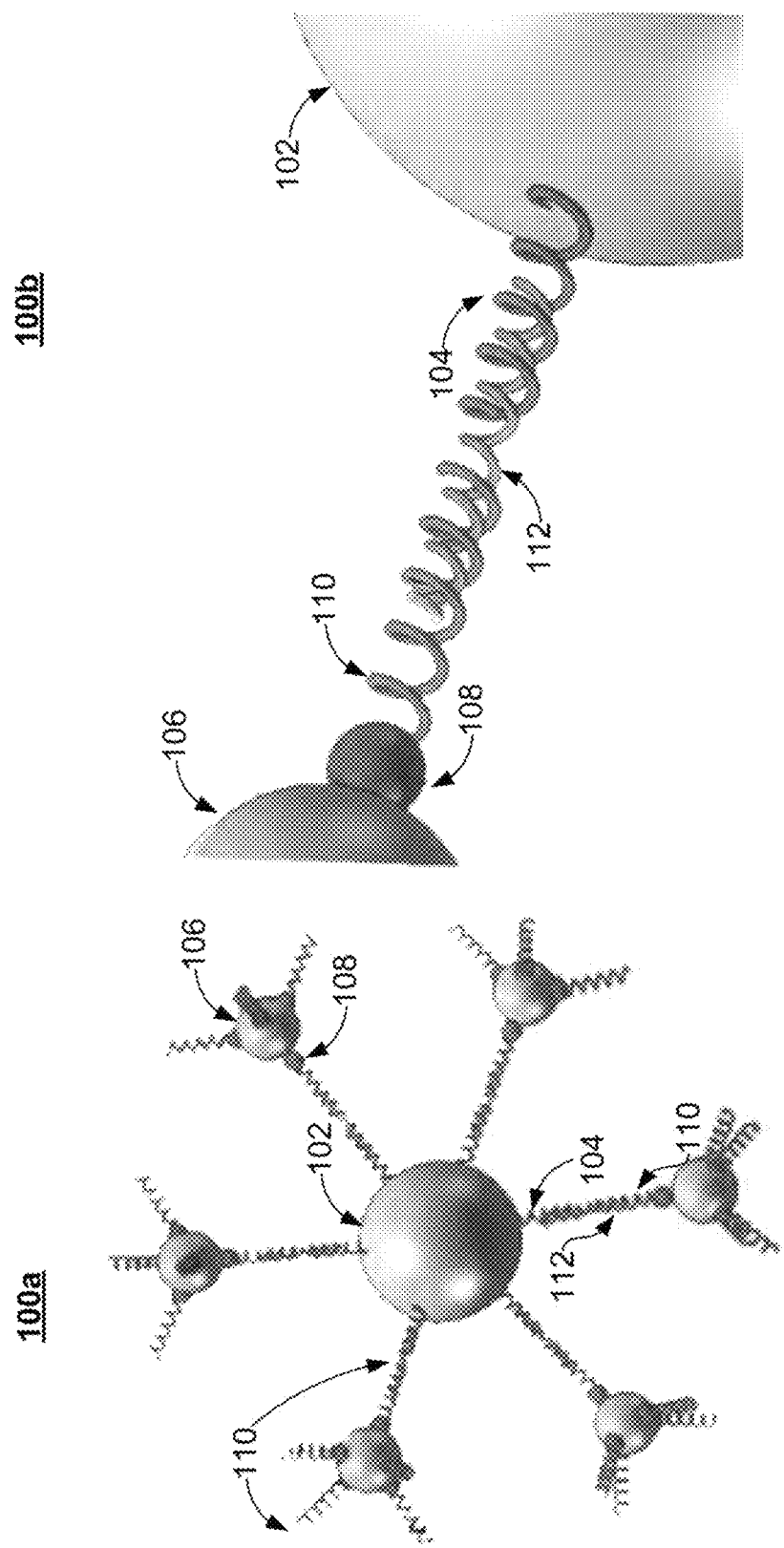
FIGS. 1A and 1B illustrate an embodiment biological molecule bead complex based on a microbead substrate for surface-enhanced Raman spectroscopy (SERS) DNA random array assay analysis methods.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of organic chemistry, inorganic chemistry, Raman spectroscopy, protein isolation, nucleic acid isolation, antibody isolation, hybridization, microfluidics, spectroscopy, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Description and Definitions

Unless defined otherwise, all technical and scientific terms used herein have the same meaning as commonly understood by one of ordinary skill in the art to which this disclosure pertains. Additional definitions and clarification of terms used herein follows.

Nucleic Acid Molecules

As used herein, the term "target biological molecule" or "biological target molecule" refers to a biological molecule, e.g., a nucleic acid molecule, protein, lipid, carbohydrate, peptide, antibody, or the like, whose presence or absence in a sample (e.g., a biological sample) is desired to be detected.

As used herein, the term "nucleic acid molecule" refers to a polymer comprising nucleotide monomers (e.g., ribonucleotide monomers or deoxyribonucleotide monomers). The term "nucleic acid molecule" can include, for example, genomic DNA, cDNA, ssDNA, dsDNA, RNA, mRNA, tRNA, shRNA, rRNA, snRNA, miRNA, tmRNA, dsRNA and DNA-RNA hybrid molecules. Nucleic acid molecules can be naturally, e.g., occurring, recombinant, or synthetic. Nucleic acid molecules can be single-stranded, double-stranded or triple-stranded. In some embodiments, nucleic acid molecules can be modified. Nucleic acid modifications include, for example, methylation, acetylation, substitution of one or more of the naturally occurring nucleotides with a nucleotide analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). If the polymer is a double-stranded, "nucleic acid" can refer to either or both strands of the molecule.

The term "nucleotide" refers to naturally-occurring ribonucleotide or deoxyribonucleotide monomers, as well as their non-naturally-occurring derivatives and analogs. Nucleotides can include, for example, nucleotides comprising naturally-occurring bases (e.g., adenosine, cytidine, thymidine, guanosine, inosine, uridine, deoxyadenosine, deoxythymidine, deoxyguanosine, or deoxycytidine) and nucleotides comprising modified bases (e.g., 2-aminoadenosine, 2-thiothymidine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, 2-thiocytidine).

As used herein, the term "nucleotide base" refers a heterocyclic nitrogenous base of a nucleotide or nucleotide analog (e.g., purine, pyrimidine, 7-deazapurine). Suitable nucleotide bases can include, but are not limited to, adenine, cytosine, thymine, guanine, uracil, hypoxanthine and 7-deaza-guanine. The base pair can be either a conventional (standard) Watson-Crick base pair or a non-conventional (non-standard) non-Watson-Crick base pair, for example, a Hoogstein base pair or bidentate base pair.

The term "sequence," in reference to a nucleic acid molecule, refers to a contiguous series of nucleotides that are joined by covalent linkages, such as phosphorus linkages and/or non-phosphorus linkages (e.g., peptide bonds). A sequence can be read in a 5'->3' direction or a 3'->5' direction.

The term "target sequence" refers to a sequence, e.g., a nucleotide sequence within a target biological molecule that is capable of forming a hydrogen-bonded duplex with a complementary nucleotide sequence (e.g., a substantially complementary sequence on a nucleotide probe). A target sequence can also be an amino acid sequence translated from a nucleic acid sequence.

As used herein, "complementary" refers to sequence complementarity between different nucleic acid strands or between regions of the same nucleic acid strand. One region of a nucleic acid is complementary to another region of the same or a different nucleic acid if, when the regions are arranged in an anti-parallel fashion, at least one nucleotide residue of the first region is capable of base pairing (i.e., hydrogen bonding) with a residue of the second region, thus forming a hydrogen-bonded duplex.

The term "substantially complementary" refers to two nucleic acid strands (e.g., a strand of a target nucleic acid molecule and a complementary single-stranded oligonucleotide probe) that are capable of base pairing with one another to form a stable hydrogen-bonded duplex under stringent hybridization conditions, including the hybridization conditions described herein. In general, "substantially complementary" refers to two nucleic acid strands having at least 70%, for example, about 75%, 80%, 85%, 90%, 95%, 97%, 98%, 99% or 100%, complementarity.

The term "hybrid" molecule refers to a double-stranded nucleic acid molecule formed by hydrogen bonding between complementary nucleotides.

Biological Targets

In certain embodiments, the target biological molecule comprises a nucleotide sequence of an organism or protein, e.g., a pathogenic microorganism, including, but not limited to, a virus (e.g., Adenoviridae, Herpesviridae, Hepadnaviridae, Flaviviridae, Orthomyxoviridae, Paramyxoviridae, Papovaviridae, Picornaviridae, Polyomavirus, Retroviridae, Rhabdoviridae, Togaviridae), a bacterium (e.g., *Bacillus, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptspira, Listeria, Mycobacterium, Mycoplasma, Neisseria, Pseodomonas, Rickettsia, Salmonella, Shigella, Staphylococcus, Steptococcus, Treponema, Vibrio, Yersinia*), a fungus (e.g., *Aspergillus, Candida, Cryptococcus, Histoplasma, Pneumocystis, Stachybotrys*), or a eukaryotic microorganism, such as, for example, a protist (e.g., *Plasmodium*) or a helminth (e.g., *Ascaris*). Examples of pathogens include, among others, Ebola virus, Dengue virus, hantaviruses, Lassa fever virus, Marburg virus, Variola virus, West Nile virus, Venezuelan equine encephalitis virus (VEE), Eastern equine encephalitis virus, Western equine encephalitis virus, Japanese equine encephalitis virus, Yellow fever virus, Rift Valley fever virus, *Bacillus anthracis* (BA), *Staphylococcus aureus, Clostridium botulinum, Brucella abortus, Brucella melitensis, Brucella suis, Vibrio cholera, Corynebacterium diphtheria, Shigella dysenteriae, Escherichia coli, Burkholderia mallei, Listeria monocytogenes, Burkholderia pseudomallei, Yersinia pestis* (YP), and *Francisella tularensis*. In some embodiments, the organism is a biological warfare agent (BWA). In some embodiments, the target molecule is from a spore. In other embodiments, the target biological molecule is a prion. Prions play a role in the etiology of bovine spongiform encephalopathy, Creutzfeldt-Jakob Disease, variant Creutzfeldt-Jakob Disease, Gerstmann-Sträussler-Scheinker syndrome, Fatal Familial Insomnia and kuru. In additional embodiments, the target biological molecule is a protein, a peptide, lipid, carbohydrate, or antibody.

In some embodiments, the target molecule is non-pathogenic, for example, a nucleic acid a host produces, e.g., during infection.

In certain embodiments, the target biological molecule comprises a nucleotide sequence that is at least about 70%, about 80%, about 90%, about 95%, about 98%, about 99% or about 100% identical to a wild-type nucleotide sequence of an organism. In some embodiments, the target biological molecule comprises a nucleotide sequence that is 100% identical to a nucleotide sequence of an organism.

As used herein, "sequence identity" means that two nucleotide or amino acid sequences, when optimally aligned, such as by the programs GAP or BESTFIT using default gap weights, share at least 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm described in Smith & Waterman, *Adv. Appl. Math.* 2:482 (1981), by the homology alignment algorithm described in Needleman & Wunsch, *J. Mol. Biol.* 48:443 (1970), by the search for similarity method described in Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*), all of which are incorporated by reference in their entirety. One example of an algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (accessible through the National Institutes of Health NCBI internet server). Default program parameters can typically be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Biological Samples

The term "biological sample" refers to a material of biological origin (e.g., cells, tissues, organs, bodily fluids, or an environmental source). Biological samples can comprise, for example, nucleic acid (e.g., DNA or RNA) extracts, cell lysates, whole cells, protein extracts, tissues (including tissue biopsies), organs, lipid extracts, and bodily fluids (e.g., blood, wound fluid, plasma, serum, spinal fluid, lymph fluid, tears, saliva, mucus, sputum, urine, semen, amniotic fluid). A biological sample can be obtained from any of a variety of suitable sources. In one embodiment, the biological sample is obtained from a subject (e.g., a human, a non-human mammal, a patient). In a particular embodiment, the biological sample is obtained from a human.

In some embodiments, a biological sample can be obtained from an environmental source, such as air, water, or soil.

Probes and Labels

As used herein, the term "probe" refers to a nucleic acid molecule that includes a target-binding region that is substantially complementary to a target sequence in a target nucleic acid and, thus, is capable of forming a hydrogen-bonded duplex with the target nucleic acid. Typically, the probe is a single-stranded probe and can have one or more detectable labels to permit the detection of the probe following hybridization to its complementary target. As used herein, "target-binding region" refers to a portion of a probe that is capable of forming a hydrogen-bonded duplex with a complementary target nucleic acid.

In a particular embodiment, the probes used in the present disclosure are oligonucleotide probes (e.g., single-stranded DNA oligonucleotide probes). Typical oligonucleotide probes are linear and range in size from about 6 to about 100 nucleotides, preferably, about 20 to about 50 nucleotides. In a particular embodiment, the oligonucleotide probes are about 30 nucleotides in length.

In some embodiments, suitable probes for use in the methods of the present disclosure include, but are not limited to, DNA probes, RNA probes, peptide nucleic acid (PNA) probes, locked nucleic acid (LNA) probes, morpholino probes, glycol nucleic acid (GNA) probes and threose nucleic acids (TNA) probes. Such probes can be chemically or biochemically modified and/or may contain non-natural or derivatized nucleotide bases. For example, a probe may contain modified nucleotides having modified bases (e.g., 5-methyl cytosine) and/or modified sugar groups (e.g., 2'O-methyl ribosyl, 2'O-methoxyethyl ribosyl, 2'-fluoro ribosyl, 2'-amino ribosyl). In some embodiments, useful probes can be linear, circular or branched and/or include domains capable of forming stable secondary structures (e.g., stem-and-loop and loop-stem-loop hairpin structures). In one embodiment, linear probes are used.

Methods of producing probes useful in the methods of the present disclosure are well known in the art and include, for example, biochemical, recombinant, synthetic and semi-synthetic methods. (see, e.g., Glick and Pasternak, Molecular Biotechnology: Principles and Applications of Recombinant DNA (ASM Press 1998)). For example, solution or solid-phase techniques can be used.

Probes useful in the methods of the present disclosure can further comprise one or more labels (e.g., detectable labels). Labels suitable for use according to the present disclosure are known in the art and generally include any molecule that, by its nature, and whether by direct or indirect means, provides an identifiable signal allowing detection of the probe.

The term "label," as used herein, refers to a moiety that indicates the presence of a corresponding molecule (e.g., a probe molecule) to which it is bound. In some embodiments, the label is attached to the molecule via a linker, crosslinker, or spacer.

A "linker," in the context of attachment of two molecules (whether monomeric or polymeric), means a molecule (whether monomeric or polymeric) that is interposed between and adjacent to the two molecules being attached. A "linker" can be used to attach, e.g., probe molecule and a label (e.g., a detectable label, e.g., a spectroscopic dye). The linker can be a nucleotide linker (i.e., a sequence of the nucleic acid that is between and adjacent to the non-adjacent sequences) or a non-nucleotide linker.

Probe labeling can be performed using standard laboratory techniques known in the art, e.g., during synthesis or, alternatively, post-synthetically, for example, using 5'-end labeling. Labels can be added to the 5', 3', or both ends of the probe (see, e.g., U.S. Pat. No. 5,082,830), or at base positions internal to the oligonucleotide.

In a particular embodiment, the probes employed in the present disclosure include one or more Raman labels. "Raman label" or "Raman-active label" as used herein, is any substance which produces a detectable Raman spectrum, which is distinguishable from the Raman spectra of other components present, when illuminated with a radiation of the proper wavelength. Other terms for a Raman label include "Raman dye" and "Raman reporter molecule."

A variety of suitable Raman labels are known in the art, including, but not limited to, 4-(4-Aminophenylazo)phenylarsonic acid monosodium salt, arsenazo I, basic fuchsin, Chicago sky blue, direct red 81, disperse orange 3, HABA (2-(4-hydroxyphenylazo)-benzoic acid), erythrosin B, trypan blue, ponceau S, ponceau SS, 1,5-difluoro-2,4-dinitrobenzene, cresyl violet and p-dimethylaminoazobenzene. In some embodiments, the labels can be any of those described herein. In some embodiments, the label is a cyanine dye such as Cy3, Cy3.5, Cy5, Cy7, and Cy7.5. In some embodiments, the dye is Rhodamine 6G.

One or more Raman labels may be bound to a particle (e.g., nanoparticle, such as a gold nanoparticle). For particle-based detection probes, the Raman labels or dyes can be attached directly or indirectly to the particle. The Raman label can be modified with a functional group, e.g., a thiol, amine, or phosphine that can bind to the surface of the particle such as a metallic nanoparticle. If desired, the Raman dye can be further functionalized with a molecule such as an oligonucleotide (e.g., polyadenosine, polythymidine) for enhanced nanoparticle stability or with a specific binding pair member (such as an oligonucleotide having a sequence that is complementary to at least a portion of a nucleic acid target or a receptor for a particular ligand). Alternatively, the Raman label can be conjugated with a molecule or any linker, e.g., polyA or polyT oligonucleotide, that bears a functional group for binding to the particle. The polyA or polyT oligonucleotide to which the Raman labels are conjugated is not complementary to any target nucleic acid.

Nucleic Acid Hybridization

The term "hybridization conditions" refers to hybridization conditions that affect the stability of hybrids, e.g., temperature, salt concentration, pH, formamide concentration, incubation time, and the like. These conditions can be empirically optimized to maximize specific binding, and minimize nonspecific binding, of a probe to a target nucleic acid. The term "stringent hybridization conditions" refers to hybridization conditions under which complementary (e.g., substantially complementary) nucleic acids specifically hybridize with one another. In some embodiments, the conditions are isothermal.

Generally, hybridization is performed under conditions sufficient for a probe to hybridize with a complementary target nucleic acid in a biological sample. Suitable hybridization buffers and conditions for in situ hybridization techniques are generally known in the art. (See, e.g., Sambrook and Russell, supra; Ausubel et al., supra. See also Tijssen, Laboratory Techniques in Biochemistry and Molecular Biology, Vol. 24: Hybridization with Nucleic Acid Probes (Elsevier, N Y 1993)).

Optimal hybridization conditions for a given target sequence and its complementary probe will depend upon several factors such as salt concentration, incubation time, and probe concentration, composition, circumstances of use and length, as will be appreciated by those of ordinary skill in the art. Based on these and other known factors, suitable binding conditions can be readily determined by one of ordinary skill in the art and, if desired, optimized for use in accordance with the present systems and methods. Typically, hybridization is carried out under stringent conditions that allow specific binding of substantially complementary nucleotide sequences. Stringency can be increased or decreased to specifically detect target nucleic acids having 100% complementarity or to detect related nucleotide sequences having less than 100% complementarity (e.g., about 70% complementarity, about 80% complementarity, about 90% complementarity). Factors such as, for example, the length and nature (DNA, RNA, base composition) of the probe sequence, nature of the target nucleotide sequence (DNA, RNA, base composition, presence in solution or immobilization) and the concentration of salts and other components in the hybridization buffer (e.g., the concentration of formamide, dextran sulfate, polyethylene glycol and/or salt) in the hybridization buffer/solution can be varied to generate conditions of either low, medium, or high stringency. These conditions can be varied based on the above factors, either empirically or based on formulas for determining such variation (see, e.g., Sambrook et al., supra; Ausubel et al., supra).

Washes are performed in a solution of appropriate stringency to remove unbound and/or non-specifically bound probes. An appropriate stringency can be determined by washing the sample in successively higher stringency solutions and reading the signal intensity between each wash. Analysis of the data sets in this manner can reveal a wash stringency above which the hybridization pattern is not appreciably altered and which provides adequate signal for the particular probes of interest.

Suitable wash buffers for in situ hybridization methods are generally known in the art (See, e.g., Sambrook and Russell, supra; Ausubel et al., supra. See also Tijssen, Laboratory Techniques in Biochemistry and Molecular Biology, Vol. 24: Hybridization with Nucleic Acid Probes (Elsevier, N Y 1993)). Wash buffers typically include, for example, one or more salts (e.g., sodium salts, lithium salts, potassium salts) and one or more detergents (e.g., an ionic detergent, a non-ionic detergent). Suitable detergents for a wash buffer include, but are not limited to, sodium dodecyl sulfate (SDS), Triton® X-100, Tween® 20, NP-40, or Igepal® CA-630. De-ionized water may also be used as a wash solution.

Breadboard

A breadboard is a board for making electrical or experimental electrical circuits. Systems as described herein can be constructed on a breadboard, be part of a breadboard, a breadboard can be part of a system, and in some embodiments the system can be referred to as a "breadboard"

Nanoparticle Complex

As used herein, nanoparticle complex refers to a nanoparticle coupled to one or more probe molecules via a dye. The one or more probe molecules can be identical in sequence or structure, or can be different. One or more probe molecules can be configured by an end-user according to one or more desired target molecules. The dye used can additionally be configured by an end-user depending on the analysis method.

Microbead Complex

As used herein, microbead complex refers to a microbead coupled to one or more capture molecules. The one or more capture molecules can be identical in sequence or structure, or can be different. One or more capture molecules can be configured by an end-user according to one or more desired target molecules.

A microbead complex as used herein can also refer to a microbead coupled to one or more capture molecules, hybridized to a target molecule, and the target molecule can further be hybridized to a nanoparticle with one or more probe molecules couple to the nanoparticle via one or more dyes.

Discussion

Described herein are methods and devices for manipulating and analyzing fluids containing biological targets. Devices and methods as described herein can prepare analytical assays for biological targets utilizing microbeads and/or nanoparticles in a non-stationary phase, and can detect or analyze biological targets from these assays quickly. Devices and methods as described herein can comprise integrated systems utilizing more than one of a sample isolation module, a cell lysis module, a biological target purification module, an assay mixing module, a flow path, and an analysis region. Devices and methods as described herein can be comprised of microfluidic components configured for femto-, pico-, nano- and micro-liter volumes.

Embodiments of the present disclosure can analyze biological material samples obtained from bulk, body fluids, or environmental sources, for example, by detecting and identifying biological target molecules (e.g., nucleic acid) from the biological material samples. Environmental sources can include air, soil, or water, for example. Biological samples can include a sample from a cell, bacterium, virus, fungus, spore, and virus for example. Embodiments also allow for detection of biomarkers, which can include non-pathogen target molecules, such as DNA, RNA, lipid, carbohydrate, antibodies, or protein that a human or animal host produces during infection by a pathogen. From a sample of biological material, in some embodiments devices can lyse the cells, extract and purify cell DNA, capture and label the DNA onto microbeads, and then detect and identify the DNA using surface enhanced Raman spectroscopy (SERS), for example. Embodiments can make use of SERS labels, random array assays, and SERS detection. Embodiments are scalable to handheld or other portable sensor platforms, such as a platform configured for use in a vehicle. Embodiment methods can enable a biowarfare agent (BWA), microorganism, cell, bacteria, virus, spore, or fungus, for example, to be analyzed quickly by simply injecting a biological sample, pressing a button on a device, and obtaining analysis results within as little as 30 minutes, for example. Thus, embodiments can be much faster than and just as sensitive as existing laboratory-based devices.

Advantages of embodiments of the present disclosure can include fast hybridization kinetics for fast assay formation and rapid detection of biological targets, such as those present in biological warfare agents, an ability to analyze multiple assays in a single cartridge simultaneously, and an ability to obtain SERS readouts with a fixed optical configuration. Furthermore, embodiments of the present disclosure can be highly reliable for field use, with no moving parts. Test cartridges can also be small, scaling only a volume of microscopic bead complexes to add additional assays.

Described herein are embodiments of systems and corresponding methods, for detecting one or more target biological molecules. Systems (e.g., apparatuses, devices, analysis systems, analysis devices, target analysis devices) are described herein that can detect a biological target molecule. A system can be comprised of one or more interchangeable modules (as used herein, a module can also refer to a chamber). Modules used in a system or systems as described herein, can be integrated into a single system or mobile cartridge and configured for sample isolation, sample lysis, target purification, target assays, and target flow. In embodiments of the present disclosure, systems as described herein can include a reaction chamber (a reaction chamber can include any one or more of a sample isolation module, a cell lysis module, a biological target purification module, and an assay mixing module) that can be configured to enable formation of a biological molecule bead complex, a flow path (interchangeably referred to herein as a channel) configured to enable transport of the bead complex from the reaction chamber to an analysis region, and a spectrometer configured to analyze the bead complex at the analysis region. Systems as described herein can be configured to handle, process, and transport fluids on a microfluid scale (microliter volumes). Parts, or modules, of the system can be self-contained in a cartridge with a small footprint that is suitable for field use.

Systems as described herein can have a reaction chamber. A reaction chamber can comprise one or modules, and the modules can be sample isolation modules, cell lysis modules, biological target purification modules, assay mixing modules, flow modules, or others, as described herein. Modules within the reaction chamber can be in fluidic communication with each other. A reaction chamber can contain more than one type of a certain module. Modules can be connected in series or in parallel, or both, and one skilled in the art could configure a reaction chamber according to the present disclosure according to a given application or desired analysis target[s]. A reaction chamber as described herein can comprise a sample lysis module and/or a target purification module. In some embodiments, a reaction chamber additionally can include a sample isolation module.

A reaction chamber can isolate biological samples and can contain a sample isolation module. As described herein, a module for sample isolation can be a sample isolation module. In an embodiment, a fluid (air or water) containing a biological sample can flow into a sample isolation module, and the fluid can flow through one or more filters in the sample isolation module to isolate biological samples of a desired size. A sample isolation module can be configured to isolate biological samples of a desired size using one or more filters, and sizes of filters and number of filters can be adjusted according to the desired biological sample of interest. Examples of filters that can be used can be 20 µm filters, 2 µm filters, and 0.22 µm filters. If more than one filter is used in module, the filters can be connected in fluidic communication in series and/or in parallel. A sample isolation module can be connected in fluidic communication with one or more additional modules within the system in series and/or in parallel. A sample isolation module can further comprise a sample inlet, allowing for input of samples containing biological samples into the system by a device such as a pipette or a syringe. An example of a sample inlet can be an injection port in a valve, or a rubber gasket as used in common needle-based clinical blood collection tubes.

A reaction chamber can lyse cells and can contain a cell lysis module. As described herein, a module for cell lysis can be a cell lysis module. A cell lysis module can lyse cells and/or fragment cellular components, such as nucleic acids, lipids, carbohydrates, and proteins. A cell lysis module can be comprised of a chamber where one or more biological samples are lysed. In an embodiment, a cell lysis module is configured for thermal cell lysis. For example, a cell lysis module for thermal cell lysis can be comprised of a capillary tube (which can be the chamber in this embodiment) coupled to one or more heating elements, wherein one or more biological samples within the tube are heated by the one or more heating elements. The one or more heating elements can be operated manually or can be electrically couple to a controller and/or a computing device for automated operation. The cell lysis module can be in fluid communication with a sample isolation module, connected in series. A system can comprise more than one sample isolation module and more than one cell lysis module, and the modules can be in configured for series and/or parallel fluid communication between modules depending on a desired application.

In another embodiment, a cell lysis module can be configured for enzymatic cell lysis. A cell lysis module configured for enzymatic cell lysis can comprise a chamber or an area where one or more cells can be mixed with a buffer and/or lysis enzyme (for example a lysozyme). A cell lysis module can configured for enzymatic cell lysis can additionally comprise one or more reagent chambers in fluidic communication with the mixing chamber or area, that store components used for enzymatic cell lysis. One or more fluid pumps can be used to mix the components (such as cells, buffers, and/or enzymes) within the module. Other configurations of cell lysis modules can be realized according to other cell lysis protocols known in the art (i.e., mechanical methods such as vortexing or other methods, such as sonication). In these configurations, a cell lysis module can comprise a sample chamber or area coupled to a mechanical lysis element. A cell lysis module as described herein could utilize more than one type of cellular lysis, for example could comprise a heating element in addition to a mechanical lysis element. One skilled in the art could configure a cell lysis module according to a desired cell type or application. A cell lysis module can further comprise a sample inlet, allowing for input of biological samples into the system by a device such as a pipette or a syringe. An example of a sample inlet can be an injection port in a valve, a rubber gasket as used in common needle-based clinical blood collection tubes, and/or a receiving tube.

Cell lysing modules can additionally be configured to lyse a cell to release the target DNA molecule. The cell lysing chamber can be coupled to the reaction chamber via one or more valves, and the system can also include a controller operatively coupled to the one or more valves to cause the valves to open and close in the sequence enabling the target DNA molecule to flow from the cell lysing chamber to the reaction chamber.

A reaction chamber can isolate or purify biological targets from biological samples and can contain a biological target purification module. As described herein, a module for biological target purification and/or isolation can be a biological target purification module (also referred to herein as biological target isolation modules). A biological target purification module can be configured to receive components of biological samples from one or more cell lysis modules. A biological target isolation module can be in fluidic communication with one or more cell lysis modules, in series and/or parallel. Biological target isolation modules as described herein can have a chamber, area, or device in or on which biological targets are isolated. Biological target isolation modules can further comprise one or more reagent chambers or vessels (which can be configured to receive reagents) where one or more reagents are stored, and the chambers can be in fluidic communication with an area, chamber, or part of the module where purification takes place. One or more pumps can be used to mix biological sample components and reagents that are stored within the biological target purification module. In an embodiment, biological targets are isolated on one or more silica gel membranes or capillaries.

A biological target purification module can be configured for purification or isolation of components of biological samples or components of cells, for example any one or more of DNA, RNA, lipid, carbohydrate, protein, antibody, etc., individually or in combination. Isolation of these components is well known in the art, and one skilled in the art would be able to configure a biological target purification module according to a desired biological target of interest. Operation of the module can be performed by a user manually according to well-known steps of target isolation in the art. Additionally, operation of the module can be automated with the assistance of a pumps, valves, controller and/or computing device (individually or in combination) configured or programmed via to send instructions that would allow the module to perform purification steps known in the art. A biological target purification module can also be configured to send purified (for example about 75%- to 100% pure target) and/or isolated targets to other modules, such as an assay mixing module, and can be in fluidic communication with other modules. A biological target purification module can also comprise heating or cooling elements, to heat or cool material therein.

Figure 26:
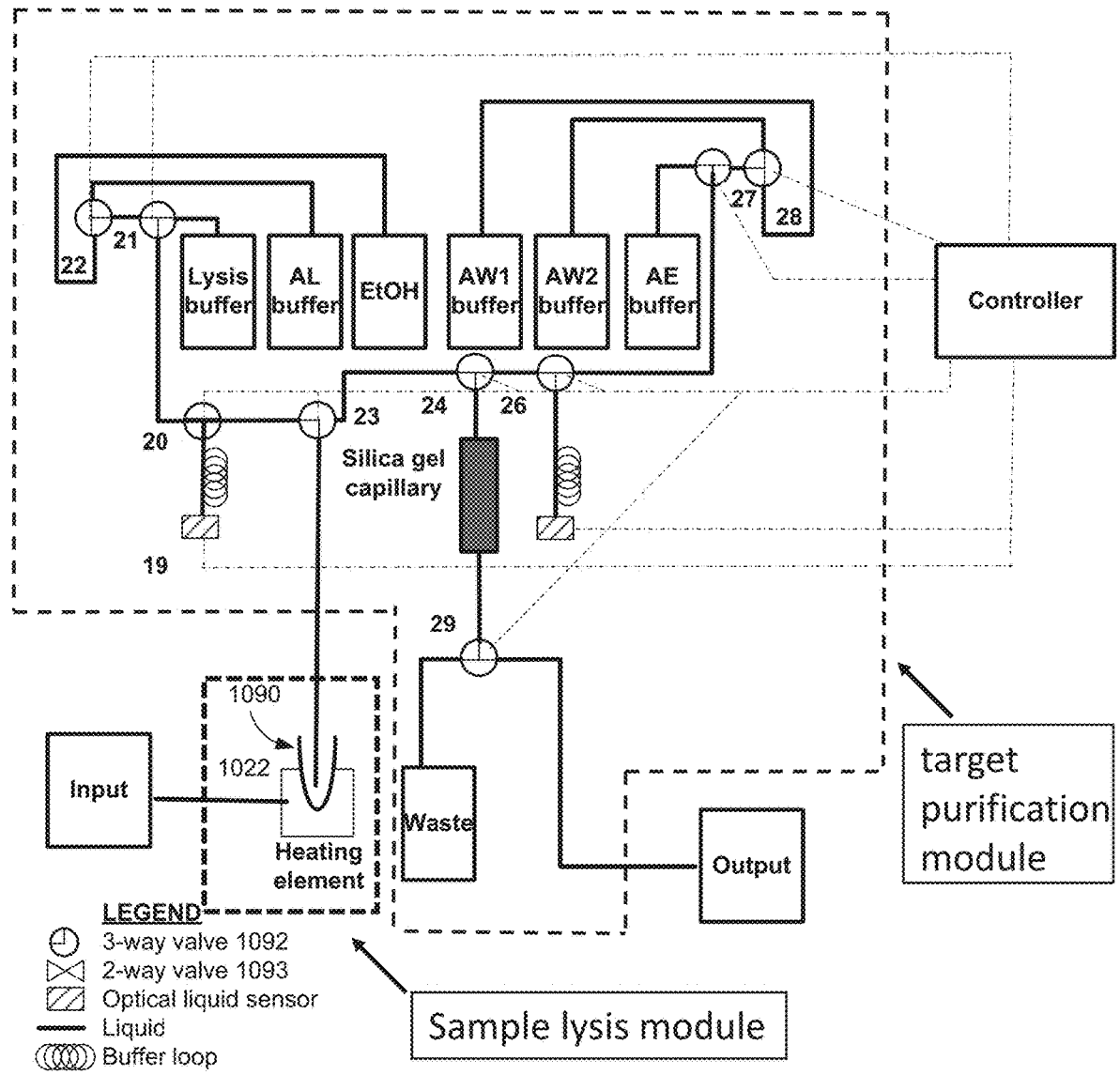
FIG. 26 is an embodiment of a sample lysis module configured for thermal lysis in fluid communication with a biological target purification module configured for DNA extraction as described herein.

FIG. 26 shows an embodiment of a biological target purification module for nucleic acid purification, with a configuration based on a commercially available DNeasy® kit from the vendor Qiagen and associated reaction protocol. A silica gel capillary is present for nucleic acid isolation (although other devices with one or more silica membranes can be used), the module is configured to hold reagents according to the kit in separate reagent chambers or vessels, and the specific fluidic configuration of the module has been realized according to steps of the kit. In the figure, electrical connections between valves and a controller are shown, and the controller and/or a computing device can be programmed to carry out the steps laid out in the kit automatically with the assistance of one or more pumps (not shown). Operation of the module can also be performed manually by a user. Optional optical sensors are also shown in the example, which can be used by the controller and/or computing device for feedback loops that can monitor, start fluid flow, and/or actively regulate fluid flow in real-time as the target purification assay commences. Opening and closing of different valves as shown can be down manually by a user or automatically according to steps in the instruction manual of the kit. Optional buffer loops are shown as well which can be utilized to clear fluid lines or wash the silica between uses. Based on the example embodiment shown in FIG. 26, one skilled in the art could modify the module for other kits or to perform isolation of targets other than nucleic acids.

A reaction chamber can prepare biological targets for detection and can contain an assay mixing module. As described herein, a module for assay mixing can be an assay mixing module or an assay chamber. An assay mixing module can comprise a region, area, or chamber within which isolated biological targets can be mixed with detection assay components, such as labels for detection. An assay mixing module can be in fluid communication with a biological target purification module, and be configured to receive isolated or purified biological targets from the assay biological target purification module. An assay mixing module can further comprise a thermal cycler for temperature cycling to aid in mixing and binding of target biological samples to reagent components.

An assay mixing module can comprise one or more reagent vessels. An assay mixing module can comprise one or more reagent or buffer loops. Reagents in the assay mixing module can comprise components that can bind to biological sample targets. Reagent components can comprise beads (which be glass), capture molecules (which can be short peptides or oligonucleotides of predetermined sequence, for example), probe molecules (which can be short peptides or oligonucleotides of predetermined sequence, for example), nanoparticles, dyes, silver particles, gold particles, phosphate buffered saline, nitrate buffer, silver solution, and an optional chloride solution. Valves can be used in the module to direct or restrict flow of reagents. Pumps can be utilized to drive fluid flow in the module. Valves and pumps can be operated manually, or can be electrically coupled to a controller and/or a computing device programmed to send instructions to operate the module according to a detection assay reaction protocol. The module can be operated manually, automated with the assistance of a controller and/or a computing device, or a combination thereof. Reagent vessels and/or loops can be configured to receive liquid or air, by way of a syringe, pipette, micropipette, or simply by pouring liquid in. An example of an embodiment of an assay mixing chamber is show in FIG. 27.

Figure 1B:
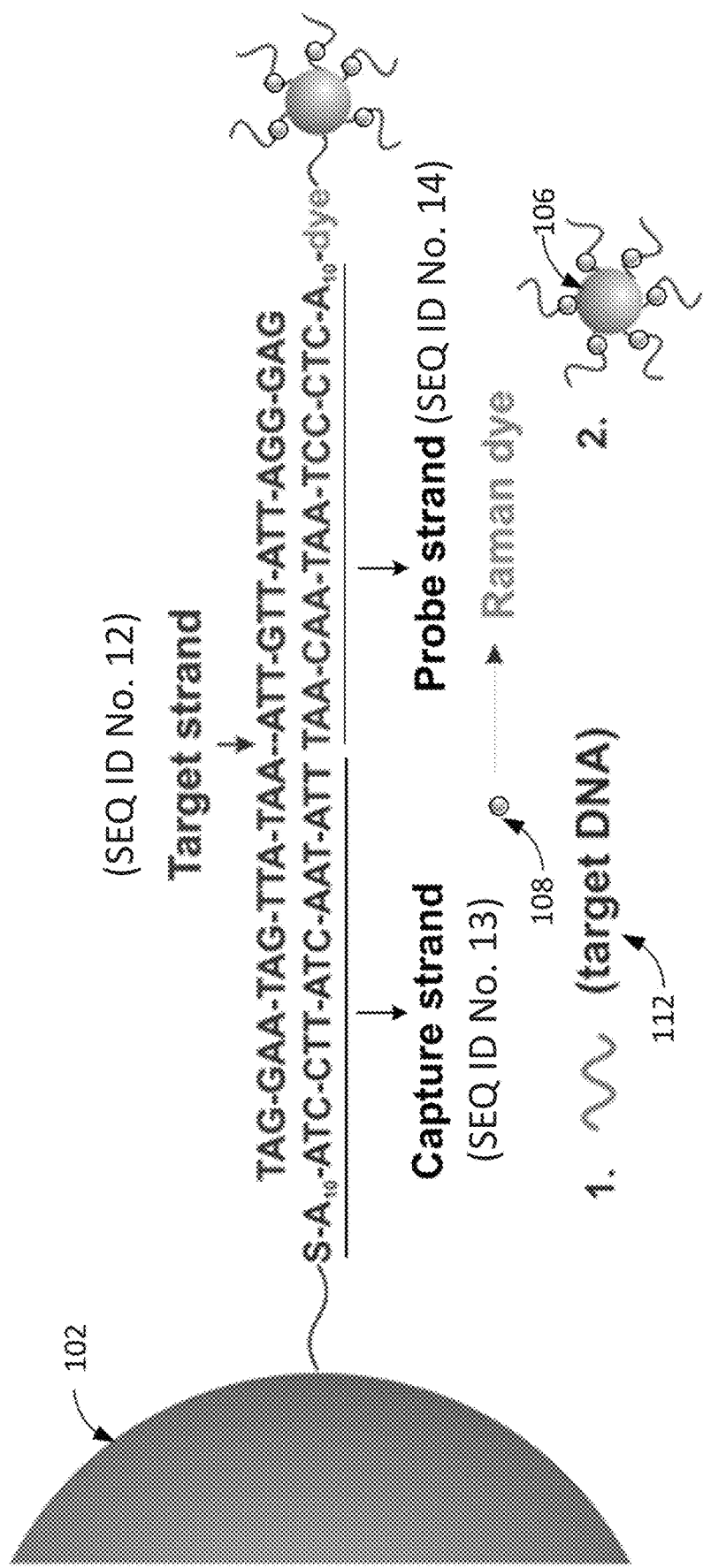

In an embodiment, the assay mixing module can comprise: (1) one or more microbeads with a capture molecule coupled thereto, and (2) one or more nanoparticles having a probe molecule coupled thereto via a label. The capture molecule and probe molecule can be coupled together via a biological target to form a biological molecule bead complex, and the assay mixing module can be configured to couple or hybridize these components. Examples of coupled or hybridized bead complexes are shown in FIG. 1A and FIG. 1B. FIG. 1B shows an example target sequence (SEQ ID No. 12), an example capture strand (SEQ ID No. 13), and an example probe strand (SEQ ID No. 14). These components can be present as compositions in one or more reagent solutions present in one or more reagent vessels or loops. Microbead compositions and nanoparticle compositions can be present in solutions as individual reagents, or can be present in one mixed reagent.

The biological target that can be coupled to or hybridized with the above microbeads and nanoparticles can be a nucleic acid (e.g., DNA or RNA) molecule. The label can be a spectroscopic dye for Raman spectroscopic analysis or other analysis (fluorescence, for example). The biological molecule bead complex can be of a size to fit within a focal point or diameter of a cross-section of a laser beam that can be configured to analyze the bead complex. The microbead can be at least two orders of magnitude larger than the nanoparticles. The microbead and nanoparticles can be within corresponding collections of multiple microbeads and multiple nanoparticles in respective separate solutions or a common solution.

The assay mixing module can also include at least two microbeads having different respective capture molecules coupled thereto and at least two nanoparticles having a different respective probe molecules coupled thereto via different respective labels. The different respective capture molecules and different respective probe molecules can be, respectively, coupled together via different respective biological targets to form a random array of at least two biological molecule bead complexes in random locations in a fluid.

The label can be configured to provide a Raman spectrum to a portable Raman spectrometer. In some embodiments, the capture molecule can be a nucleic acid (e.g., DNA or RNA) molecule configured to bind to the biowarfare agent or component thereof. At least one of the capture molecule and probe molecule can be an aptamer, antibody, or DNA molecule. The microbeads can have multiple capture molecules coupled thereto, and the multiple capture molecules can be the same. The microbead can have multiple capture molecules coupled thereto, and the multiple capture molecules can be different. The nanoparticles can be gold nanoparticles and can have one or more silver nanoparticles attached thereto. Further description can be found in the example section below.

An assay mixing module or reaction chamber can form a bead complex or molecular bead complex. The biological molecule bead complex can be configured to be coupled to a target nucleic acid molecule present in a biological sample. The bead complex can be a DNA bead complex and can include a microbead with a biological capture molecule coupled thereto and a nanoparticle coupled to a biological probe molecule via a label. The reaction chamber can be configured to facilitate coupling of the capture molecule and probe molecule together through a binding reaction with a target biological molecule to form the bead complex. In some embodiments, biological capture and probe molecules can include DNA, RNA, proteins, aptamers, or antibodies. Molecules coupled to microbeads and nanoparticles can be nucleic acids of a pre-determined sequence. The pre-determined sequence can be a complementary nucleic acid sequence to a nucleic acid sequence present. The nucleic acid sequence present in a biological sample, can be nucleic acid of a cell or organism, or for example DNA of a biological warfare agent such as *Bacillus anthracis*.

An assay mixing module can additionally comprise an air or gas source and/or element to bubble components of a detection assay that are mixed or to separate reagents before mixing. Example 14 below contains some examples of assays and protocols that can be embodied in an assay mixing module of systems described herein.

The label can be a spectroscopic dye, which can have an absorption band at a wavelength of the laser configured to illuminate the bead complex at the analysis region. A matching of the wavelength of the laser with the absorption band can be used to enhance the strength of a signal produced by the molecule bead complex greatly through surface enhanced resonance Raman spectroscopy, for example. Absorption wavelengths of dyes and emission wavelengths of lasers are well known in the art, and one skilled in the art would be able to choose a suitable dye and laser based on the absorption wavelength of the dye and emission wavelength of the laser. It can additionally be possible to multiplex dyes, and have bead complexes with dyes having different absorption wavelength or a composition of bead complexes with different dyes having different absorption wavelengths.

The spectrometer can be a Raman spectrometer and can be configured to cause the bead complex to react to the surface enhanced resonance Raman spectroscopy stimulation signal, such as a laser beam. The spectrometer, alternatively, can be configured to perform fluorescence spectroscopy to analyze the bead complex and can be configured to analyze, at the analysis region, a plurality of bead complexes having different respective, associated target biological molecules.

Systems as described herein can also have a one or more flow paths that direct or transport labeled biological targets from the assay mixing module or reaction chamber to one or more analysis platforms or analysis regions. The flow path can be a channel of a microfluidic device, and the analysis region can be a part of a microfluidic device containing a flow path. Transporting the bead complex through the flow path can include transporting the complex through a microfluidic channel. The bead complex containing one or more microbead complexes can be in a fluid or aqueous suspension, and can be non-stationary.

Valves (2-way, 3-way, or more depending on the configuration of the module) can be used to direct or restrict flow within the systems or one or more modules of systems of the present disclosure (to the filters, away from the filters, to another module, etc.). Valves can be controlled manually or can be electrically (aka operatively) connected to a controller and/or a computing device as described herein and control electronically (i.e. in an automated system).

Differences or changes in fluid pressure (positive or negative, more positive or more negative, etc.) can drive fluid through the system and/or through individual modules of the system. Pressure changes that drive fluid can be derived from one or more pumps. One or more pumps as described herein can be in fluid communication with systems as described herein and connected to a system or to individual modules of a system in series or in parallel. One or more pumps as described herein can be operatively coupled to or integrated with a reaction chamber, one or more modules of a reaction chamber, one or more reagent vessels, one or more reagent loops, or any other components of the system which requires the flow or mixing of fluid. One or more pumps can be integrated into reagent chambers and/or mixing chambers in individual modules in order to drive the flow of one or more reagents through a system. Different combinations of pump types can also be realized within a system. For example, a block syringe pump can drive targets through the system as a whole, and solid chemical propellant pumps or DEP pumps can be integrated into individual modules of a system or into individual reagent chambers or reagent loops. Examples of pumps that can be used in the system include syringes, automated syringe pumps, dielectric pumps, solid chemical propellant pumps, and others known in the art. Different pump configurations can be realized according to the present disclosure, and one skilled in the art could select a pump configuration depending on the specific needs of the system.

Figure 23:
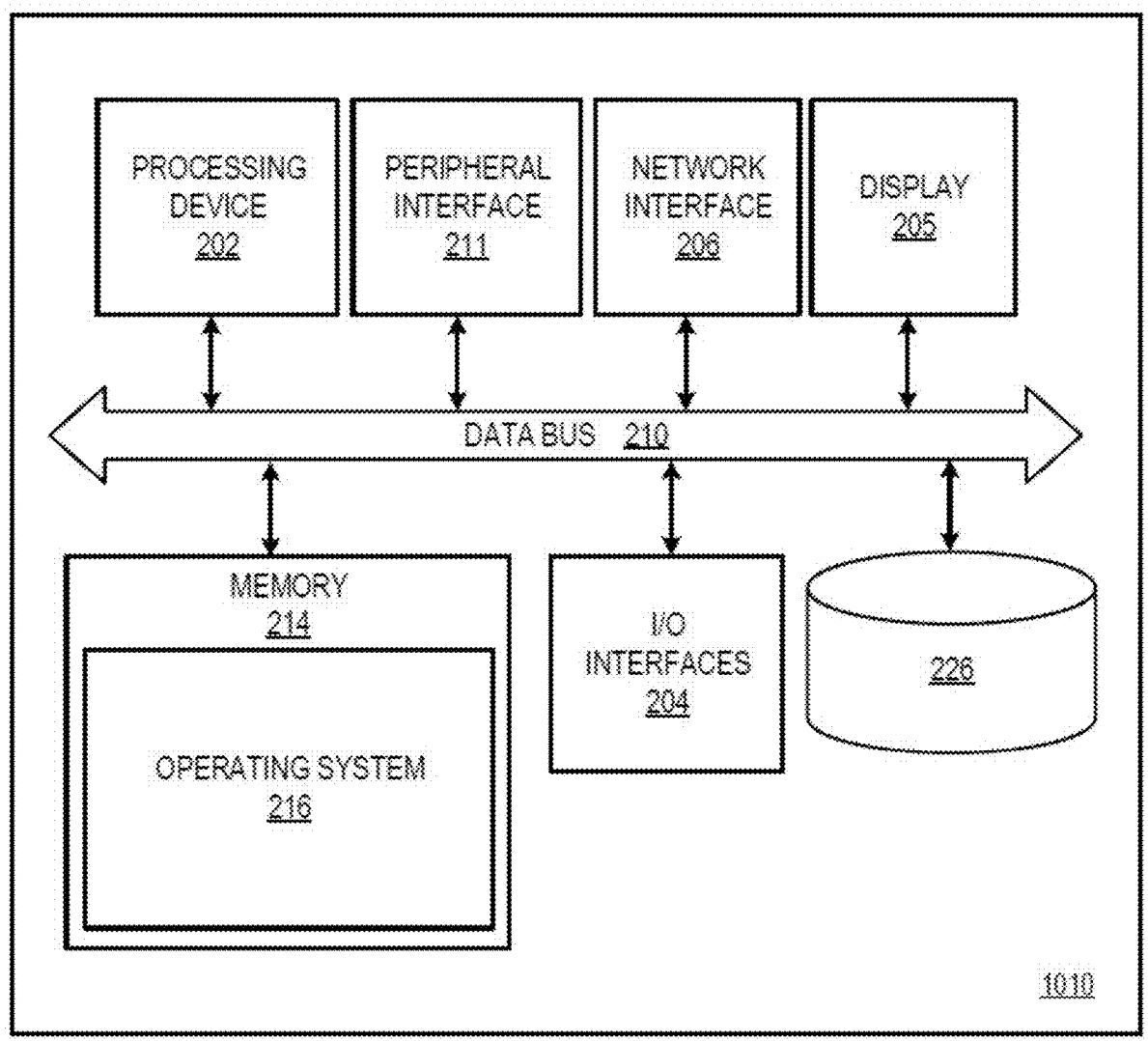
FIG. 23 is a schematic diagram of a computing device or apparatus 1010 which can be coupled to systems as described herein for automated operation of the systems.
Figure 24A:
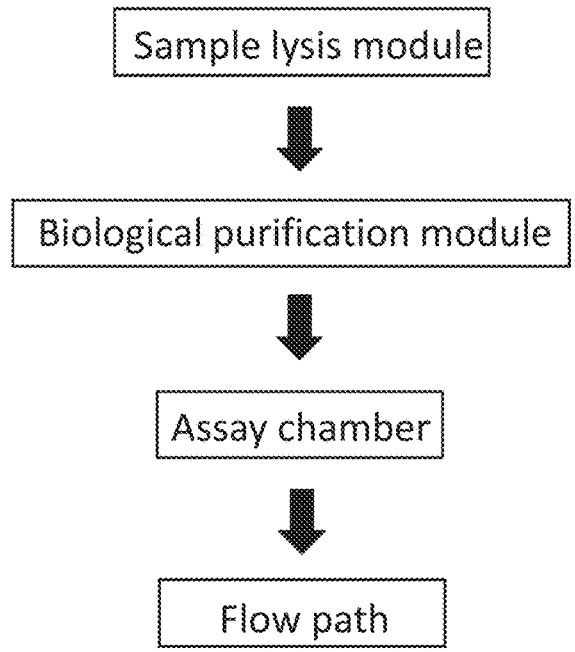
FIGS. 24A-24D are block diagrams showing embodiments of systems with examples of module configuration as described herein.
Figure 24B:
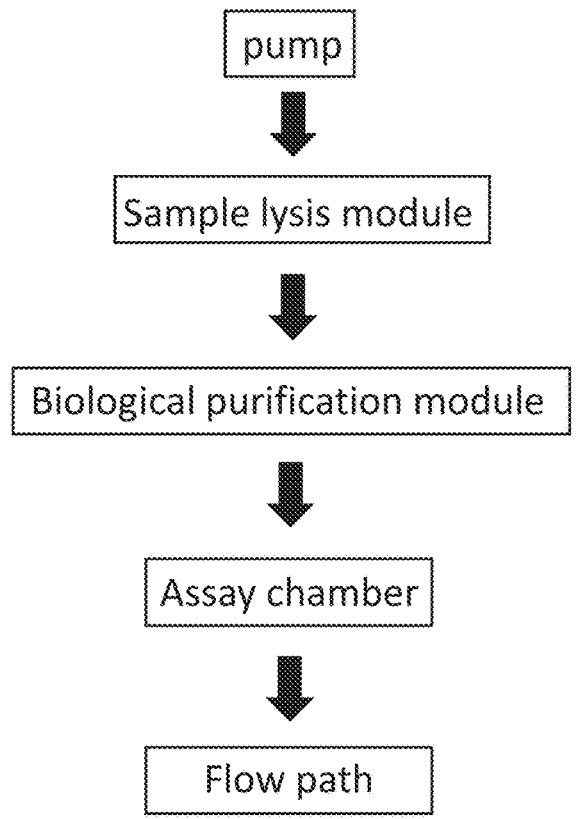
Figure 24C:
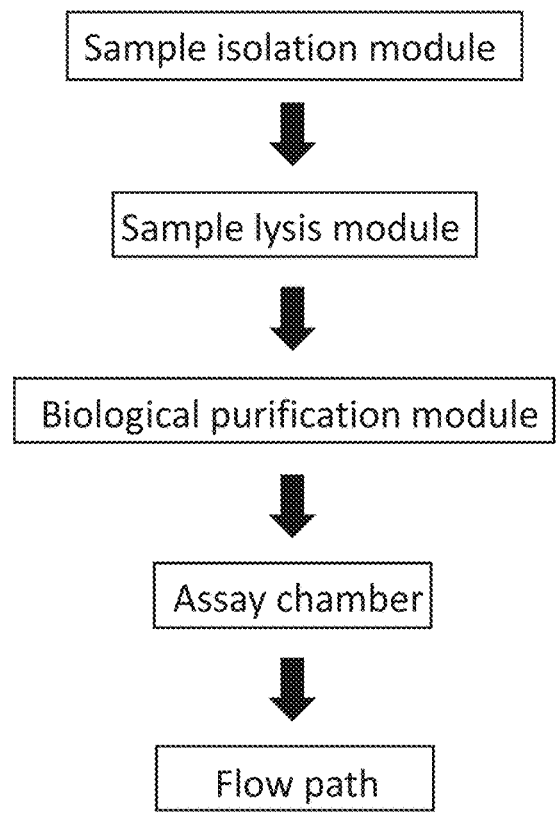
Figure 24D:
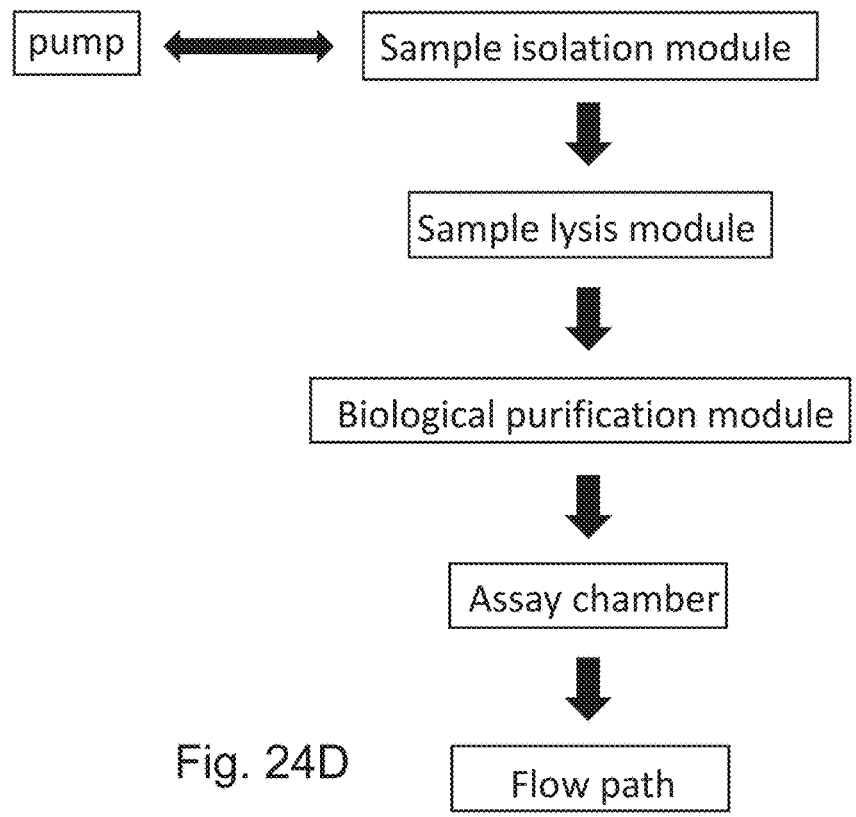

In certain embodiments, the system can also include a controller configured to control fluid control devices (such as valves and/or pumps) to direct or initiate movement of fluids throughout the system. The controller, for example, can also be configured to open or close one or more valves to enable transport of the bead complex from the reaction chamber to the analysis region. The system and/or the controller can be electrically coupled to a computing device as shown in FIG. 23, and the system can be configured so that electronic data can be passed to and from the system, a controller, and/or a computing device. Configuration of electronic devices and circuits is routine in the art and one skilled in the art would be able to configure the device according to the desired application.

Computing devices as described herein can execute software that contains instructions for pump operation, valve operation, controller operation, and can process data from sensors, such as optical sensors which can monitor and generate real-time data about the environment within the system. The system can utilize one or more electronic feedback loops with sensors coupled to a controller and/or a computing device to assist in automated operation of the system. In certain embodiments, a controller can be a computing device.

Another embodiment of the present disclosure is a kit that can include a microbead with a capture molecule coupled thereto and a nanoparticle having a probe molecule coupled thereto via a label. The capture molecule and probe molecule can be configured to be coupled together via a biological target to form a biological molecule bead complex.

The biological target can be a nucleic acid (e.g., DNA or RNA) molecule. The label can be a spectroscopic dye. The biological molecule bead complex can be of a size to fit within a focal point of a laser beam configured to analyze the bead complex. The microbead can be at least two orders of magnitude larger than the nanoparticles. The microbead and nanoparticles can be within corresponding collections of multiple microbeads and multiple nanoparticles in respective separate solutions or a common solution.

The kit can also include at least two microbeads having different respective capture molecules coupled thereto and at least two nanoparticles having a different respective probe molecules coupled thereto via different respective labels. The different respective capture molecules and different respective probe molecules can be configured to be, respectively, coupled together via different respective biological targets to form a random array of at least two biological molecule bead complexes in random locations in a fluid.

The label can be configured to provide a Raman spectrum to a portable Raman spectrometer. In some embodiments, the capture molecule is a nucleic acid (e.g., DNA or RNA) molecule configured to bind to the biowarfare agent or a component thereof. At least one of the capture molecule and probe molecule can be an aptamer, antibody, or DNA molecule. The microbeads can have multiple capture molecules coupled thereto, and the multiple capture molecules can be the same. The microbead can have multiple capture molecules coupled thereto, and the multiple capture molecules can be different. The nanoparticles can be gold nanoparticles and can have one or more silver nanoparticles attached thereto.

The teachings of all patents, published applications and references cited herein are incorporated by reference in their entirety.

Certain definitions applicable to this disclosure are included herein.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

According to embodiments of the present disclosure, the operation of a breadboard for a system for detecting a target molecule can involve exposing a biological sample to a series of prepared biochemical treatments to extract DNA from the sample. The DNA can then be captured and labeled via specific chemistries attached to the surface of glass beads, which serve as transport media. Nanoparticles can form part of structures attached to glass beads. The beads can then be transported to be under a laser beam of a surface-enhanced Raman spectroscopy (SERS) sensor that produces a Raman spectrum that is unique to the Raman label associated with a gold nanoparticle probe designed to complement to a specific biological target, such as a nucleic acid molecule from a spore, bacterium, or virus. This unique SERS spectrum of the label corresponds only to the specific DNA detected, which is the basis for unambiguous detection and identification.

In some embodiments, following injection of the sample into a receiving vial, the breadboard lyses the sample chemically by mixing it with preselected enzymes and/or detergents to disrupt and dissolve cell walls and release the target DNA into solution. Alternative types of lysing can also be used, such as mechanical or thermal lysing. The DNA can then be collected and washed free of cell debris on silica gel contained in a glass capillary. Additional processing can also be performed, such as fragmentation with restriction enzymes. After lysing, purification steps can follow, e.g., before or after fragmentation. The DNA can then be removed from the silica gel and hybridized to the complementary DNA strands anchored (e.g., hybridized) to the surfaces of glass beads. The beads, with the target DNA attached, are then reacted (e.g., hybridized) with additional complementary DNA strands which are bound to organic dye molecules, or other labels, that are themselves bound to gold nanoparticles to give large SERS signals of the dye when analyzed. Additional enhancement can be achieved by reacting the bead-DNA-gold nanoparticle complex with an enhancing solution, which may contain gold or silver ions, for example. This solution will deposit gold or silver particles onto the pre-existing gold nanoparticles bound to the probe DNA. The SERS signal from the organic dye can be amplified by a factor of a million, for example, thereby providing excellent sensitivity and extreme specificity of the target DNA toward its complementary DNA, ensuring high selectivity for the target. Therefore, by detecting a specific organic dye by SERS, a specific biological target is detected.

Embodiments of the present disclosure can be used for a portable pathogen, e.g., biological warfare agent (BWA) sensor for use in the field, for example. Embodiments enable BWA samples, collected in the field, to be detected and identified in less than 30 minutes using new biochemistries, processing treatments, microfluidic devices, and detection methodologies. The organism-specific deoxyribonucleic acid (DNA), or ribonucleic acid, e.g., in the case of virus detection, can be extracted, processed, and detected with high sensitivity and selectivity. This can be achieved using random array analysis processes and detection using surface-enhanced Raman spectroscopy (SERS), according to embodiments of the present disclosure.

One implementation of embodiment devices is a field-use instrument designed specifically for Ebola detection. Based on testing an automated breadboard prototype described hereinafter, an Ebola detection device utilizing RNA processing chemistry is expected to be able to perform an analysis to detect Ebola within about 10 minutes.

The breadboard can be utilized to detect many different pathogens, proteins, and other biological targets. When used to detect a BWA target, for example, operation of the breadboard can involve the following example procedures. The BWA sample can be exposed to a series of mechanical and biochemical treatments to extract DNA from the target, which is then captured and labeled via specific chemistries attached to the surface of glass beads, which serve as transport media. The beads are then transported under the laser beam of a SERS sensor that produces a Raman spectrum that is unique to the BWA label. This unique SERS spectrum of the label corresponds only to the specific DNA detected which is the basis for unambiguous detection and identification. Following injection of a BWA sample into a receiving vial, the breadboard lyses the sample mechanically to disrupt cell walls and release the DNA of the BWA into solution. The DNA is then collected and washed free of cell debris on silica gel contained in a glass capillary. The DNA is then removed from the silica gel and chemically bound to complementary DNA strands anchored to the surfaces of glass beads. The beads, with the BWA DNA attached, are then reacted with additional complementary DNA strands, which are bound to organic dye molecules that are themselves bound to gold nanoparticles to give large SERS signals of the dye when analyzed. The SERS signal from the organic dye is amplified by a factor of about 1 million, thereby providing excellent sensitivity and extreme specificity of the agent DNA toward its complementary DNA ensuring high selectivity for the BWA target. Therefore, by detecting a specific organic dye by SERS, a specific BWA is detected. The prototype breadboard referred to above and described further hereinafter has been successfully used to detect *Yersinia pestis* (YP) (spore analyte), *Bacillus anthracis* (BA) (bacterial analyte), and Venezuelan equine encephalitis (VEE) (virus analyte), for example.

Example 2

FIG. 1A illustrates bead complexes 100*a* and 100*b*, which can be used in embodiments of the present disclosure for target DNA detection. The bead complex 100*b* includes a microbead substrate 102 coupled to a capture DNA molecule 104. A gold nanoparticle 106 is coupled to a probe DNA molecule 110 via a Raman dye 108. The probe DNA 110 is configured to be coupled to the capture DNA 104 via a target DNA molecule 112. The designations of the molecule 104 as the "capture" molecule and the molecule 110 as the "probe" molecule are arbitrary, as either molecule 104 or molecule 110 can be considered to perform "capture" or "probe" functions.

The bead complex 100*a* illustrated in FIG. 1A is similar to the bead complex 100*b* but also illustrates that the microbead 102 can be coupled to multiple capture DNA molecules 104. Furthermore, gold nanoparticles 106 can each be coupled to multiple probe DNA molecules 110 via Raman dye 108. FIG. 1B illustrates other possible embodiments of bead complexes. Nanoparticle use in detecting DNA and RNA molecules has previously been described in part in Y. C. Cao, R. Jin, and C. A. Mirkin, "Nanoparticles with Raman Spectroscopic Fingerprints for DNA and RNA detecting," Science, 297, 1536 (2002), the entirety of which is hereby incorporated herein by reference; and in U.S. patent application Ser. No. 10/172,428, filed on Jun. 14, 2002, the entirety of which is also incorporated herein by reference.

It should be noted that the bead complex 100*b* is referred to as a DNA bead complex or microbead complex because the capture DNA 104 and probe DNA 110 are configured to bind to the DNA target; however, the target can also be an RNA molecule or a protein, and the target and capture molecules be configured to bind to RNA or protein respectively, for example.

The Raman dye 108 can be other forms of labels as understood in the art of spectroscopy, such as a fluorescent dye (Alexa Fluor® 488 for example). Other bead complexes with other types of labels, such as fluorescence labels, can alternatively be used provided they can be identified by a spectrometer, thus identifying a probe DNA and target DNA to which they are attached. The microbead 102 and gold nanoparticles 106, with their respective DNA molecules attached, can be brought together in a reaction chamber (illustrated hereinafter in conjunction with FIG. 10, for example) or an assay mixing chamber to form the bead complex 100*b*. It should also be noted that the complex 100*a* in FIG. 1A has multiple capture molecules 104 coupled thereto, and the multiple capture molecules are the same, or homogenous. This can facilitate reaction with a target DNA in a fluid in a reaction chamber. In other bead complexes, the multiple capture molecules can be different sequences (ie heterogeneous) to allow a single bead complex to include different target molecules.

Gold (Au) nanoparticles 106 (e.g., 13 nm in diameter) modified with Raman-dye-labeled alkylthiol-capped oligonucleotide strands can be used as probes to monitor the presence of specific target DNA strands. There are over 100 oligonucleotide strands on each Au nanoparticle to ensure rapid and efficient bonding. The specific dyes chosen as the Raman labels exhibit large Raman cross sections.

In some embodiments, the microbead 102 is a substantially spherical glass microbead, but in other embodiments, other shapes and materials may be used.

FIG. 1C shows another embodiment of target hybridization and detection according to the systems, devices, and methods herein. A microbead 102 is coupled to one or more capture molecules 104 that can have identical or different sequences to form a microbead complex. A nanoparticle complex is formed by coupling a nanoparticle (silver or gold, for example) 106 to one or more probe molecules 110 (having identical or different sequences) through a dye 108, such as a Raman dye or other spectroscopic dye. The nanoparticle complex and the microbead complex then bind to a target molecule 112, such as a DNA molecule, creating a hybridized microbead complex. This reaction can take place in a reaction chamber or assay mixing module as described herein. The microbead complex can be mixed with silver or a silver solution containing silver ions or positively charged silver ions as well as a hydroquinone. A laser with an emission spectra approximately complementary or complementary to the absorption spectra of the dye 108 can then shine on the microbead complex, creating a SERS emission spectra which can then be analyzed.

Figure 1C:
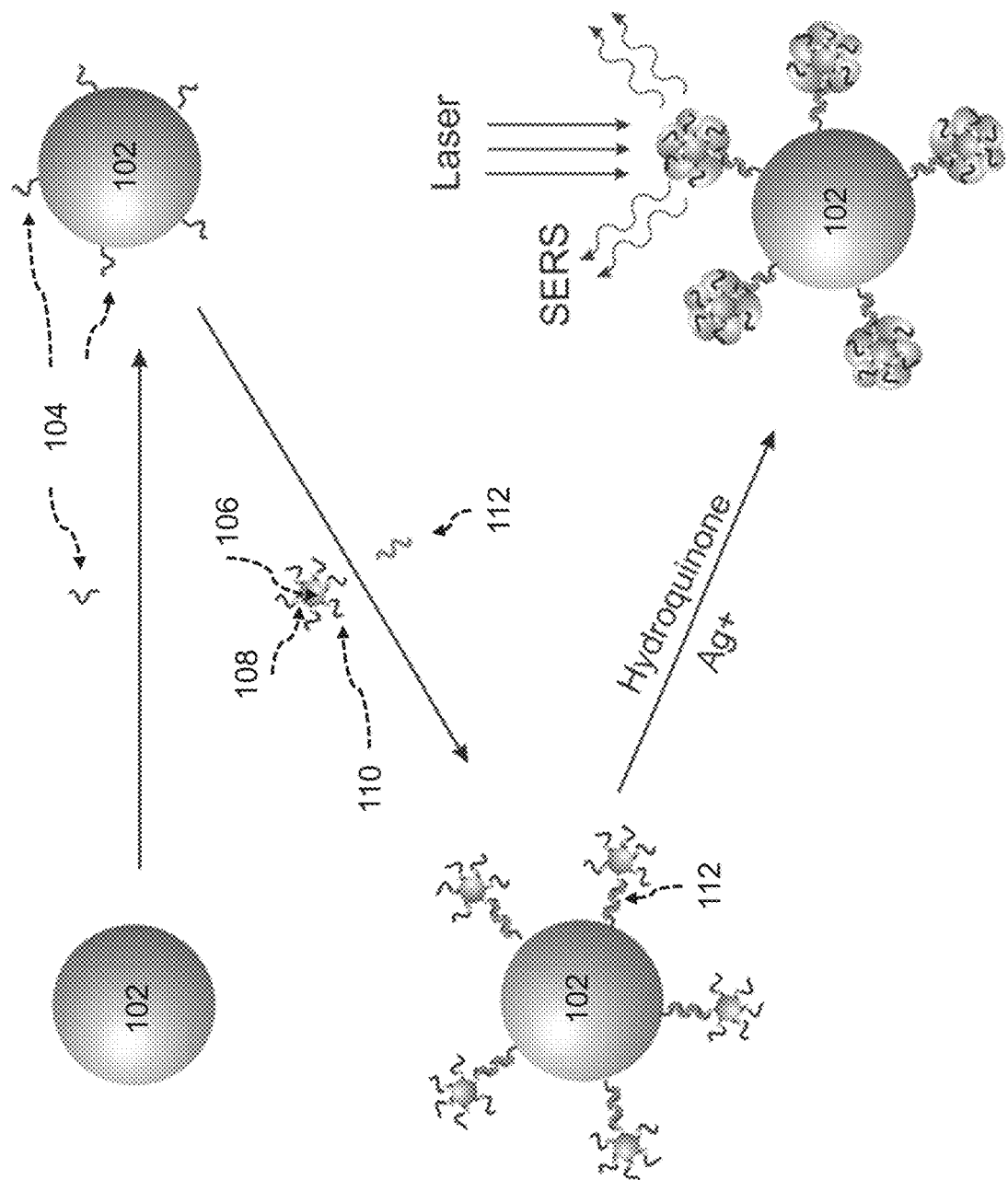
FIG. 1C illustrates an embodiment of microbead complex formation and SERS spectra generation according to systems, devices, and methods as described herein.

A "random array" design can be utilized, which is ultimately implementable on a microfluidic chip, whereby flowing glass beads containing the sandwich assay shown in FIGS. 1A-1C are passed through an analysis region, which can be the SERS optical probe area. This random array assay uses free floating probes in the assay instead of the stationary DNA strands on a substrate in a more conventional microarray. In this type of assay, batches of beads for different but specific targets are prepared. Reporter groups are used to identify the bead, the corresponding target, and whether or not a reaction with the target nucleic acid sequence has taken place. Incorporating the random array with a SERS-based reading system inherently assures a high degree of multiplexing by the use of multiple dye labeled nanoparticles and the well-defined Raman spectral features of the dyes. Useful attributes underlying the potential of the random array methodology include but are not limited to: fast hybridization kinetics—fast assay and rapid detection; simultaneous multiple assays in a single cartridge; SERS readout with fixed optical configuration; high reliability of field unit with no moving parts; mechanically robust bead storage in cartridge, small cartridge size by scaling only bead volume to add assays; inexpensive to produce; simple and easy-to-use self-contained assay cartridge.

These attributes ensure that the random-array detection system is exceptionally well-suited for the eventual development of a portable DNA-detection cartridge.

An embodiment of a method of DNA detection utilizing devices as described herein is as follows: after input of the sample (e.g., aqueous) containing the targets of interest, operation of a breadboard can be based on established laboratory scale procedures as follows:

Cell lysis by lysis buffer and DNA fragmentation by enzyme

Washing and separating DNA through the silica-gel membrane utilizing inherent silica affinity Transporting the target DNA to the mixing and capture chamber Injecting microbeads and nano-particle probes into to the mixing/capture chamber for circular flow mixing driven by the dielectrophoresis-pump (DEP) integrated below the chamber Incubation and capturing target DNA and nano-particle probes on microbeads with the aid of thermal cycling to achieve hybridization of the probes.

Washing

Flushing with silver (Ag) enhancement solution

Washing

Collecting the microbeads for SERS spectral analysis

Measuring SERS spectrum to detect and identify biological warfare agents present Useful considerations in the assay array implementation include:

Washing/flushing/cleaning. Efficient washing steps are helpful to ensure removal of unbound probes to avoid false positive results.

Probe selection. Unique Raman dyes can be selected for each probe so that detection occurs only in the presence of a specific target DNA.

Cell lysis. Bacteria cells can be lysed by mixing with a lysis solution.

DNA fragmentation. By injecting enzymes, the long ds-DNAs extracted from bacteria are fragmented into shorter pieces (such as less than 200 base pairs), which is useful for the hybridization of Raman-reporter particles. Similarly, long RNAs extracted from viruses are fragmented with RNA specific reduction enzymes, then treated similarly to DNA, as described below.

DNA separation. By filtering through a silica-gel membrane, the DNA fragments are absorbed onto the membrane in a high-salt buffer solution. After washing, the fragmented bacterial DNA are released and collected from the membrane using a low-salt buffer solution.

Hybridization. The chemistry for the hybridization of Raman-reporting particles with bacterial DNA targets onto the beads is a core of the assay. To achieve high-sensitivity and high-selectivity detection, this chemistry can be optimized via (a) detailed design of locked nucleic acid (LNA) or peptide nucleic acid (PNA), (b) the choice of Raman reporting dyes, (c) the size of gold nanoparticles for the probes, (d) the size of the random array supporting beads (e) the chemistry to functionalize the LNA probes onto these beads, and (f) the hybridization conditions such as temperature, buffer solution, and hybridization time.

The YP cell lysis and DNA extraction protocol optimization was performed by focusing on using the Qiagen DNeasy® blood and tissue kit. After experimentally determining this kit as the most successful commercially available kit, work was performed to optimize the DNA yield. In this protocol, an aliquot of a known number of cells was isolated to be lysed. Cell lysis buffer and Proteinase K was added to the cells, which were then resuspended and incubated in a water bath. Following incubation, RNase A was then added to the lysis solution. An additional lysis buffer was added to the solution to finish the lysing and digestion reactions. Ethanol was then added to the solution to precipitate genomic DNA from the solution. The solution was transferred to a silica-membrane spin column, where it was washed with two different buffers and eventually eluted from the column. The resulting material was then measured by UV-Vis spectrophotometry to determine the DNA yield.

The treatment of Gram-Positive bacteria, like BA, was slightly different from the Gram-Negative procedures for the lysis and DNA purification of YP. In order to lyse the cell wall of BA, an enzymatic lysis buffer comprising 20 mM Tris-Cl pH 8.0, 2 mM sodium EDTA, 1.2% Triton® X-100 and 20 mg/mL lysozyme from chicken egg white was first prepared. This lysis buffer is sufficient for breaking the cell walls of Gram-Positive bacteria and spores because of the aggressive lysozyme and the detergent components. After an appropriate number of cells (here, ~1×107) were harvested, they were centrifuged into a pellet and the supernatant was discarded. The bacterial pellet was then resuspended in 180 μL of the previously described enzymatic lysis buffer and then incubated at 37° C. for at least 30 minutes. 25 μl of Proteinase K and 200 μl of Buffer AL was then added and mixed through vortexing. The reaction tube was then incubated at 56° C. for 30 minutes, causing lysis of the BA cells and allowing for extraction of the BA DNA. After incubation, 200 μL of ethanol was added to begin DNA precipitation. The reaction was mixed till homogeneous by vortexing. The mixture was then transferred onto the Silica gel of a Qiagen DNeasy® Mini Spin Column in a 2 mL collection tube. DNA selectively attached to the membrane, driven by the high concentration of chaotropic salt. The mixture was then centrifuged at 8000 rpm (6,046 g) for 1 minute. The DNA remained adhered to the silica gel and the flow-through is discarded. The column was then placed in a new 2 mL collection tube and 500 µL of buffer AW1 was then added to the column and then centrifuged at 8000 rpm (6,046 g) for 1 minute. Again, the flow-through was discarded and 500 µl of buffer AW2 was added to the column. This was then spun down at 13,000 rpm (16,060 g) for 3 minutes in order to dry the silica gel membrane. Flow-through was again discarded and the column was placed in a clean collection tube.

At this point, clean DNA remained attached to the silica gel membrane. It was then eluted with 200 µL of Buffer AE added to the spin column; this buffer has a low salt concentration. After 1 minute of incubation at room temperature the column was spun at 8000 rpm for 1 minute. The flow-through was then collected and measured by UV-Vis spectrophotometry for DNA content. This process was repeated several times, and each repeat yielded about 50% of BA DNA as determined by UV-Vis spectrophotometry.

Example 3

Figure 2B:
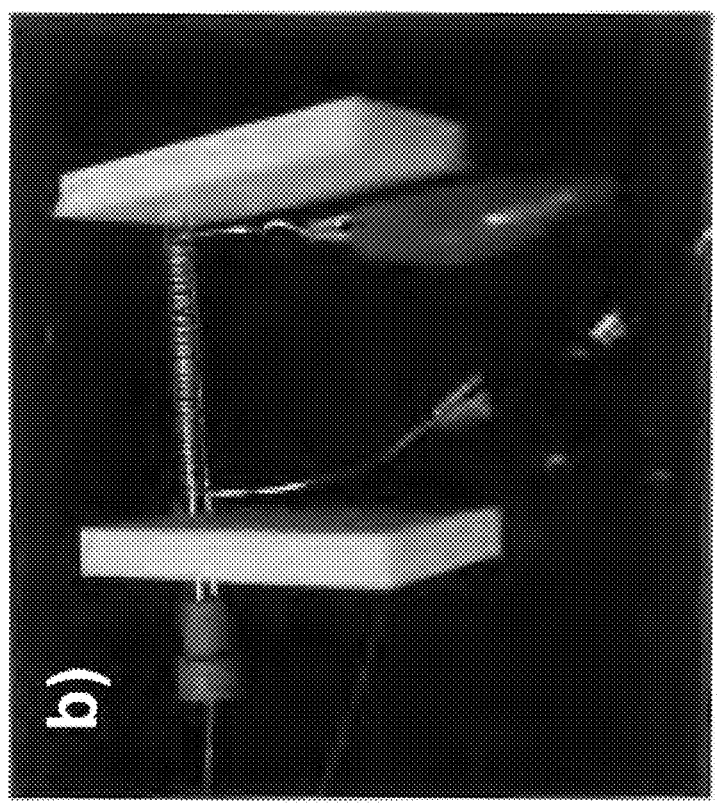
FIGS. 2A and 2B illustrate an in-line capillary heater for cell lysis.
Figure 2A:
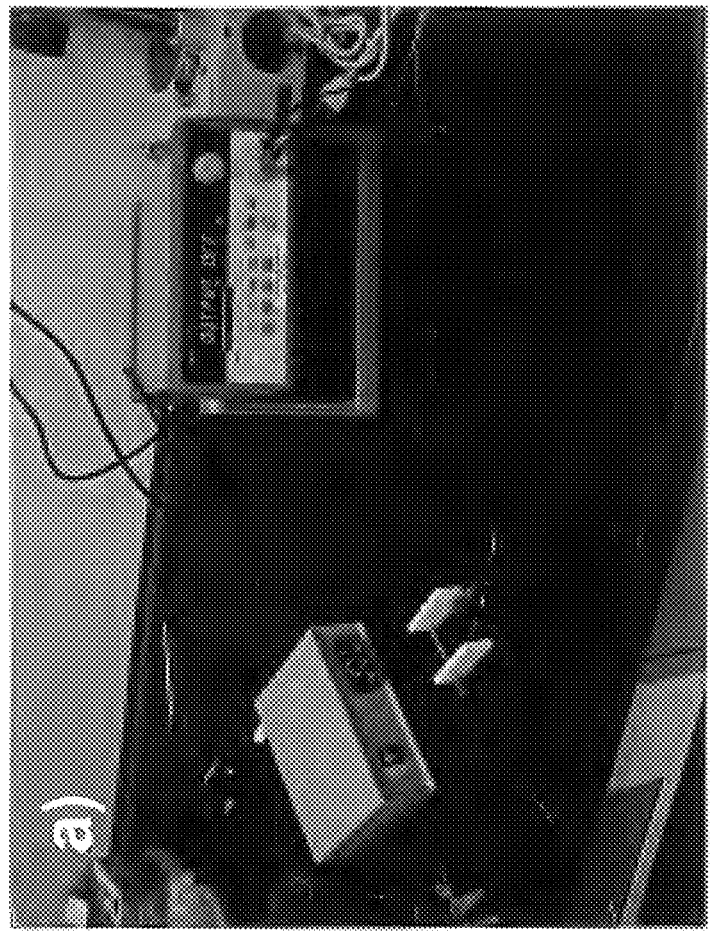

FIGS. 2A and 2B illustrate an in-line capillary heater for thermal cell lysis. In the device of FIGS. 2A-2B, heating can be achieved by applying 3.0 VDC and 1.0 amps to 24 gauge nichrome wire coiled over a 4 mm OD (2 mm ID) quartz capillary. A thermocouple to monitor the liquid temperature is inserted into the capillary from the left in FIG. 2B.

Figure 3C:
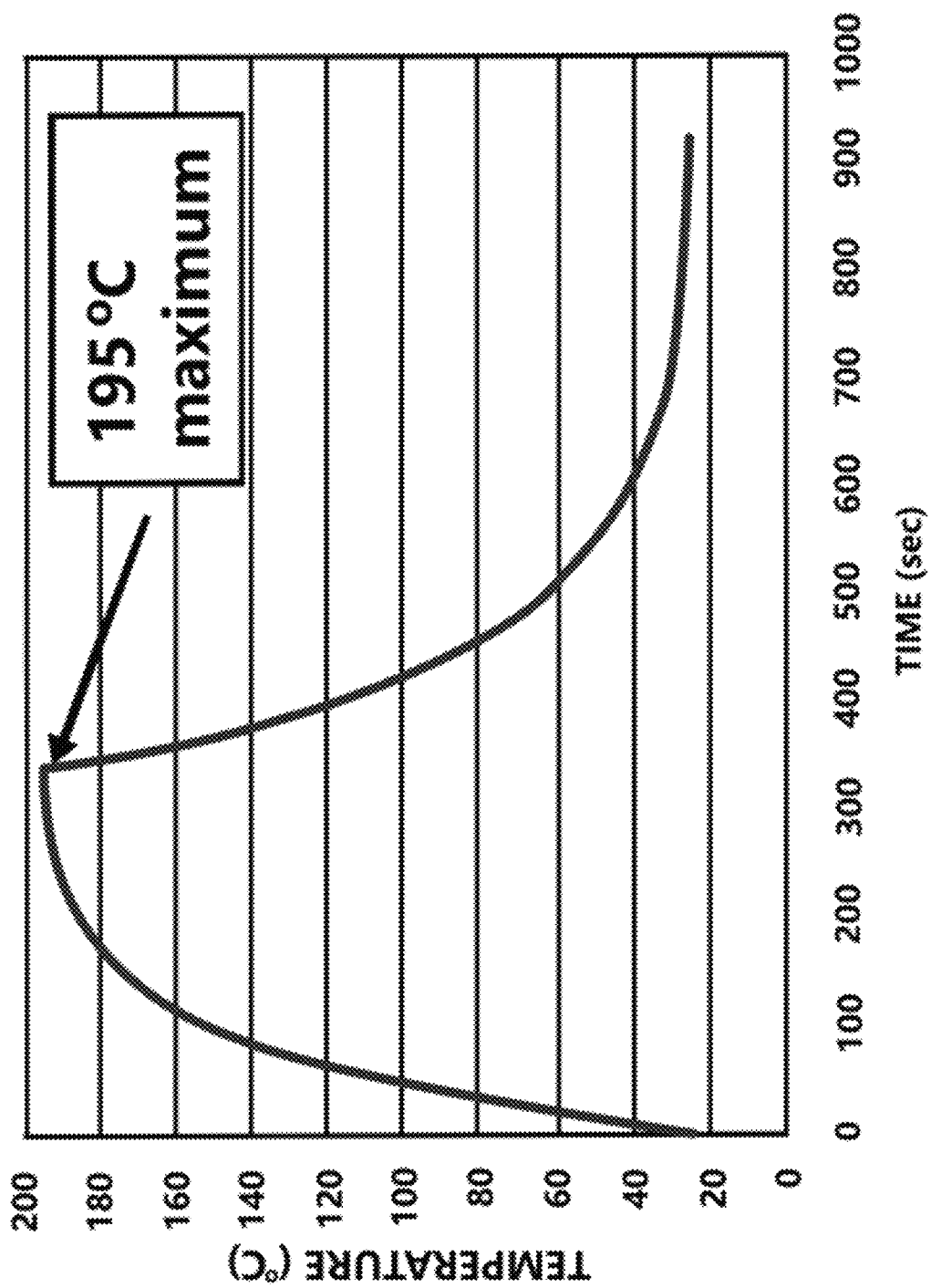
FIG. 3C is a graph showing a temperature profile of the solution of FIGS. 3A and 3B during heating and cooling.

In order to minimize the analysis time for this application, ways were explored to minimize the time required for each processing step. The enzyme-based cell lysing method can be replaced with a more time efficient thermal lysing procedure. In this method, lysing is achieved by simply passing the liquid cell suspension sample through a capillary heated to between 95° C. and 200° C. If successful, the cells should lyse and the cellular debris dissolve, releasing the cell's DNA for subsequent capture and purification. To test this method, a heated capillary was built by coiling 24 gauge nichrome wire (60% Ni, 12% Cr) around a quartz capillary as shown in FIGS. 2A-2B. The nichrome wire was heated with a DC power supply providing 3.0 VDC and 1.00 Amps. A thermocouple was inserted into the capillary to monitor the sample temperature. The capillary was filled with a solution of BA spores at a concentration of $2 \times 10^8$ cells/mL. After filling the capillary, power was applied to the nichrome wire. FIGS. 3A-3C illustrate successful completion of this test, showing successful lysis and dissolution of cellular debris.

FIGS. 3A-3B show micrographs of BA spore solution before and after heating the temperature through a temperature profile shown in FIG. 3C with the device of FIGS. 2A and 2B and with maximum temperature of 195° C. Efficient spore lysis of greater than 95% is indicated by near absence of spores remaining after heating sample, as seen in FIG. 3B. The capillary in FIGS. 2A-2B containing the BA spore solution was heated with the temperature profile shown in FIG. 3C. These results show that efficient cell lysing can be performed on a microfluidic platform even for cells and material that is resistant to traditional lysis methods, such as difficult-to-lyse BA spores.

Example 4

Initially, experiments were conducted on YP detection using synthetic double-stranded DNA (ds-DNA). Results demonstrated the successful SERS detection of YP at a ds-DNA concentration of 0.1 nM through the random array detection format. In this work, an alkylthiol-capped, Cy3-labelled oligonucleotide probe (for binding onto gold nanoparticles), an alkylthiol-labeled oligonucleotide probe (for binding onto silica particles), a 44-mer double strand DNA target as a positive control: 5'-GTG AGA GTA GGA TCA TAT ACC GTT AGA TGC TGC TGG CGT TAT G-3' (SEQ ID No. 1) (the sequence is determined in accordance with the information from *M. Guelta: Y. Pestis* genes GenBank: X61996), and a 44-mer negative control: 5'-GTC ACT CTA GGA TCA TAT ACC GTT ACT TCG ACG TGG CGA TAT G-3' (SEQ ID No. 2) were designed. A method for synthesizing 13-nm diameter gold nanoparticles has also been established.

Gold nanoparticles functionalized with Cy3-labelled oligonucleotides were prepared as SERS probes. The resulting nanoparticles were shown to be stable in phosphate-buffered saline (0.6 M NaCl). UV-Vis spectroscopy showed that these particles exhibit a characteristic surface plasmon band of monodispersed gold nanoparticles, a result that was further confirmed with transmission electron microscopy. All together, these results show that the synthesis of DNA-capped gold nanoparticle probes is very successful. Oligonucleotide-functionalized glass beads (100 micron in diameter) were also successfully prepared.

Data have confirmed that the random-array assay can give rise to strong SERS signals in the presence of the 44-mer double-stranded synthetic DNAs (5'-GTG AGA GTA GGA TCA TAT ACC GTT AGA TGC TGC TGG CGT TAT G-3' (SEQ ID No. 1)), but not in the presence of the negative control DNAs (5'-GTC ACT CTA GGA TCA TAT ACC GTT ACT TCG ACG TGG CGA TAT G-3 (SEQ ID No. 2)), for example. It should be noted that the sequences given above can, alternatively, be expressed with a "C" or "C—" marker near the middle of the sequence as a visual demarcation between the half of the target that binds to the probe sequence and the half that binds to the capture sequence. This visual identifier has been removed, and the sequences given above are shown without demarcation.

The stability of Cy-3-labelled DNA-gold nanoparticle probes in a PBS buffer has been tested. Results have shown that the samples are stable at 4° C. (~7 weeks) and stable at room temperature for more than 10 days.

Oligonucleotide-functionalized glass beads (30 micron in diameter) as a YP-DNA assay have been successfully prepared. Samples were made from YP-DNA assay at the DNA-target concentration of 1 nM (synthetic DNA). 13-nm gold nanoparticle probes were functionalized with Rhodamine 6G dye (R6G)-capped probe DNA, and 30-micron glass beads were functionalized with capture DNA. After incubation of YP-DNA targets, gold-nanoparticle probes, and functionalized glass-beads in a PBS buffer (0.3 M NaCl) for 30 min, the sample was washed with PBS buffer, and then silver coated on the surface of the glass beads where gold nanoparticles were present due to the YP-target binding. The resulting beads were further washed with PBS buffer and were used for SERS measurements using microRaman.

Results from initial stability tests conducted showed that Cy-3-labelled DNA-gold nanoparticle probes were stable in a PBS buffer (0.3 M) for 38 days at room temperature, while it was found that aggregation of gold nanoparticles occurred in the sample stored at 4° C. for 11 weeks. Nanoparticle aggregation was found to be a reversible process and the aggregates can be re-dispersed in PBS buffer at room temperature. This positive result suggests that keeping these nanoparticles at room temperature might be a good condition for nanoparticle storage.

Optimizing the YP DNA assay using the 30-micron glass beads continued. The total DNA hybridization time of the assay was 50 minutes. After silver staining, very strong SERS signals from Cy3 labels were obtained using a micro-Raman spectrometer. The assay time can be decreased significantly by increasing the salt concentration of PBS buffer.

A new double helix DNA for YP was prepared. Since real samples of YP will contain double stranded DNA (ds-DNA) and not single strand DNA as has been used previously, this synthetic ds-DNA will be used in future experiments to establish and optimize the best DNA chemistry for the cartridge. Test results have shown that the DNA-gold nanoparticle conjugates for YP detection are stable for four and half months.

New probes were designed for the program analytes BA, and VEE. These designs include capture DNA to be bound to glass microbeads, target DNA, and probe DNA containing gold nanoparticles and Raman dyes. The DNA probe strands, capture strands, and target strands for BA and VEE were obtained from Bio-Synthesis Inc. The sequences for all DNA used in this program are listed hereinafter.

Figure 4:
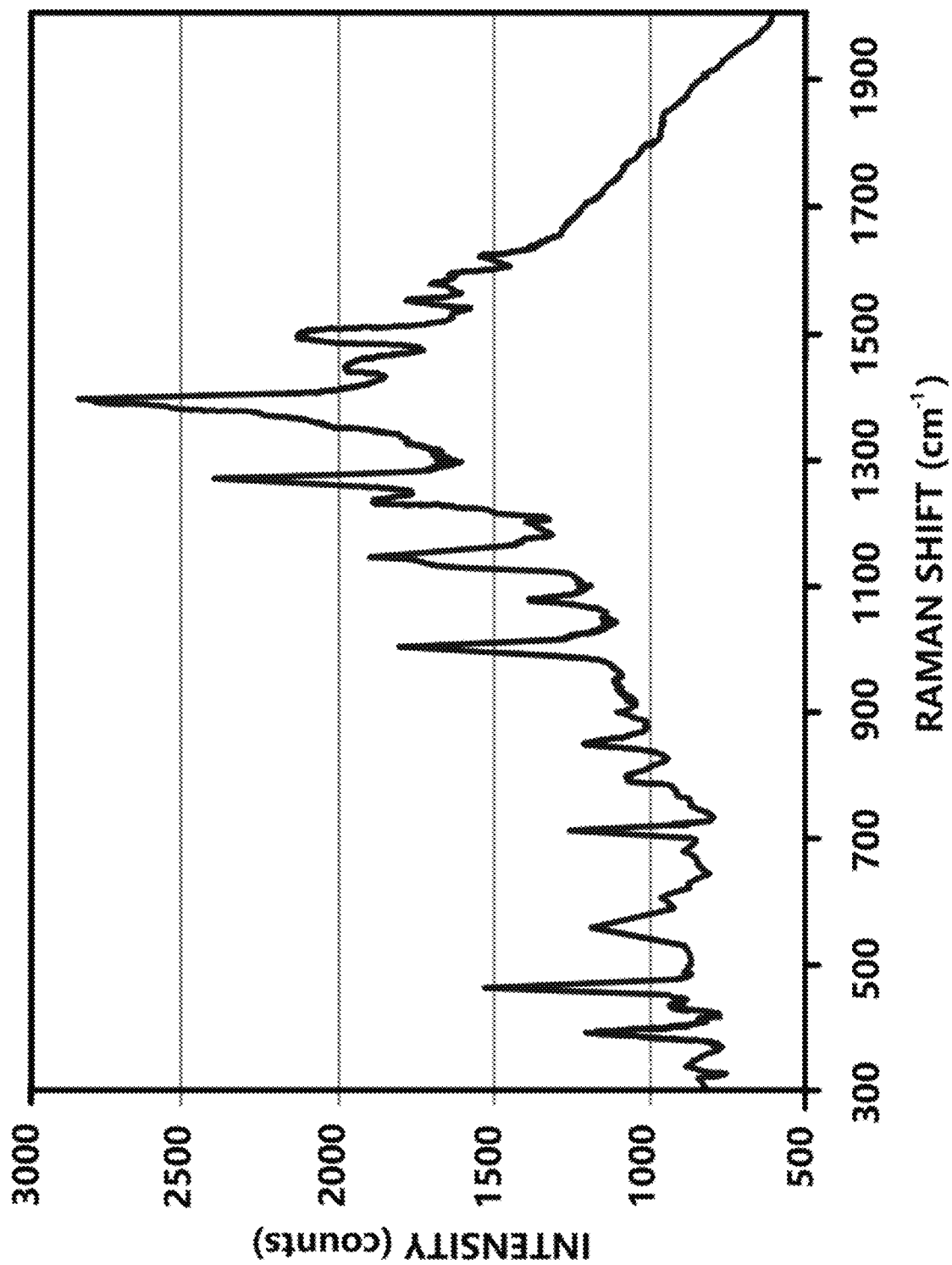
FIG. 4 is a graph showing an SERS spectrum of cyanine dye Cy3 detected from a *Yersinia pestis* (YP) assay.

FIG. 4 shows a SERS spectrum of Cy3 detected from a YP assay.

This spectrum was the result of successfully integrating and performing 1) preparing the surface of 30 μm diameter glass beads 2) binding the YP capture DNA (c-DNA) onto glass beads, 3) deprotecting, purification, and binding of the YP probe DNA to 13 nm diameter gold nanoparticles (p-DNA), 4) preparation of the YP target DNA (t-DNA), 5) mixing of the c-DNA, p-DNA, and t-DNA for 25 minutes, and 6) treatment of the sandwich structure with silver staining solution. (c-DNA, p-DNA, and t-DNA as used herein can refer to capture molecule DNA, probe molecule DNA, and biological target DNA respectively).

The SERS-bead assay process was tested and optimized. Initially, the process was carried out using conventional/manual laboratory processes and equipment (i.e., glass vials, orbital shaker, pipets, etc.). All assays have been performed using YP-Target-FW ("FW" denotes "forward") as the target DNA sequence, which is complementary to the YP-capture and YP-probe sequences. Reaction volumes were ~2 mL. After the benchtop assays were deemed successful (determined when the Cy3 signal could be reliably detected on individual beads), the assay was transferred to the breadboard described hereinafter in conjunction with FIGS. 16A-B for automated processing. Strong absorbance at 260 nm due to DNA absorption indicates recovery of an amount of the YP DNA contained in the YP cells supplied by the Edgewood Chemical Biological Center (ECBC) that will be sufficient for analysis.

Example 5

Figure 5B:
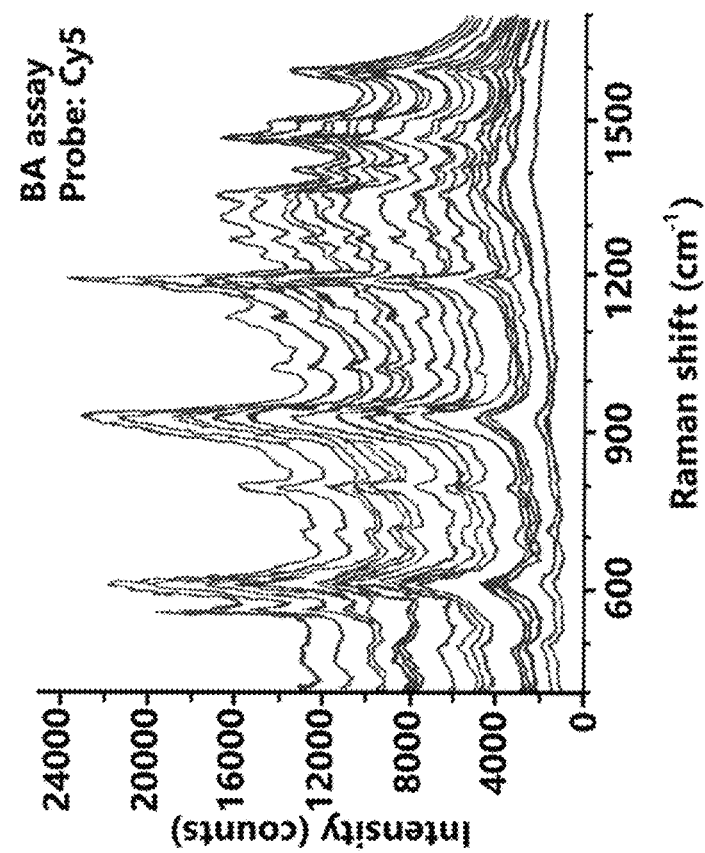
FIGS. 5A and 5B are graphs illustrating SERS spectra collected for assays of Venezuelan equine encephalitis (VEE) and BA, respectively.
Figure 5A:
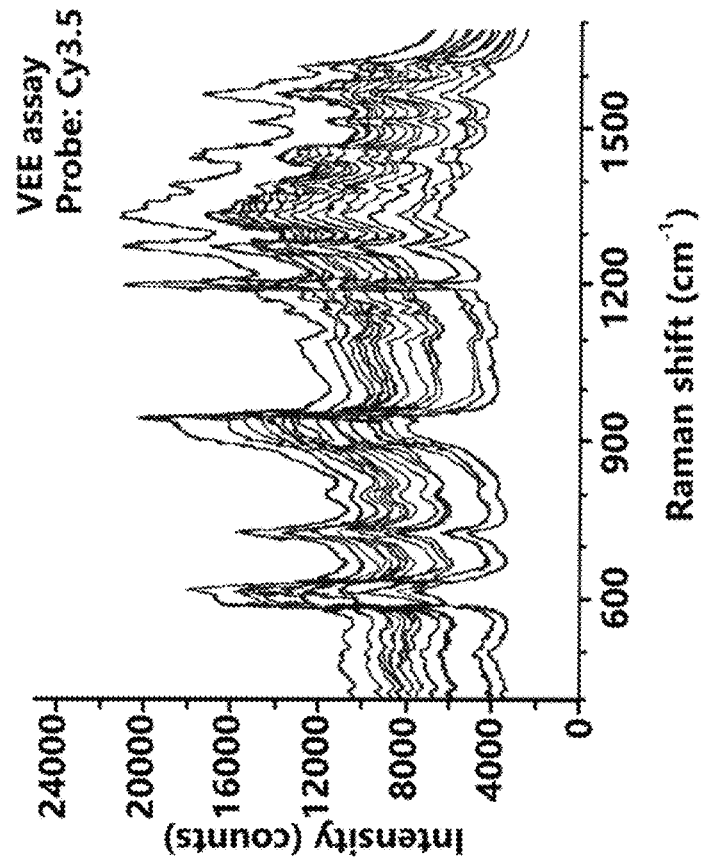

FIGS. 5A and 5B are graphs illustrating SERS spectra collected for assays of VEE and BA, respectively. Twenty beads were measured following each assay, and each collected spectrum is shown. Building on previous work that successfully demonstrated the assay chemistry for YP in the laboratory and on the breadboard of FIGS. 16A-B, assay chemistries for the analytes BA and VEE were implanted. By following the same stepwise chemical processing procedure developed for YP to bind the capture, target, and probe DNAs onto glass beads, strong SERS signals for both BA and VEE were observed. Note that the probe dye for VEE is Cy3.5 and the probe dye for BA is Cy5. As shown in FIG. 5, very strong SERS signals were measured on nearly all beads for both assays, indicating that the efficiency of the chemistry is quite good. It is also observed that the SERS spectra from the probe dyes Cy3.5 and Cy5 are sufficiently different in spectral features to allow ready differentiation between analytes using these two dyes as probes. The integration time for the SERS measurements on each bead was only 10 seconds, indicating that strong SERS signals can be obtained using short measurement times for these well designed assay probes.

Figure 6:
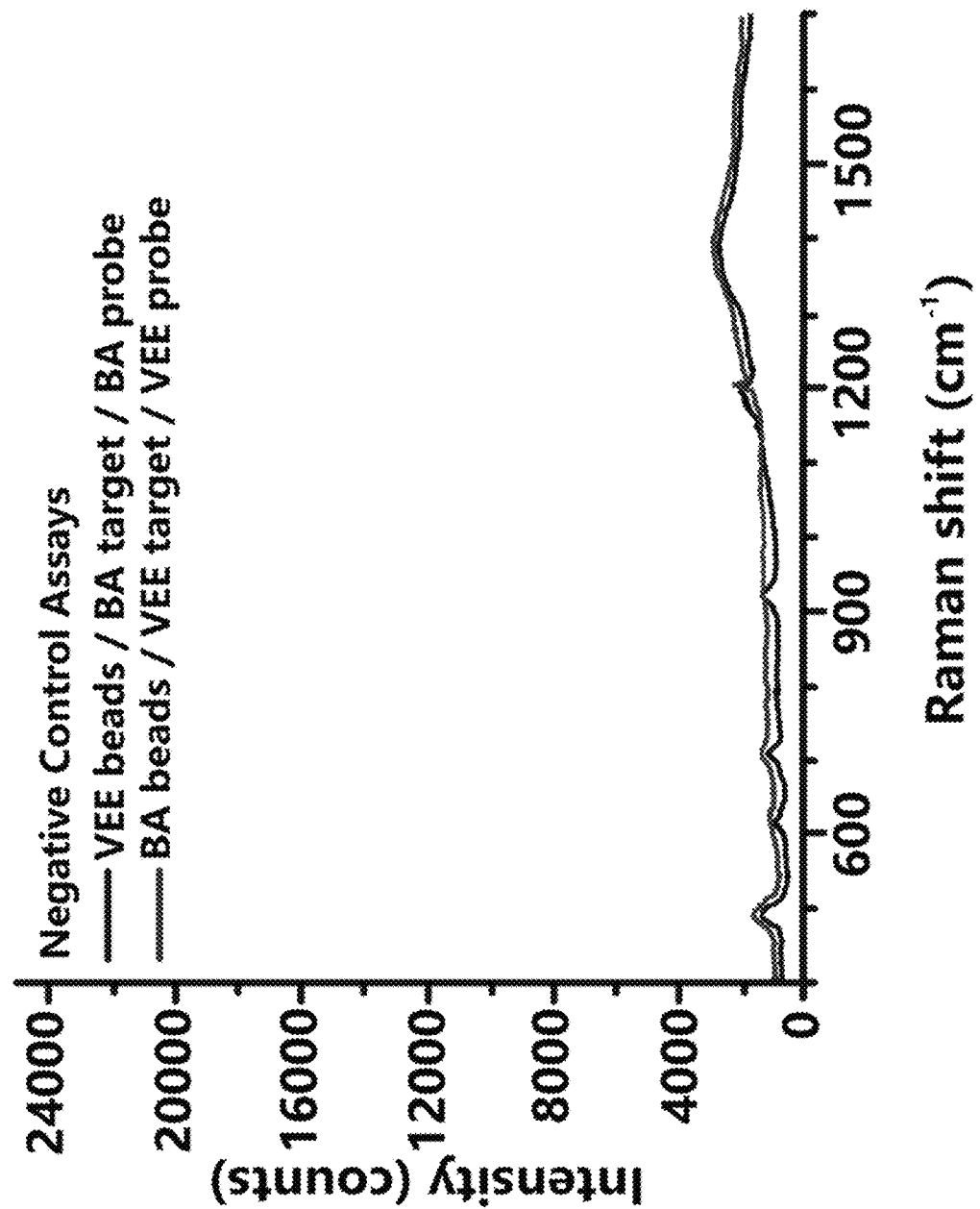
FIG. 6 is a graph illustrating SERS spectra collected from VEE and BA negative control assays.

FIG. 6 shows SERS spectra collected from VEE and BA negative control assays. Twenty beads were measured following each assay, and each collected spectrum is shown. To demonstrate the selectivity of the BA and VEE assays, negative control experiments were conducted wherein the BA assay was run with VEE target DNA and the VEE assay was run with BA target DNA. Strong SERS signals would not be expected on any of the beads. This is, in fact, the observation as shown by the SERS spectra collected from these negative control assays in FIG. 6. All of the spectra in FIG. 6 are weak in intensity and are readily distinguishable from the positive spectra in FIGS. 5A and 5B. The low intensity spectral features in the spectra can be attributed to residual probe material after washing and not to nonspecific binding of probe DNA. The broad spectral feature in many spectra that is centered at 1400 cm-1 is associated with the glass beads themselves.

The improved breadboard can be designed to handle and process 10-20 times less sample volume, typically approximately 50-200 than the benchtop procedure. Automated mixing/reacting of the capture beads, target DNA, AuNP-probes (gold nanoparticle probes), Ag-development solution, and Cl⁻ solution (with intermediate washing steps) was then accomplished without involvement from the user. The entire current process for YP (un-optimized) is timed to be approximately 30-40 minutes. After the beads have been processed, they are pipetted out of the breadboard reaction tube, and transferred to a quartz microscope slide for analysis.

For each assay, the SERS signals of 20 beads are randomly measured. Measurement parameters are constant at 100 mW and 10 s integration time using a 50× microscope objective. Most assays were performed using 1-10 nM of target DNA. In these cases, only ~1-5% of the beads produced a sufficient Cy3 signal. Assays to determine the capture beads' binding capacity were also performed; this was accomplished by first treating the capture beads to an excess of target DNA. After thorough washing, the beads are reacted with AuNP-probes and then treated with Ag-development solution. Finally, the beads are treated with Cl— buffer to enhance the SERS response. At these high concentrations of target DNA (~1 μM), the beads produce approximately the same signal as the beads treated with ~1 nM target DNA, i.e., only ~1-5% of the beads produce a measurable Cy3 signal.

Example 6

Figures 7A, 7B:
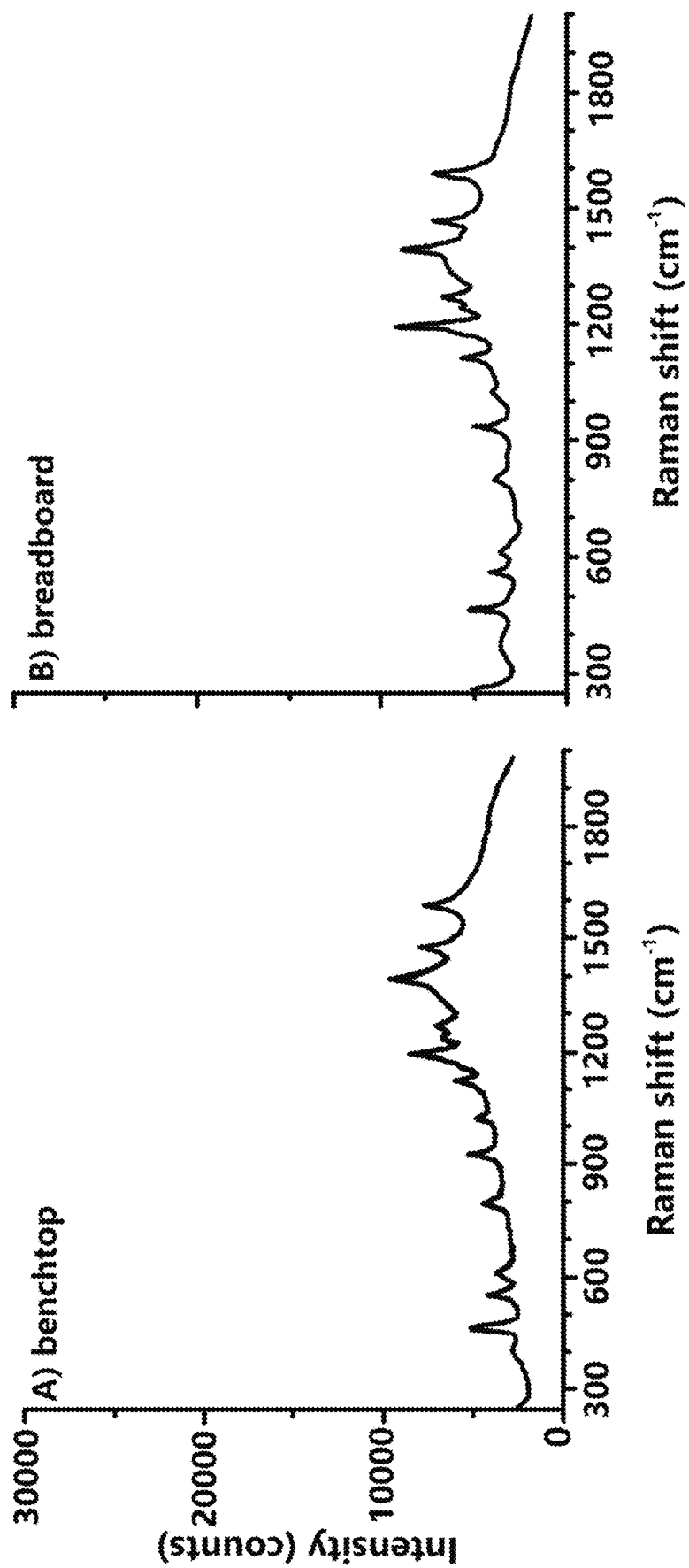
FIG. 7A is a graph illustrating SERS measurements on benchtop YP assays using a 1 mM YP target.
FIG. 7B is a graph similar to the graph in FIG. 7A, except breadboard YP assays were measured.

FIGS. 7A and 7B show similarity between A) benchtop and B) breadboard YP assays, respectively, using 1 μM YP target. Twenty beads were selected randomly and measured for each assay.

SERS Cy3 spectra of 20 randomly selected beads processed on the benchtop and breadboard are shown. The data show that the assay on the breadboard can be as good as or better than the benchtop assay, demonstrating the effective automation of the assay. The intensity scale is fixed at a maximum of 30,000 counts for comparison with data presented later in this document.

Figures 8A, 8B:
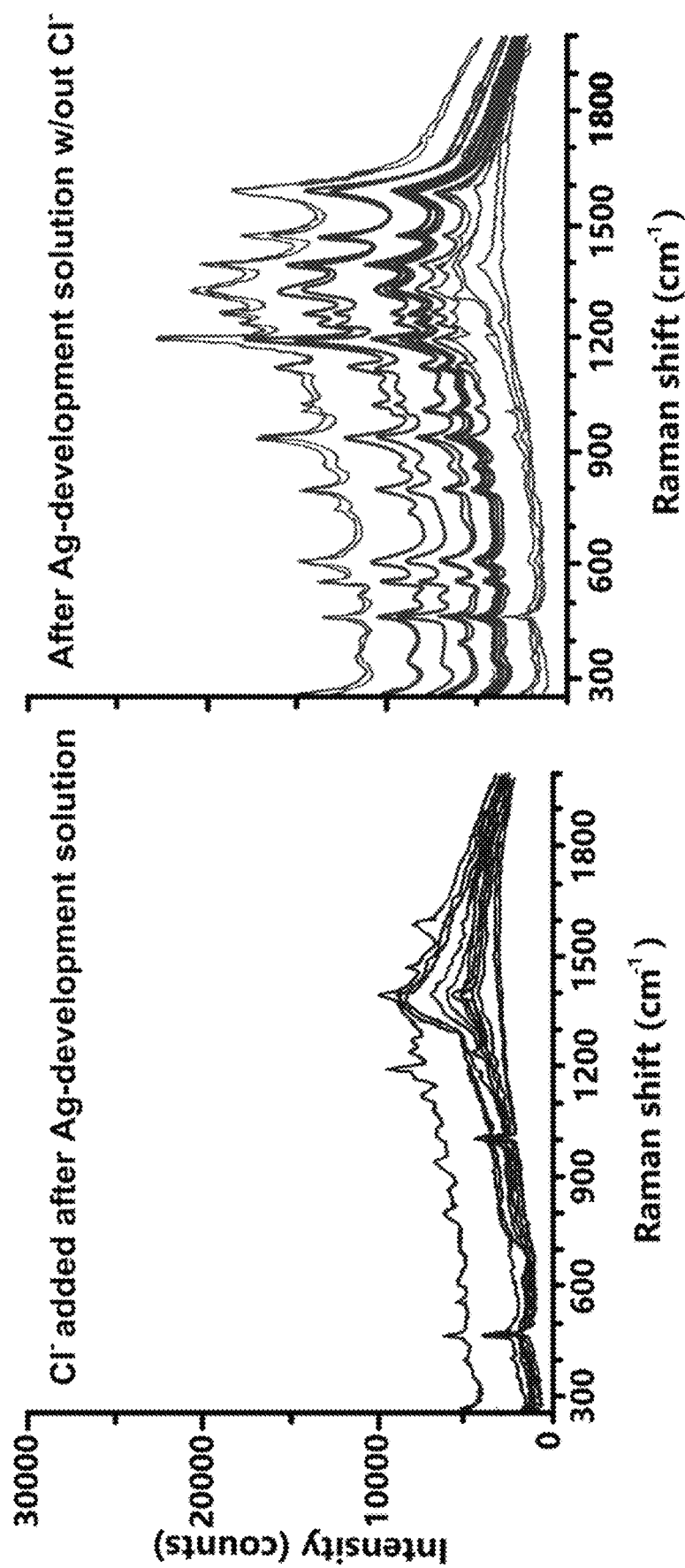
FIGS. 8A and 8B are graphs illustrating and SERS measurements on 20 randomly selected, fully reacted beads with and without, respectively, the final Cl— treatment. These figures illustrate a strong increase in Cy3 SERS signals when the final Cl— treatment is eliminated.

FIGS. 8A and 8B shows SERS measurements on 20 randomly selected fully reacted beads with A) and without B), respectively, the final Cl⁻ treatment. By eliminating this final Cr treatment, the percentage of beads producing a strong Cy3 SERS signal increased from 1% to 75%. This demonstrates one way that the automated assay protocol can be optimized. It was found that the final Cl⁻ 'activation' step actually impeded the SERS response of the beads. By eliminating the use of Cl⁻ treatment, the number of beads that produced a strong Cy3 SERS spectrum increased from 1% to 75%. It was found that the final Cl⁻ treatment caused the silver coating to detach from the beads and agglomerate into clumps. The removal of the silver coating from a bead drastically reduced the SERS signal the bead produced.

Example 7

Figures 9A, 9B:
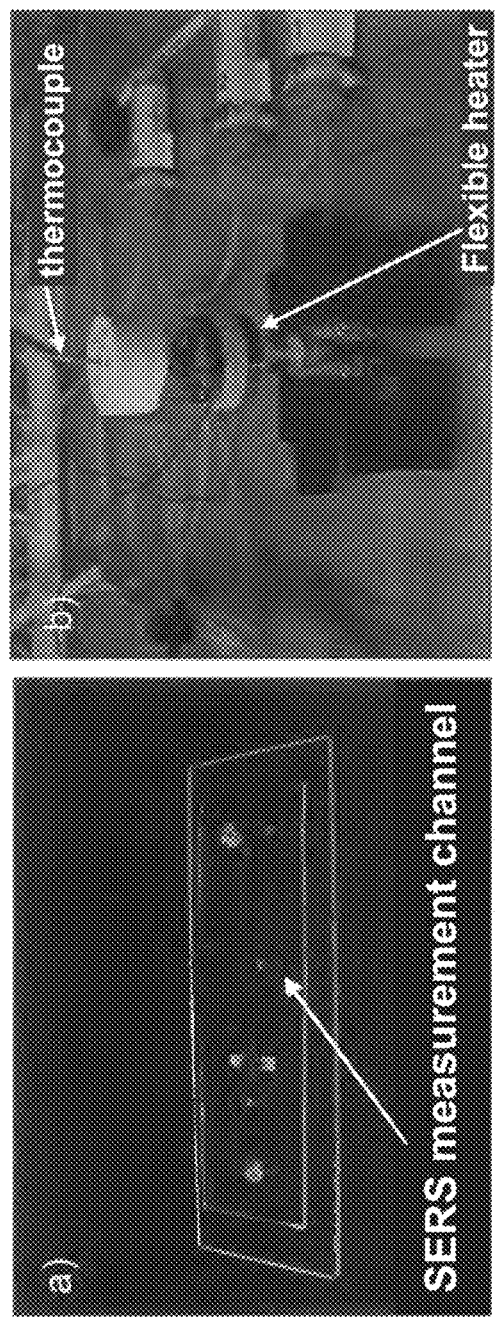
FIG. 9A illustrates a microfluidic channel used to improve the breadboard for all SERS measurements.
FIG. 9B illustrates a heated mixing chamber that accommodates cell preparation chemistry to improve the breadboard.

FIGS. 9A and 9B illustrate additional breadboard or system features, namely a microfluidic channel that can be used for SERS measurements (FIG. 9A) and a heated mixing chamber to accommodate cell preparation chemistry (FIG. 9B). To simulate SERS spectra collection from a microfluidic chip, a channel (70 µm×3 mm) was fabricated using PDMS and a quartz microscope slide as shown in FIG. 9A. Inlet and outlet ports allowed glass beads, prepared with our assay chemistries, to be injected to fill the channel with a transfer pipette. This filling method simulated the filling of a channel on a microfluidic chip. Once the beads are placed in the channel, the entire assembly was placed on the microscope stage of a PeakSeeker™ Raman system for measurement. Since the beads were stationary in this case, each bead was translated to be positioned under the Raman laser beam for measurement, allowing for the collection of the 20 SERS spectra reported above from individual beads. All SERS spectra in FIGS. 7A-8B were collected using this microfluidic channel assembly. Also, in order to transition the lysing chemistry to the breadboard, a heated mixing chamber was built, as shown in FIG. 9B. The heated chamber maintained a temperature of 50-95° C. to denature all target DNA to single strand and to prevent nonspecific binding by probe DNA. The heating chamber in FIG. 9B can be configured for conventional thermal cycling according to known protocols and parameters of nucleic acid binding to assay in optimization of the assay. The heating chamber of FIG. 9B can be a thermal cycler.

Example 8

Design of Cell Lysis and DNA Extraction Functionalities of Breadboard A strategy has been developed to implement automated cell lysis and DNA extraction on a system, device, cartridge, and/or breadboard unit. The basic processing principles are an extension of the microbead-based assay shown in embodiments in FIGS. 1A-1C and described throughout; therefore, the use has been extended of this successful design paradigm (e.g., computer-controlled syringe pumping, programmable miniature electro-fluidic valves, Teflon capillary fluid handling, miniature glass mixing/reaction tubes, etc.) to also include cell lysis using the lysing chemistry, which includes DNA extraction and purification via a silica-gel-filled capillary.

Figure 10:
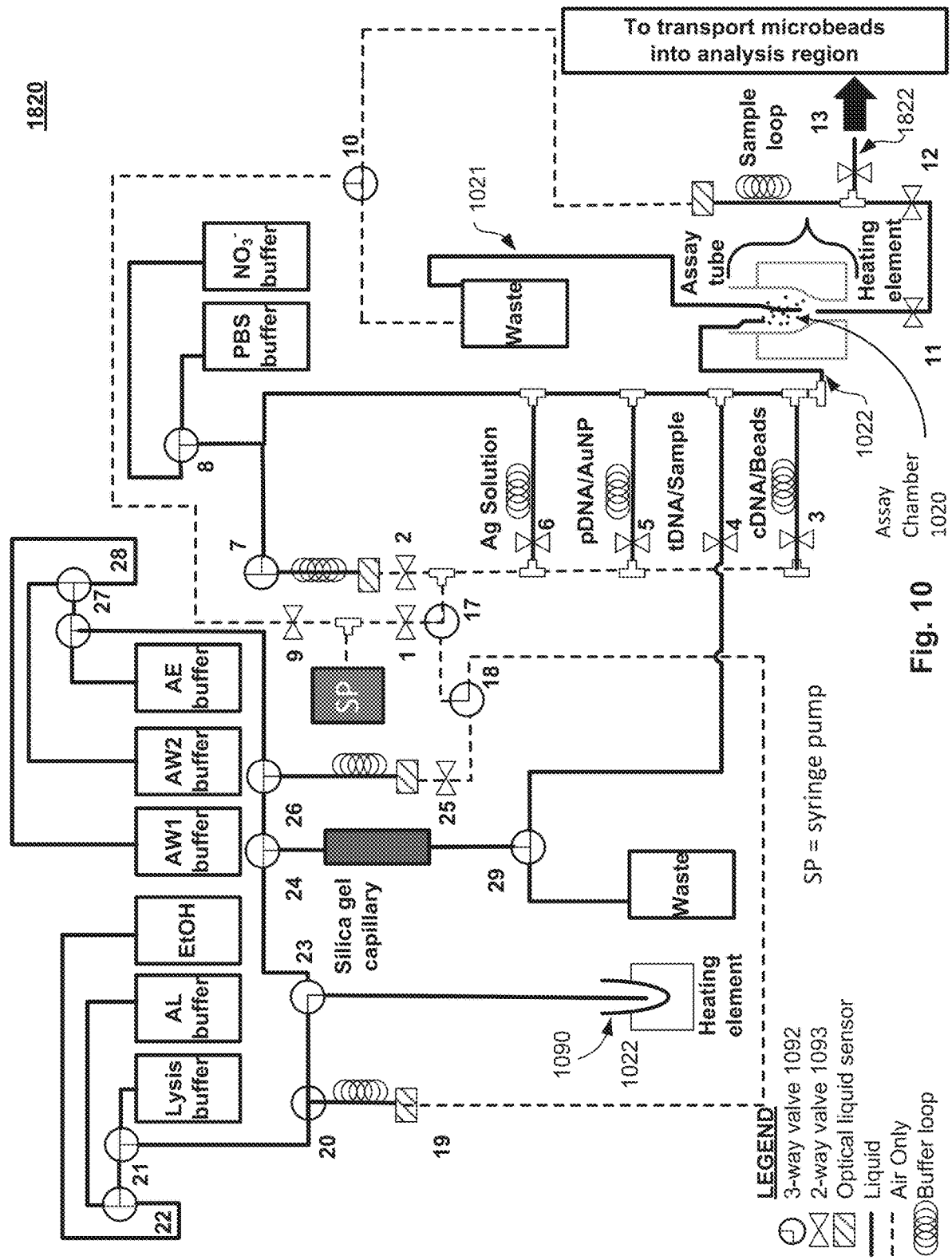
FIG. 10 is a schematic diagram illustrating an expanded breadboard including cell lysing and silica gel DNA extraction.

FIG. 10 shows a schematic diagram illustrating an embodiment of a hardware configuration to incorporate example functionalities. Multiple embodiments of the configuration in FIG. 10 can be realized, for example on a breadboard or self-contained microfluidic cartridge coupled to a controller and/or computing device. The additional components do not increase the foot-print of the current breadboard, so additional large equipment (e.g., power supplies, syringe pumps, etc.) is not expected to be needed.

The breadboard of FIG. 10 includes various three-way valves 1092 and two-way valves 1093 to control flow of fluid (ie restrict and/or direct among others) between different chambers of the breadboard, such as between the lysing chamber 1090 and an assay chamber 1020. The assay chamber 1020 is the part of the reaction chamber 1820 where nanoparticle complexes and microbead complexes as described herein (embodiments shown in FIGS. 1A-1C for example) are reacted or mixed with target molecules. After any reactions have occurred, assay fluid containing any microbead complexes as described herein can be allowed to flow through flow path 1822, which can include a microfluidic channel, for example, to an analysis region such as a capillary analysis region described hereinafter in conjunction with FIG. 14B. In the analysis region, a laser beam, such as that shown in FIG. 11A, for example, can illuminated the microbead structures to produce Raman or fluorescence spectra, for example, and a spectrometer such as that shown in FIGS. 14A-14B, for example, can analyze the spectra.

In some embodiments, suction and/or pressure lines are used to produce flow between chambers of the device with the assistance of manually operated or automated pumps.

In the embodiment of FIG. 10, the greater density of glass beads relative to the density of the solution in the assay chamber 1020 has the feature of allowing bead complexes to settle to the bottom of the assay tube and allowing buffer solution to be extracted via a tube 1021. After extraction, another sample or buffer can be injected through a tube 1022. Bubbles in the assay chamber 1020 can provide mixing of beads with buffer solution in the chamber. In other embodiments, separation of beads from solution can be accomplished by filtration.

By controlling flow of fluid between the different chambers of FIG. 10, the valves 1092 and 1093 can cause one or more fluids to assist in the formation of bead complexes in the reaction chamber 1820. Specifically, in FIG. 10, an assay chamber 1020 allows nanoparticles structures and microbead structures to react with target molecules (i.e. hybridize) to form bead complexes. Furthermore, a system can also include a controller (not shown) to control the fluid control devices (valves in FIG. 10) to cause the fluids to assist in the formation of the bead complexes in the reaction chamber. The controller, for example, can open or close the valves, as understood by those skilled in the art of fluid control, to enable transport of bead complexes from the assay chamber 1020 of the reaction chamber 1820 through the channel 1822 to an analysis region. It should be noted that the lysing chamber 1090 in FIG. 10 can be a thermal lysing chamber, as described in conjunction with FIGS. 2A-3C. However, in other embodiments a lysing chamber can be a chemical or enzymatic lysing chamber or configured to perform lysing by other known methods, for example.

Solenoid valves, plastic tubing and connectors from Lee Company (Westbrook, Conn.), laptop from Dell Corporation, software from National Instruments, relay boards from National Instruments, vials, syringe pump from Braintree Scientific, Inc. (Braintree, Mass.), glass microbeads from Polysciences, Inc. (Warrington, Pa.), chemicals from various vendors, DNA from Bio-Synthesis Inc. (Lewisville, Tex.), heaters from Watlow Electric Manufacturing Company (Blue Bell, Pa.), power supply from Agilent Technologies (Lexington, Mass.), and Qiagen (Germantown, Md.) DNeasy® blood and tissue kit.

The schematic diagram of FIG. 10 has an expanded breadboard including cell lysing and silica-gel DNA extraction. The right-side portion of the diagram contains the microbead assay portion. Note that the sizes of the components and tubing lengths are not to scale.

Example 9

Optimization of Cell Lysis and DNA Extraction Functionalities of Breadboard

Construction of the sample lysing subsystem of the breadboard was completed. Lysing of sample cells on a breadboard can be achieved using heat in conjunction with aggressive enzyme reactions since sonication may not be commensurate to the eventual goal of a battery powered analyzer for field use. DNA extraction and purification on the breadboard can be based on a silica-gel-filled capillary.

Example 10

SERS Reader System Design, Build, and Test

A PinPointer™, Agiltron's commercial handheld Raman analyzer (Woburn, Mass.), was used for this program, and the performance of this unit was evaluated using nanoparticle containing DNA probes. For the bulk of the ongoing testing in this program, a PeakSeeker Pro™ from Agiltron (Woburn, Mass.) interfaced with a microscope was used. This highly flexible setup allowed the best optics for the PinPointer™ to be obtained through optimization testing. As samples were standardized with respect to size and substrate bead material, the optical train was simultaneously optimized to obtain the best signal-to-noise ratio SERS measurements. The best optical system for the PinPointer™, as determined via the PeakSeeker Pro™ tests, was achieved through the iterative improvement in the optics to maximize the SERS signal intensity and minimize the noise.

FIG. 11A is micrograph of the 30 µm diameter glass microbead sample prepared. Shown in the micrograph is the position of the 5 µm diameter laser beam 1160 for the measurement of the SERS spectrum shown in FIG. 11B. The oligonucleotide functionalized microbeads contained Rhodamine 6G (R6G) as the probe dye and produced the characteristic SERS spectrum in FIG. 11B. As the first step to evaluate the SERS reader sensitivity required to obtain a good signal-to-noise ratio spectrum in a reasonable time, SERS spectra were collected from initial samples, 30 µm diameter microbead YP-DNA assays. A 1.0 µL drop of the microbead sample was placed on a quartz cover slip to produce the micrograph.

The SERS spectra in FIG. 11B were collected immediately. The spectrum in FIG. 11B is evidence that high quality SERS spectra can be obtained with the probes prepared and collected rapidly. As can be seen in FIG. 11A, the laser beam 1160 was focused to a small spot size so a relatively few dye molecules were probed. A much larger (~100 µm diameter) laser beam can be used in a handheld SERS reader to sample a much larger number of probes. Thus, in some embodiments, a bead complex can fit within a focal point or focal region of a laser beam that analyzes the bead complex in conjunction with a spectrometer. The size of the laser or cross-sectional area and/or diameter can be adjusted by a user to optimize assay sensitivity or to optimize the laser for a particular microbead complex. In some embodiments, a microbead or microbead complex can have a longest dimension (such as a diameter) smaller than a largest cross-sectional dimension of a laser beam. In some embodiments, the longest dimension of a microbead or microbead complex can be larger than the largest dimension of a cross-sectional dimension of a laser beam. Despite the small sampling optical volume, the spectrum in FIG. 11B was collected using a 10 second integration time and averaging 10 spectra for a total measurement time of 100 seconds. Using a larger laser beam can reduce the measurement time to no more than 30 seconds. This result is of very high significance as it demonstrates that with a program designed and synthesized DNA assay, SERS spectra can be generated with sufficient intensity and spectral content for rapid organic analyte detection and identification.

It should also be noted that gold nanoparticles or other nanoparticles of other metals can be, for example, at least two orders of magnitude smaller than bead complexes, such as bead complexes 1100 in FIG. 11A. Thus, nanoparticles are not visible in FIG. 11A, and it should also be understood that the bead complexes in FIGS. 1A and 1B are not to scale; namely, the microbead 102 can be at least two orders of magnitude larger than the gold nanoparticles 106.

In many embodiments, the microbeads are between 1 µm and 100 µm, for example. More preferably, diameters are in a range of between 30 µm and 50 µm. In some embodiments, this narrower range allows microbeads to be large enough for greater visibility during testing or setup, while being small enough to be more easily transported through flow paths. Furthermore, in embodiments in which filtration is done to separate microbeads from solution, for example, it can be easier to filter microbeads that are larger than about 10 microns in diameter.

Figure 12:
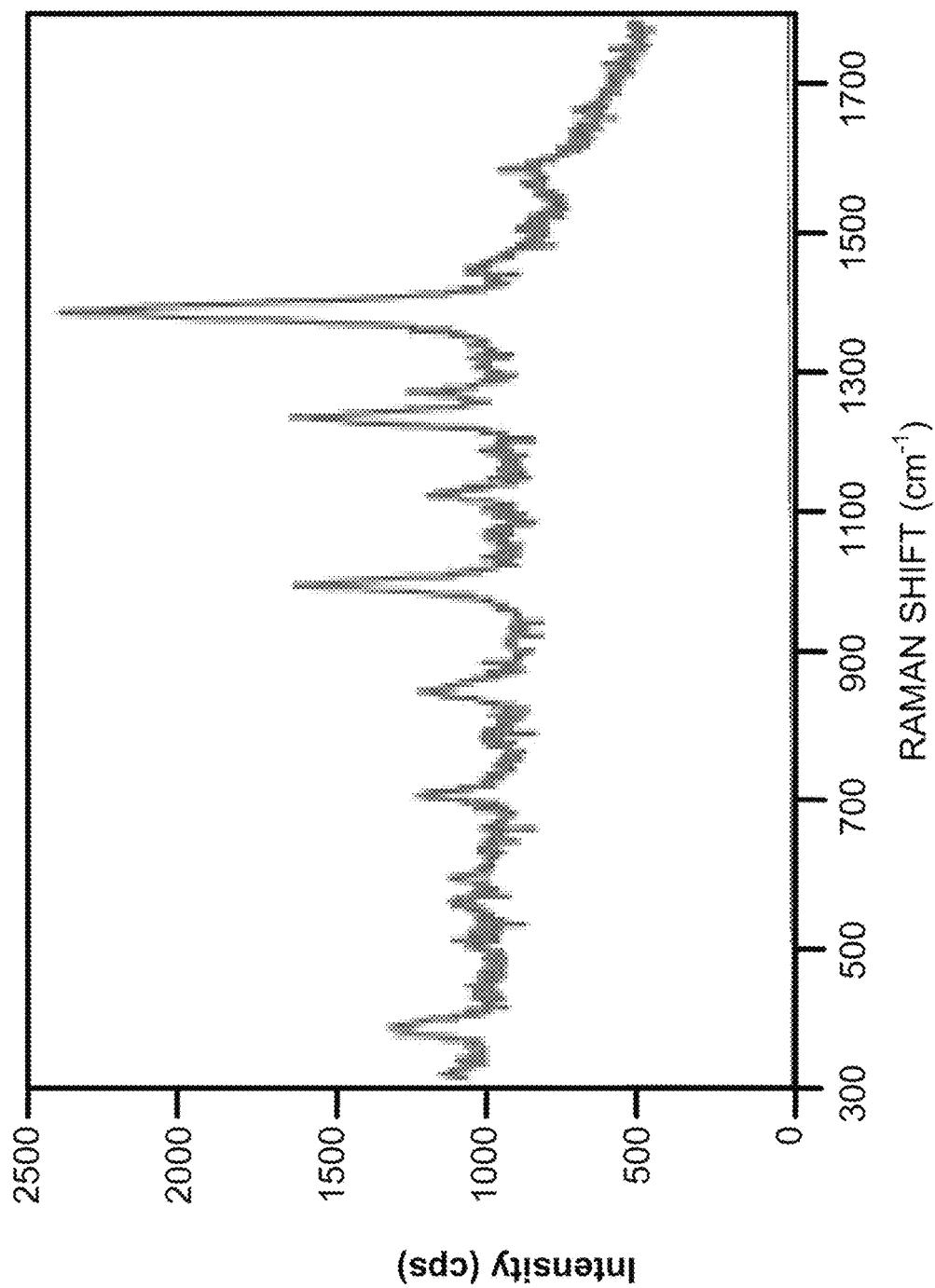
FIG. 12 is the graph showing SERS spectrum of the glass microbeads sample containing Cy3 as the probe dye.

FIG. 12 shows a SERS spectrum of a second glass microbead assay sample containing Cy3 as the probe dye. The characteristic Cy3 SERS spectrum was produced. This sample comprised 30 µm diameter glass microbeads supporting the YP-DNA assay. For these assay samples, Cy3 was used as the Raman dye in the probe DNA instead of R6G as was used in the first assay sample prepared. As before, a 1.0 µL drop of the microbead sample was placed on a quartz cover slip and the SERS spectra were collected immediately. The spectrum in FIG. 12 required only one second to collect, providing evidence that high quality SERS spectra will be obtainable with both the R6G and Cy3 probes prepared. This result demonstrates successful multiplexing, namely the ability to generate high quality SERS spectra from probes with at least two different Raman dyes with sufficient intensity and spectral content for rapid target detection and identification.

Figure 13:
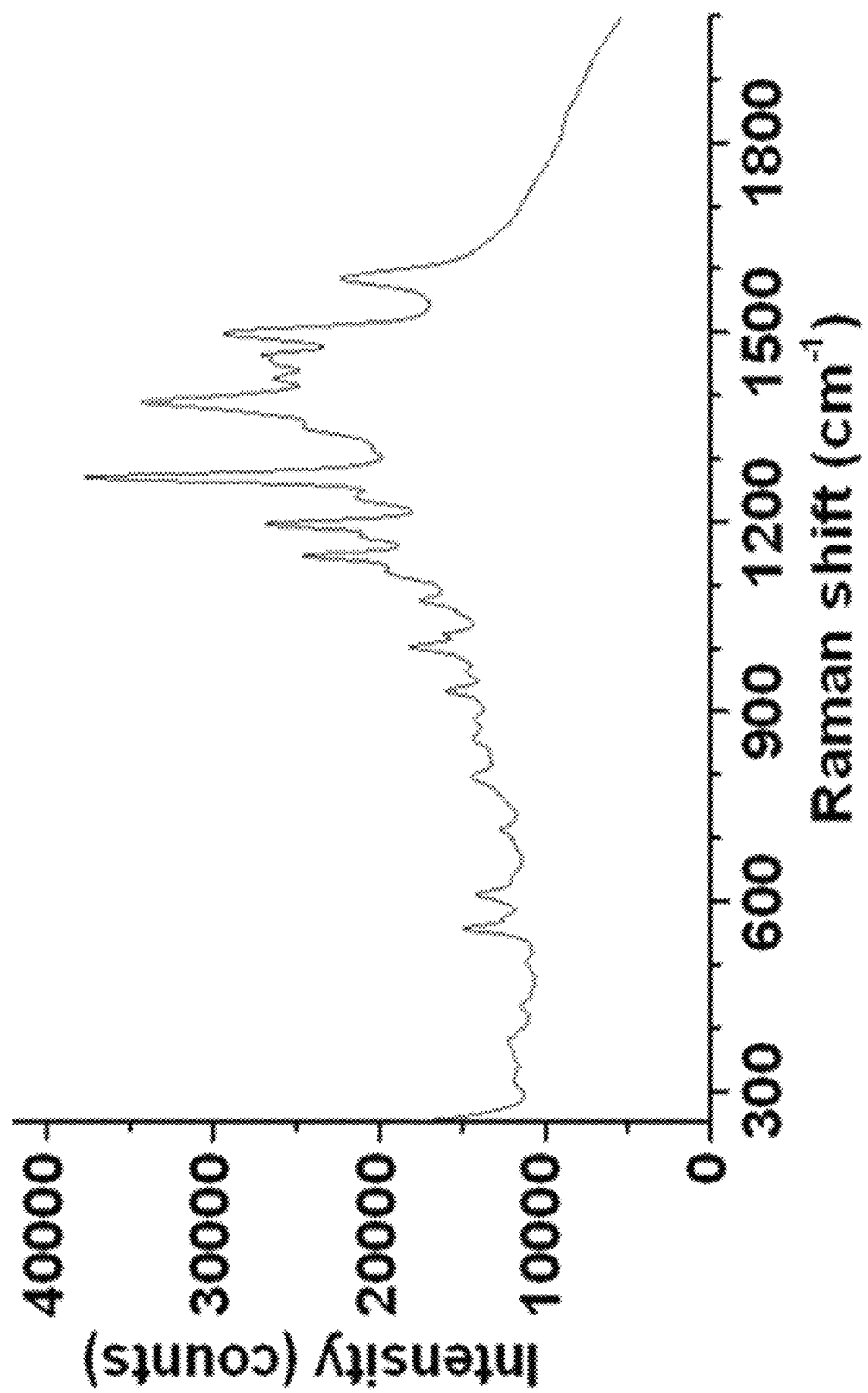
FIG. 13 is a graph showing SERS spectrum of a 45 µm diameter glass microbeads sample containing oligonucleotide functionalized microbeads using Cy3 as the probe dye.

FIG. 13 shows a SERS spectrum of a 45 µm diameter glass microbead sample (third sample). The oligonucleotide functionalized microbeads of the third sample contained Cy3 as the probe dye and produced the characteristic Cy3 SERS spectrum.

Figure 14B:
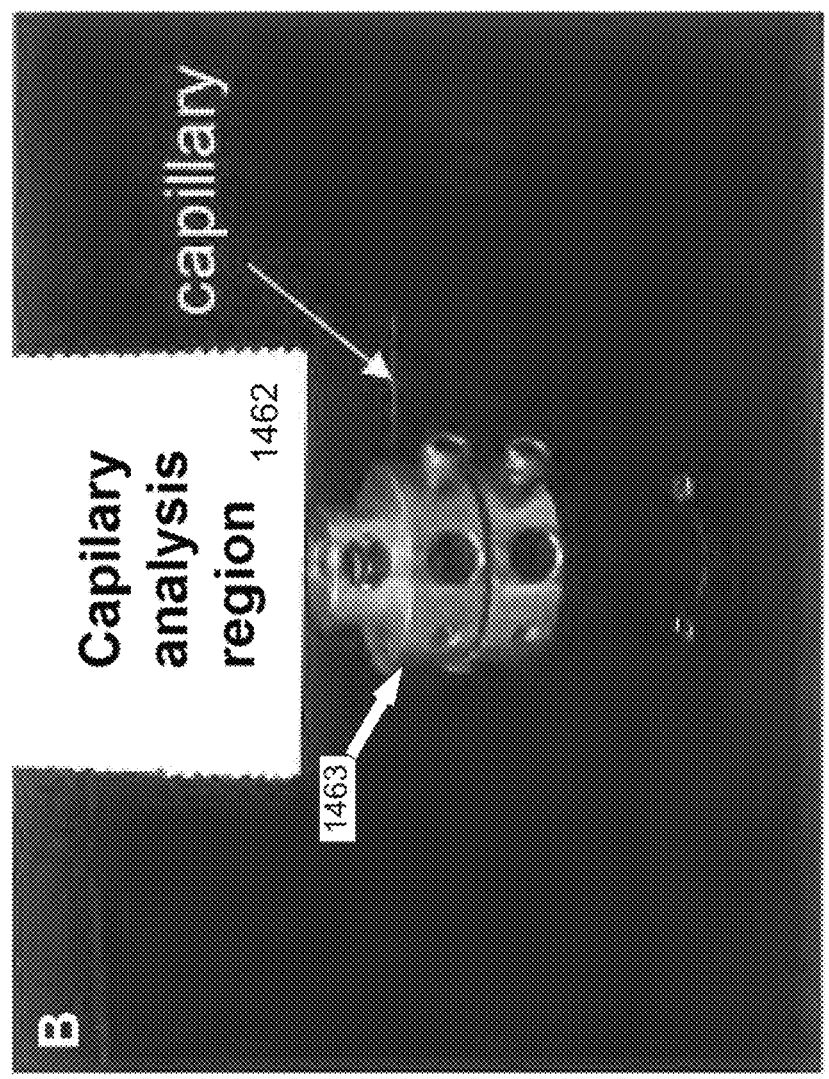
FIGS. 14A and 14B are photographs of an adapter fabricated to test Pinpointer™ sensitivity for collecting SERS spectra from assay beads in a channel.
Figure 14A:
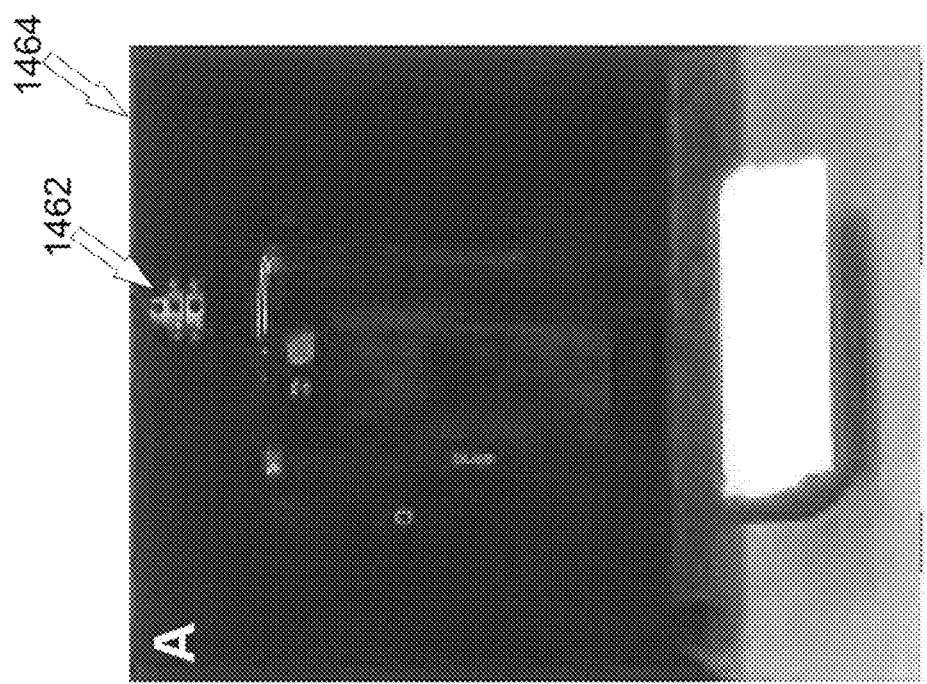

The third sample, of YP-DNA Bead-AuNP-Cy3 complexes, was, prior to SERS measurements, with a vial of 0.3 M phosphate buffer saline solution mixed and allowed to incubate at room temperature. Immediately afterwards, a small droplet of liquid containing active SERS-DNA beads (i.e. microbead complexes) was applied to a quartz microscope slide, and then a thin quartz coverslip was placed on top of the droplet. The beads were then measured with the Agiltron PeakSeeker™ system equipped a 785 nm laser and 50× long working distance objective. The beam spot size was slightly larger than the diameter of the beads; each bead was measured for 10 seconds with 100 mW power. The spectrum shown in FIG. 13 demonstrates the well-defined and exceptionally intense Cy3 signal that was measured on the beads. The SERS signal was much more intense when the sample was mixed with the phosphate buffer just prior to the measurement. Previous samples were mixed prior to shipment to the SERS analysis location and yielded SERS signals only about 10% as intense as the spectrum in FIG. 13. This result is significant as it leads to incorporating mixing the sample with the buffer just after sample injection and filtering and demonstrates that by mixing just after sample injection and filtering, SERS signals can be significantly increased FIG. 14A-14B show an embodiment of an adapter 1463 fabricated, to test PinPointer™ spectrometer unit 1464 sensitivity for collecting SERS spectra from assay beads in a channel. To demonstrate the feasibility of handheld microfluidic applications, a PinPointer™ was tested to collect signals from actual YP assay glass beads in a 1 mm ID glass capillary channel (analysis region) 1462.

While a surface enhanced Raman spectrometer is shown in FIG. 14A, other embodiments can include a fluorescence spectrometer or other type of spectrometer, for example. Fluorescence spectroscopy can also be used to analyze the complex if a fluorescent label is used instead of a metal nanoparticle coupled with a Raman dye, for example. Furthermore, while the analysis region 1462 in FIGS. 14A and 14B is a capillary, in other embodiments, the analysis region can have other configurations, shapes, and orientations with respect to the spectrometer. It should also be noted that a spectrometer such as the PinPointer™ 1464 can be coupled to the reaction chamber 1820 in FIG. 10 through a channel 1822 in FIG. 10 on a platform to provide a reaction and analysis system that is mobile.

It should be understood that results of a spectroscopic analysis can be reported to a system user, for example, by any known method. For example, a positive test for a pathogen can be reported to a user by an audible alarm or visual LED indicator, for example. Other example means of indicating results of a spectroscopic analysis include a text on an LCD screen, WiFi or text message signaling, etc.

Figure 15:
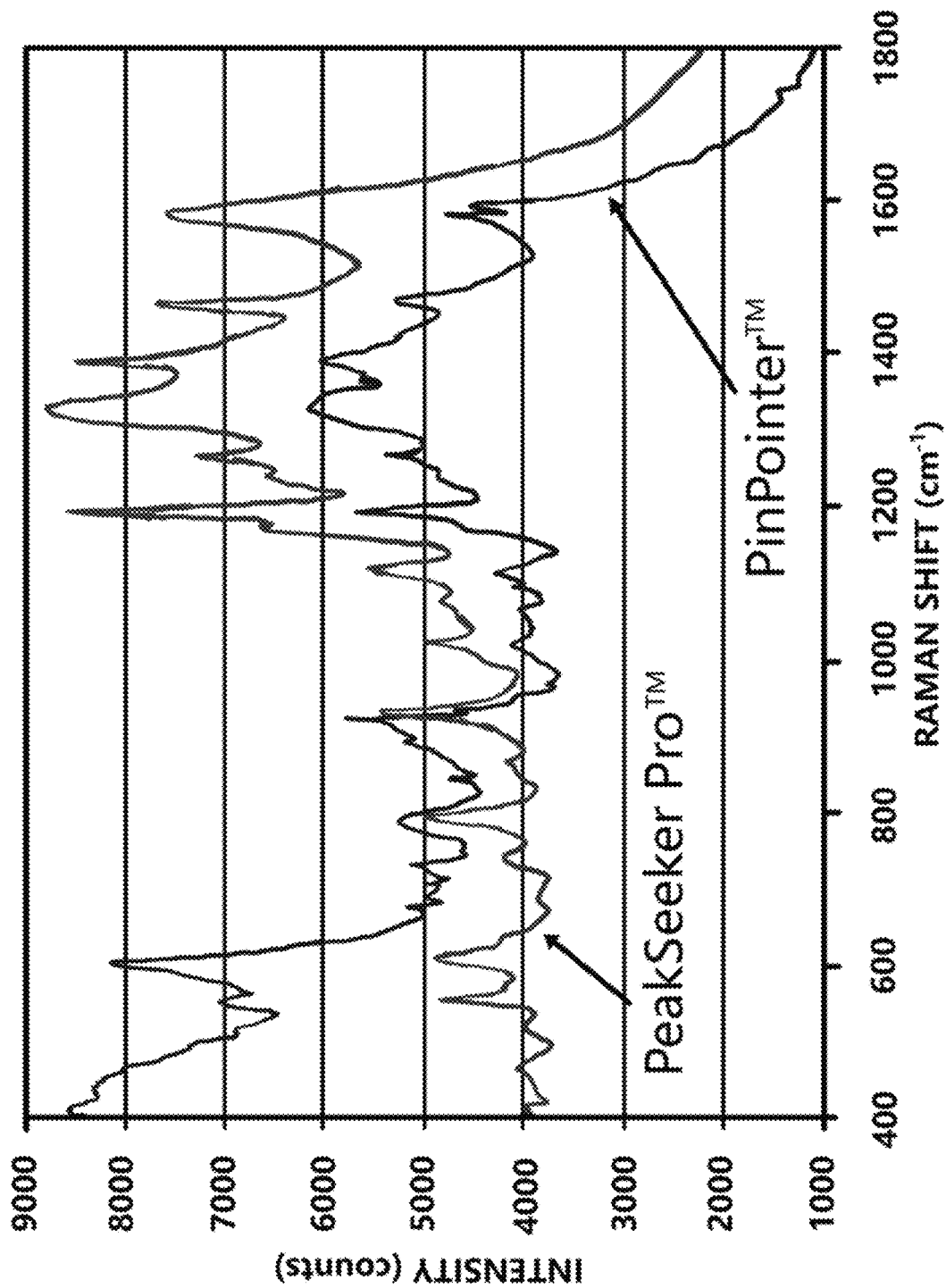
FIG. 15 is a graph showing SERS spectra of a YP assay incorporating the Cy3 dye.

FIG. 15 shows SERS spectra of the YP assay incorporating the Cy3 dye. SERS detection of random array assays using the PeakSeeker Pro™ benchtop Raman analyzer interfaced to a microscope system was already proven. In this test, SERS spectra collected with the PeakSeeker Pro™ and PinPointer™ were compared. The results, shown in FIG. 15, clearly show that the PinPointer™ is able to 1) produce SERS spectra characteristic of the YP assay incorporating the Cy3 dye, and 2) produce SERS spectra with sufficient spectral content for differentiation in an assay multiplexing system. Thus, more expensive or larger SERS detection systems are not necessary.

Example 11

System Integration, Evaluation, and Optimization

Figure 16A:
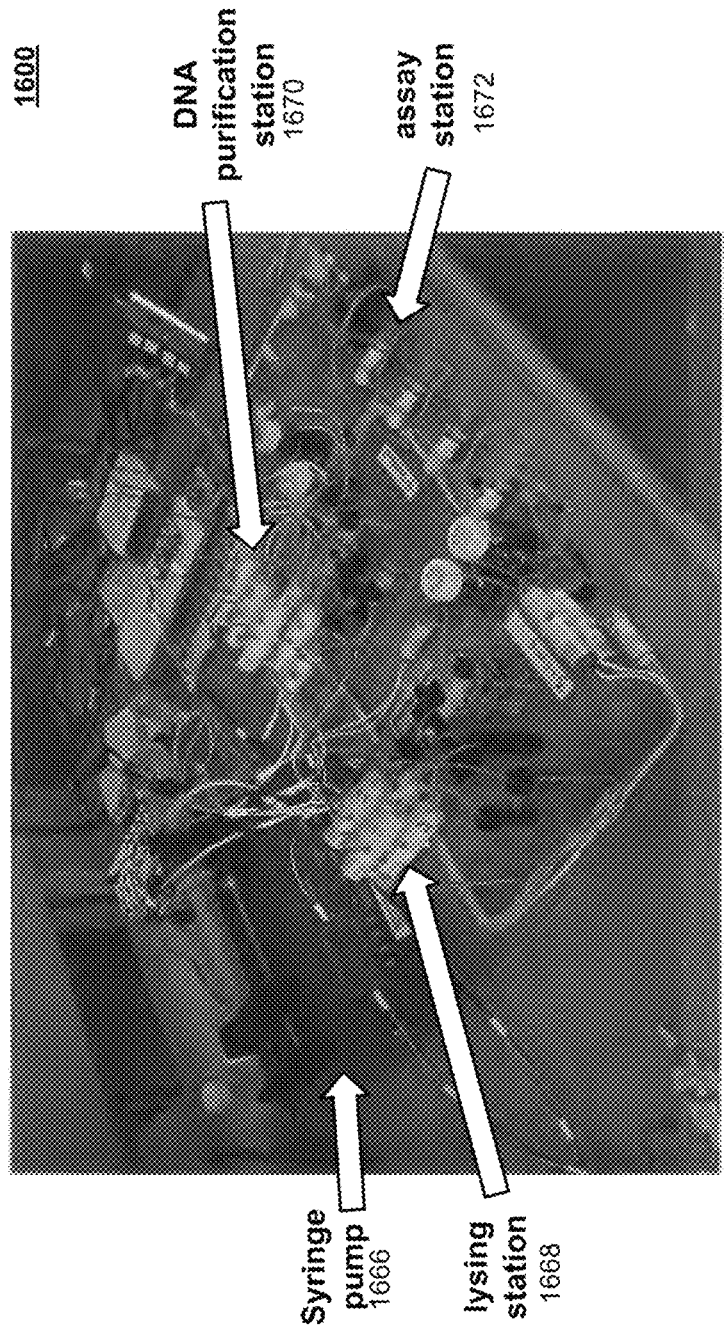
FIG. 16A is a photograph showing an embodiment breadboard configuration including lysing, DNA purification, and assay stations.

FIG. 16A shows an embodiment of a system described herein in a breadboard 1600 configuration used for breadboard testing described herein. The breadboard system 1600 includes a syringe pump 1666 to drive fluid movement, a lysing station 1668, a DNA purification station 1670, and an assay station 1672.

As the buildup of the breadboard system is complete, all of the chemicals, buffers, and biochemicals necessary for operation can be incorporated into the automated operation of the random array assays.

Figure 16B:
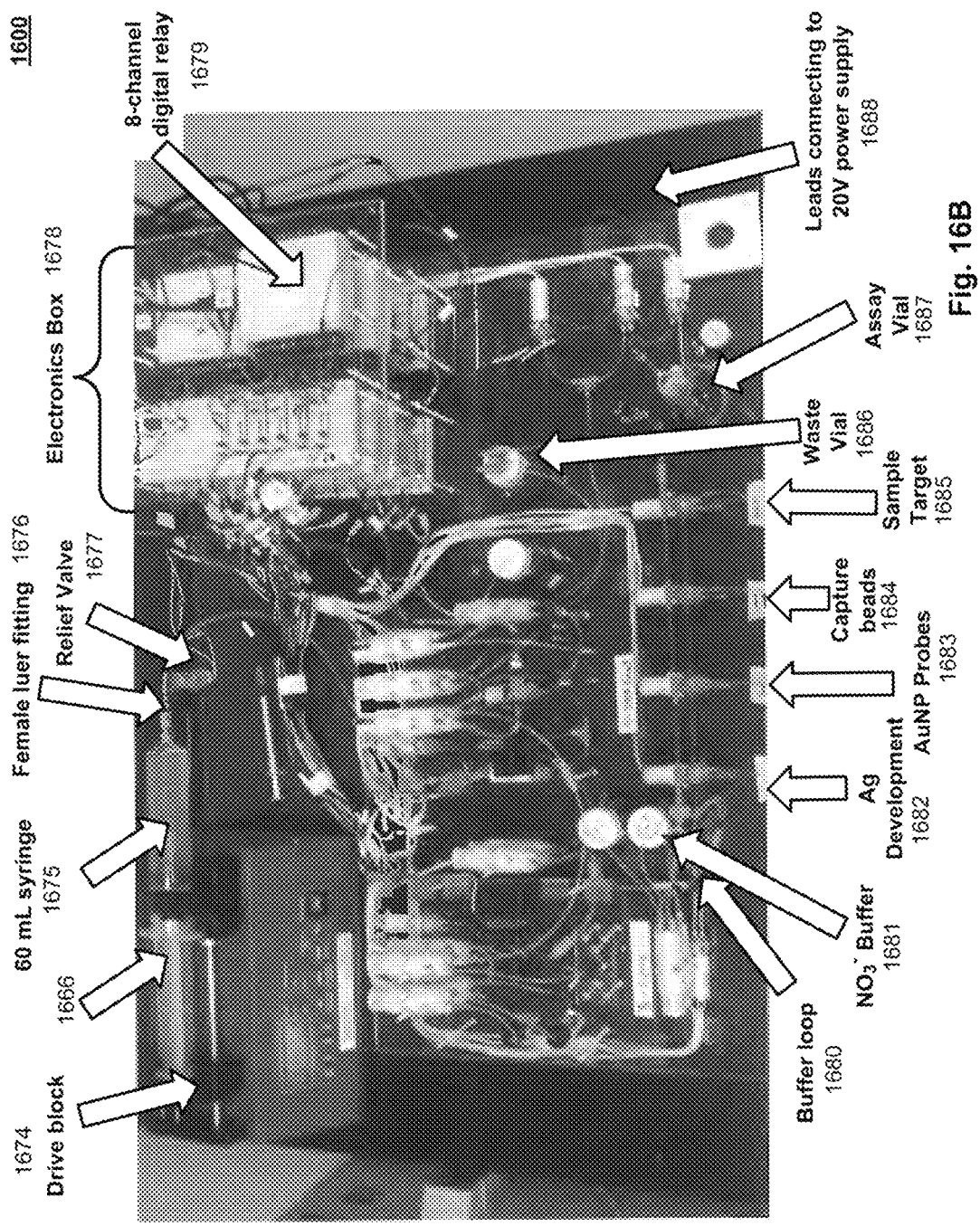
FIG. 16B is a photograph pointing out additional features of the breadboard of FIG. 16A.

FIG. 16B is another photograph pointing out other features of the breadboard 1600 configuration shown in FIG. 16A. The subsections hereinafter describe the operation of certain features of the breadboard of FIGS. 16A-16B.

FIGS. 16A-16B show embodiments of a system as described herein comprising a syringe pump 1666 on an automated drive block to create fluid movement through the system, a lysing station 1668 (i.e. a cell lysing module), a DNA purification station 1670 (i.e. a biological target purification module), and an assay station 1672 (i.e. an assay mixing module).

The system of FIGS. 16A and 16B is configured to be run via control software implemented in LabView on a computing device or apparatus 1010 (not shown). A syringe pump 1666 is mounted to a drive block 1674 configured to drive a syringe 1675. The syringe can be connected to a computing device or apparatus 1010 (not shown) via an RS-232 'phone jack' terminal (not shown). This RS-232 cord connects to an adapter with a 9 pin connector, which in turn connects to another adapter that ends with a standard USB cable. The USB cable is plugged into the computer. Wires coming from an electronics box 1678 are connected to the appropriate pin inputs on the syringe pump 1666.

The breadboard 1600 includes four National Instruments 8-channel solid state relays 1679 in the electronics box 1678. As used herein, a controller can be the electronics box 1678, for example, and can be coupled to a computing device or apparatus such as the one described in apparatus 1010. USB cables from the four relays 1679 are plugged into respective relay boxes. These cables are plugged into corresponding USB slots on a USB dock, which is plugged into a USB input on the computer (apparatus 1010, not shown). A 20V power supply (not shown) with leads 1688 (example of electrical coupling, electrical communication, and/or operational coupling) provides all the necessary power to the fluidic valves, optical sensors, and cooling fan.

Setting up a fluidic system as described herein is now described according to the embodiments in FIGS. 16A and 16B. There can be four sample/reagent 'loops' (an Ag development loop 1682, AuNP probe loop 1683, capture bead loop 1684, and sample target loop 1684, also shown schematically in FIG. 10 and FIG. 27, for example) presented at the front edge of the breadboard 1600, and each of these is a ~10 cm long Teflon tube with MINSTAC (threaded) connectors on both ends. One end of the sample/reagent loop is connected to a tan-colored 3-way manifold that delivers each of the samples/reagents to a central line that leads to the reaction/assay vial. The other end of the sample/reagent loops connects to a 2-way valve located directly below the aforementioned central tube line. The four sample/reagent loops can be unscrewed from manifolds and a 2-way valve to flush out the sample/reagent loops with de-ionized (DI) water in a squirt bottle. Water can be removed from sample/reagent tubes, and residual water from the threaded connection ports can be soaked up.

Each sample/reagent loop can hold a liquid volume of up to 70 μL so each loop is filled with ~70 μL of solution. Although several ways may be used to fill the loop with a predefined volume, one way is to use a pipet to withdraw 70 μL into a pipet tip (not shown), and then carefully hold the pipet tip flush against the tip of the Teflon tubing of the sample/reagent loop. The liquid is slowly injected into the tube, taking care to avoid letting the liquid drip out where the pipet tip and tube come together. To avoid dripping, the tip and tube are brought together in a firm and flush manner. After the liquid sample has filled the tube, the end of the tubing loop is connected first to the 2-way valve and finger tightened. Note that gravity tends to drain the liquid out of the loop if the tube is held in a vertical manner. Thus, the tube is held substantially horizontal until the first end of the tubing is connected to the 2-way valve.

For the fourth loop 1682, which holds the two components of the Ag Development step (initiator and enhancer), 30 μL of one component are added first, and then a pipet is used to inject a small plug of air (~1 cm) immediately behind the first component. Afterward, 30 μL of the second component are then injected. The air plug keeps the components separated so that they do not mix/react until injected into the assay vial 1687.

After filling each sample/reagent loop and connecting to the 2-way valves and manifolds, the loop tubes are finger tightened to ensure firm connections. Next, the NO3-buffer vial 1681 is checked for sufficient buffer (at least a ¼ full). The buffer is replaced if it is more than two days old. The waste vial 1686 then emptied if it is more than ¾ full. Note that in order to empty the waste vial, the tubes remain connected to the waste vial's lid. The vial is carefully removed from the vial holder prongs, and the vial is twisted to unscrew it from the lid (this prevents breaking of the seals on the tubing connected to the lid).

To set up the syringe pump 1666, the large 60 mL syringe 1675 is disconnected from a female luer adapter 1676 (which connects to a relief valve 1677 and the main tubing line that drives the rest of the breadboard pneumatically). The syringe 1675 is attached to the syringe pump with the syringe withdrawn to about ¾ its total capacity. The driving block on the syringe pump is adjusted so as to have it approximately align with the end of the syringe plunger when attached to the pump. The clamps that hold the syringe and plunger in place are checked for being tightly secured and that there is no extra room for the syringe to move around. After the syringe is set up, the luer adaptor is reattached to the syringe pump. The threaded fitting on the Teflon tubing is checked for being securely screwed into the plastic luer adaptor.

Setting up Assay Vial on Breadboard. The glass assay vial 1687 and the small Teflon tubing adaptor (not shown) are cleaned. Sonication in water removes most particulates from the vial. The vial is rinsed thoroughly with DI water and EtOH and blow dried.

The small Teflon tubing adaptor is attached into the central threaded hole on the plastic base of the assay vial holder. The clean glass assay vial is slid onto the short length of Teflon tubing sticking upwards out of the plastic base (not shown). The rubber cap is attached with several small holes onto the top end of the glass vial. There is a square piece of Teflon with a large central hole that can be attached to the four threaded rod posts surrounding the assay vial. The assay vial is designed to fit into the central hole. This square block simply helps to hold up the glass vial in a vertical manner. There are two tubes that need to be inserted through the rubber cap and into the vial: the sample/reagent injection tube and the waste/supernatant removal tube. The sample/reagent injection tube is inserted ~½ to ⅔ of the way into vial from the top (<1 cm or so from the bottom of the assay vial). The waste/supernatant removal tube is inserted almost to the very bottom of the assay vial (where the taper becomes very narrow). About 1-2 mm are left between the tip of this tube and the bottom surface of the assay vial.

Running the Assay. The LabVIEW breadboard control program is started on a computing device or apparatus 1010 (not shown). During each step of the assay, the syringe pump is normally either 'infusing' or 'withdrawing', and corresponding LEDs turn on/off in the electronics box. The movement of liquids in the system can be observed by eye at each step to ensure that the software and/or hardware is operating properly. Sensors, such as optical sensors, can also be implemented in the system to create feedback loops which electrical components of the system (such as the controller and/or computing device) can use for active, real-time, monitoring of system and/or assay status. An example of sensor implementation is shown in FIG. 10.

The main observations are as follows. During the sample or reagent injection steps, the corresponding liquids should be flushed out of the sample/reagent loops and into the assay vial. A small pellet of beads should be observed that quickly settles to the bottom of the assay vial, and these beads should always be present throughout the assay. However, the pellets should be mostly dispersed throughout the liquid during the mixing steps. Bubbles are injected from the bottom of the assay vial during the mixing step, and only during this step. $NO_3^-$ buffer is withdrawn from the buffer vial during the 'withdraw buffer into buffer loop' step, fills the buffer loop, and stops filling the tubing when the front end of the buffer plug reaches an optical sensor. Additionally, the buffer in the buffer loop is emptied into the assay vial. The supernatant liquid is withdrawn from the assay vial after each mixing or incubation process. After the initial mixing/incubation steps (with AuNP probes), and after the excess probe solution (pink colored) has been removed and the beads are washed with $NO_3^-$ buffer, the bead pellet should have a definitive pink color if the beads/targets/probes are all complementary. If the beads are pink as described above, then they should begin to turn a brownish color within a couple of minutes of injecting/mixing the Ag Development solution. The drive block on the syringe pump should not reach the back stopper of the pump, or it will stall.

Example 12

Microfluidic Channel Demonstration Device

Figure 17B:
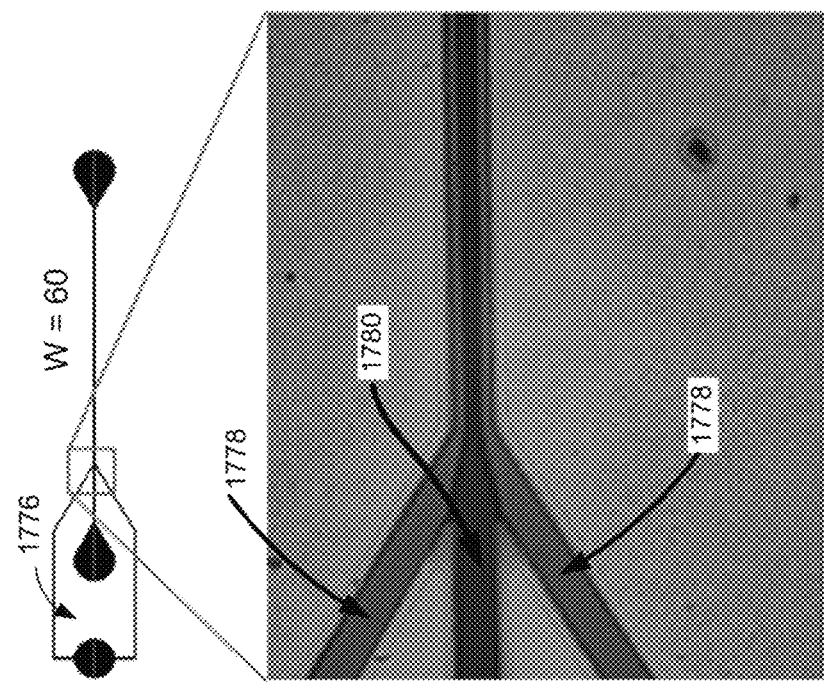
FIG. 17B is a magnified image showing the hydrodynamic focusing observed in a microchannel like those of FIG. 17A with food coloring being pumped into the outer (chief) channels, and red food coloring being pumped into the center channel.
Figure 17A:
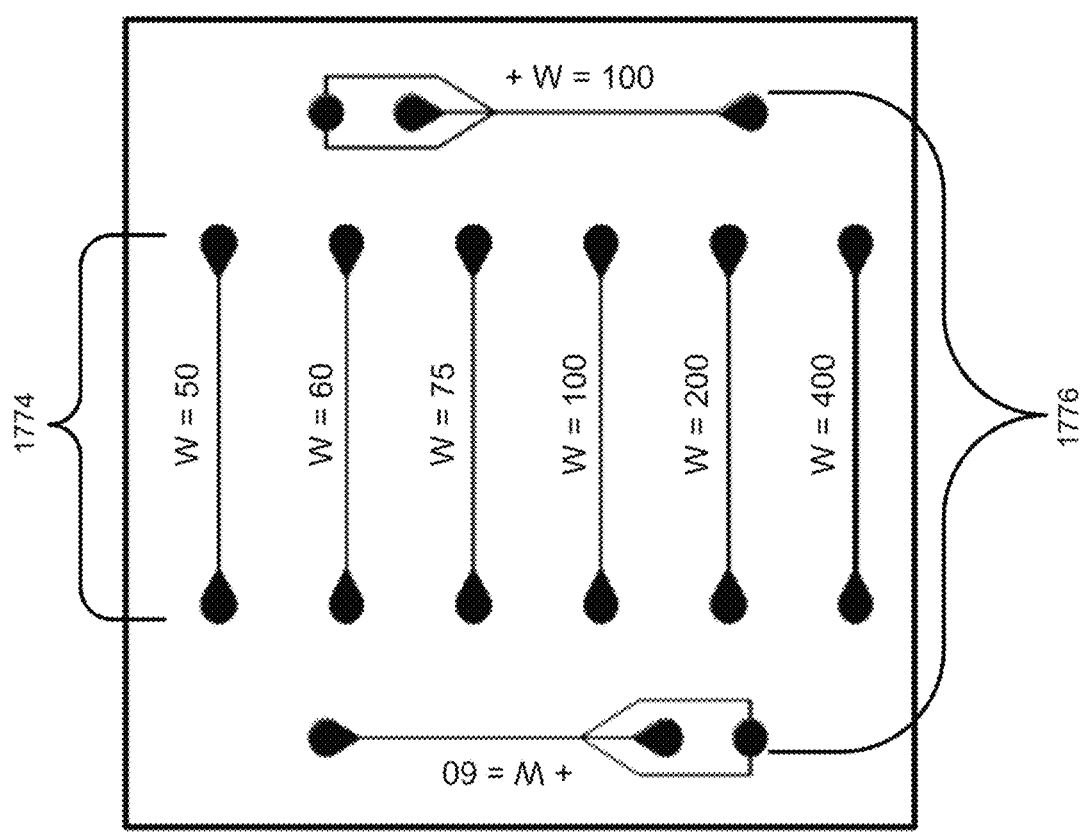
FIG. 17A is a plan view of a 6 inch transparency mask showing single- and sheath-channel designs.

FIG. 17A shows 6 inch transparency mask illustrating single- and sheath-channel designs (1774 and 1776, respectively) for microfluidic channels that can be used to transport and/or analyze microbead complexes as described herein. The widths of the channels (in microns) are indicated for each next to each pattern. FIG. 17B provides a magnified view of a sheath channel pattern with 60 μm wide channels. FIG. 17B shows the hydrodynamic focusing observed with green food coloring being pumped into the outer (sheath) channels 1778, and red food coloring pumped into the center channel. The picture was acquired with a 5× objective.

Microfluidic channels like those of FIGS. 17A-17B were fabricated using traditional polydimethylsiloxane (PDMS) molding techniques. The mold was fabricated onto a 6 inch diameter silicon wafer. Positive-tone photoresist was spin coated onto the wafer, and a transparency mask shown in FIG. 17A was used to selectively expose the photoresist film to UV-light. The transparency mask was designed to have numerous channel patterns/dimensions. Deep reactive ion etching (DRIE) was then used to anisotropically etch the patterned wafer, so that only the exposed wafer regions were etched. The wafer was etched to a depth of 57 um. PDMS was then prepared and poured over the patterned/etched wafer; the resulting PDMS film thickness was approximately 1 mm. The PDMS-coated wafer was then cured at ~100° C. for at least 5 minutes. After curing, the PDMS film was peeled off the molding wafer, and then individual channel patterns were cut from the film. The PDMS pieces were then treated with the electrical discharge from a tesla coil to chemically activate the surface, which was then applied to a Si wafer or glass microscope slide and allowed to bond for several hours.

Through-holes were then punched into the PDMS over the inlet/outlet reservoirs, and 1 mm outer-diameter Teflon tubing was inserted into these ports. Red and green food coloring were used to determine the flow pattern of the channels, as illustrated in FIG. 17B. The food coloring was loaded into syringes, which were attached to a syringe pump (not shown); the syringe pump was set to a pump rate of 20 µL/min. FIG. 17B illustrates the level of flow control achieved with this system.

Figure 18:
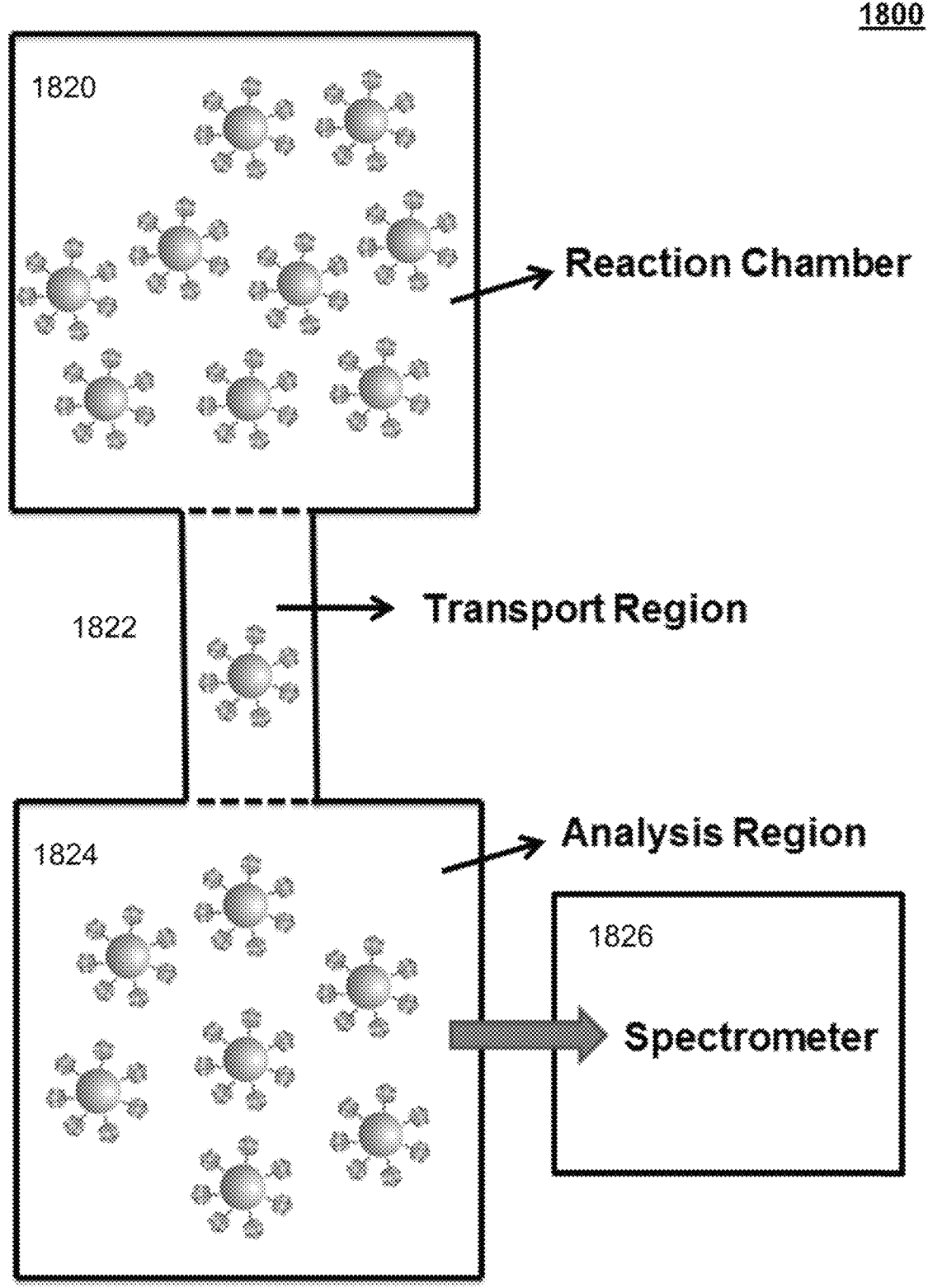
FIG. 18 is a block diagram illustrating an embodiment system for detecting the target biological molecule.

FIG. 18 is a block diagram illustrating a system 1800 for detecting a target biological molecule, such as the target DNA molecule 112 illustrated in FIGS. 1A and 1B. The system 1800 includes a reaction chamber 1820 that enables formation of a biological molecule bead complex, such as the bead complexes 100a and 100b shown in FIG. 1A. A channel 1822 is configured to transport the bead complex from the reaction chamber 1820 to an analysis region 1824, and a spectrometer 1826 is configured to analyze the bead complex at the analysis region 1824.

Figure 19:
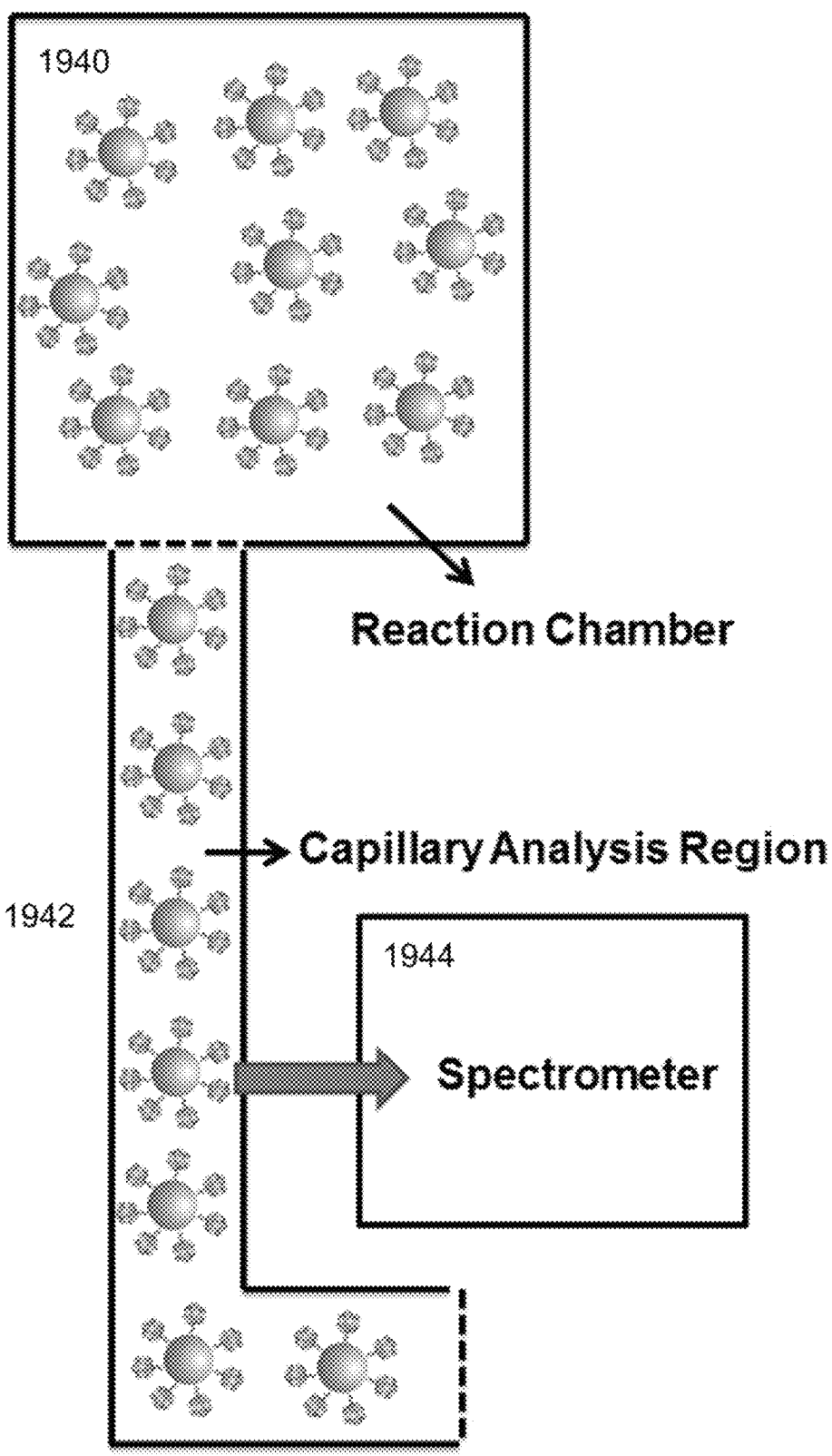
FIG. 19 is a flow diagram illustrating an embodiment method of detecting a biological target molecule.

FIG. 19 illustrates an embodiment method 1900 of detecting a biological target molecule. At 1940, a biological bead complex is formed in a reaction chamber, such as the reaction chamber 1820 illustrated in FIG. 10 and FIG. 18. At 1942, the bead complexes transported from the reaction chamber to an analysis region through a channel, such as a microfluidic channel like the channels 1778 and 1780 illustrated in FIG. 17B. At 1944, the bead complex is spectroscopically analyzed at the analysis region by a device such as a Raman spectrometer. Spectroscopic analysis can include, for example, surface enhanced Raman spectroscopy or surface enhanced resonance Raman spectroscopy. A stimulation signal (e.g., laser beam) that causes the bead complex to react to produce a Raman spectrum can be part of the spectrometer 1826. In some embodiments, the spectrometer 1826 is another type of spectrometer, such as a fluorescence spectrometer.

Figure 20:
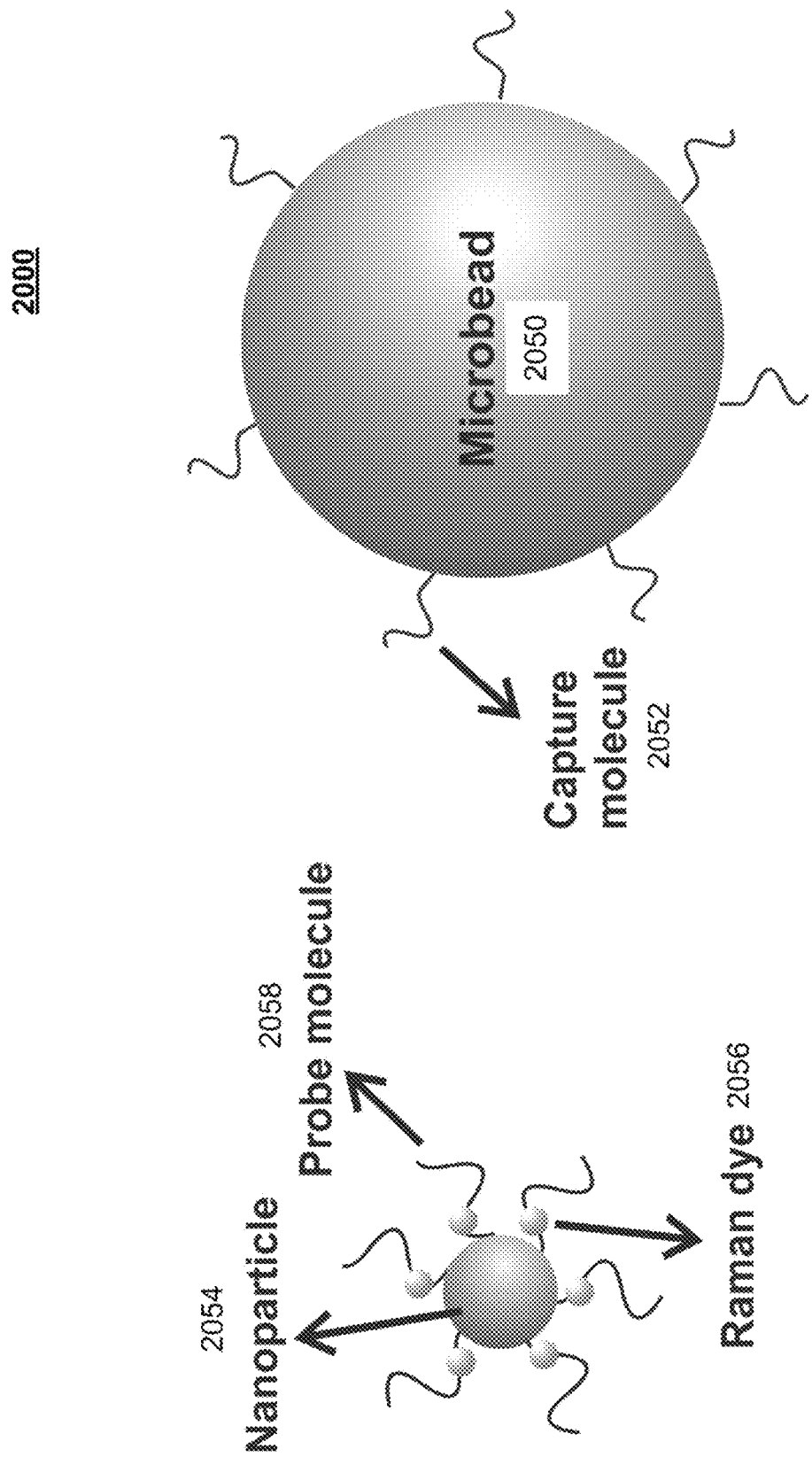
FIG. 20 is a schematic diagram illustrating an embodiment kit.

FIG. 20 is a schematic illustration of an embodiment of a microbead kit 2000. The kit 2000 can include one or more microbead 2050 to which one or more capture molecules 2052 are coupled. The kit 2000 also can include one or more nanoparticles 2052 coupled to one or more probe molecules 2058 via a label 2056. The nanoparticle[s] 2054 can be a gold particle, for example, such as the gold nanoparticles 106 in FIG. 1B. The nanoparticles 2054 can also be another type of metal (e.g., noble metals) with a core shell structure that can produce a proper plasmonic response for SERS with a given label, such as silver, copper, aluminum, platinum, nickel, etc., or combinations thereof. Furthermore the nanoparticles 2054 can have other nanoparticles attached thereto. For example, the gold nanoparticles 106 in FIG. 1B can have one or more silver nanoparticles attached thereto in order to shift the resonance frequency of the gold nanoparticles 106 to match the Raman dye 108 to produce a stronger surface enhanced resonance Raman spectroscopy signal. The probe molecule 2058 and capture molecule 2052 are configured to be coupled together via a biological target to form a biological molecule bead complex. The biological target can be, for example, a target DNA molecule such as the target DNA molecule 112 in FIGS. 1A-B. However, the biological target (not shown in FIG. 20) can also be a protein or an RNA molecule (e.g., from a virus), for example. Homologous or heterogenous capture molecules and homologous or heterogenous probe molecules can be used.

Figure 21:
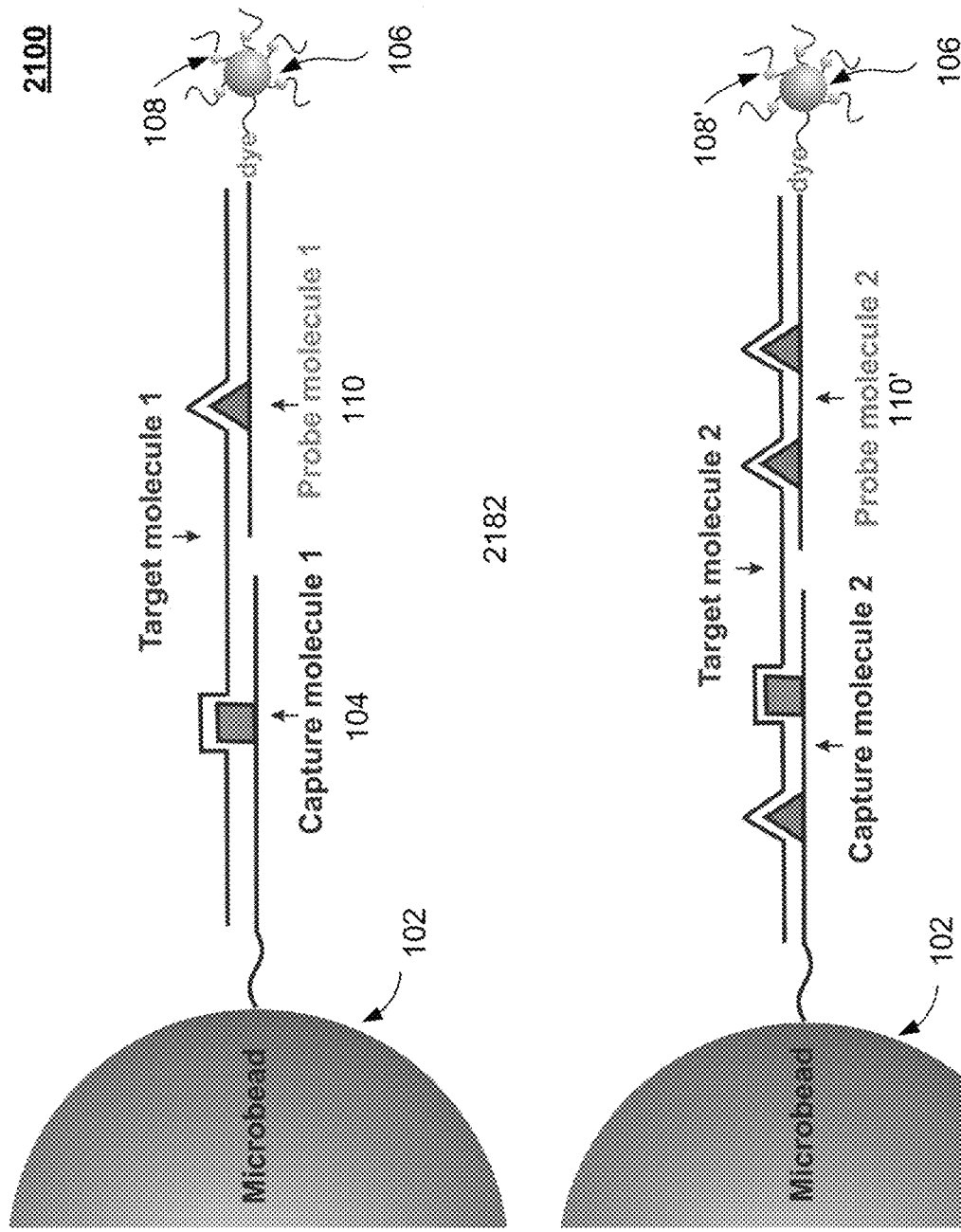
FIG. 21 is a schematic illustration of a random array having microbeads and nanoparticles configured to attach to different respective biological target molecules.

FIG. 21 illustrates that different microbeads can have different respective capture molecules coupled thereto (heterogenous capture molecules), and different nanoparticles can have different respective probe molecules (heterogenous probe molecules) coupled thereto by the same or different respective labels. The different respective capture molecules and different respective probe molecules can be designed to be coupled together, respectively, via different respective biological targets to form a random array of at least two biological molecule bead complexes in random locations in a fluid. The random array 2100 includes a fluid 2182 having two microbeads 102 in different, random locations in the fluid. Furthermore, there are two gold nanoparticles 106 in the fluid 2182, which include different probe molecules 110 and 110', respectively, coupled to the gold nanoparticles 106 via different Raman dyes 108 and 108', respectively. The probe molecule 110 and capture molecule 104 are configured to be coupled together via a target molecule 112. A target molecule 112' is also contained within the fluid 2182, and the probe molecule 110' and capture molecule 104' are configured to be coupled together via the target molecule 112'. In this way, different biological agents, such as the different target molecules 112 and 112' can be part of a random array. Furthermore, when the beads and nanoparticles are coupled together via reaction with the target molecules, the respective bead structures formed thereby can flow in the fluid 2182 through a flow path such as the flow path 1822 in FIG. 10 to an analysis region such as the capillary analysis region 1462 in FIGS. 14A and 14B be to be spectroscopically analyzed simultaneously. A spectrometer such as the Pinpointer™ 1464 shown in FIG. 14A can distinguish the bead structures from each other via respective Raman spectra produced by the different Raman dyes 108 and 108'. Thus, a kit that includes the respective beads 102 and respective nanoparticles 106 can be used to form different bead complexes that can be analyzed simultaneously in a random array.

It should be noted that other embodiments of kit 2000 can include microbead 2050 and the nanoparticle 2054 as part of corresponding collections of multiple microbeads and multiple nanoparticles. The collections of multiple microbeads and multiple nanoparticles can be located in a fluid solution 2182 (described hereinafter in conjunction with FIG. 21) or in separate solutions (not shown). When reactions with potential biological agents are desired, respective solutions can be brought together with target DNA molecules, for example, in a reaction chamber such as the chamber 1820 in FIG. 10.

As one alternative to the bead structures illustrated in FIGS. 1A-1B and FIG. 21, a probe molecule can be directly immobilized onto a surface of a gold nanoparticle independently of the Raman label. For example, this can be achieved by using a probe sequence with a thiol-modified terminal group, which will covalently immobilize the probe molecule to the nanoparticle surface. The Raman label (e.g., Cy3) can then be co-immoblized with the probe molecule (either sequentially or in parallel) onto the surface. This can allow the probe sequence and label to be immobilized onto the nanoparticle in various yet controllable ratios, as opposed to the fixed 1:1 ratio achieved when the probe sequence is covalently bonded to the Raman dye, and immobilized together. One advantage of including a plurality of labels for each probe molecule is a corresponding increase in Raman signal.

Example 13

Figure 22:
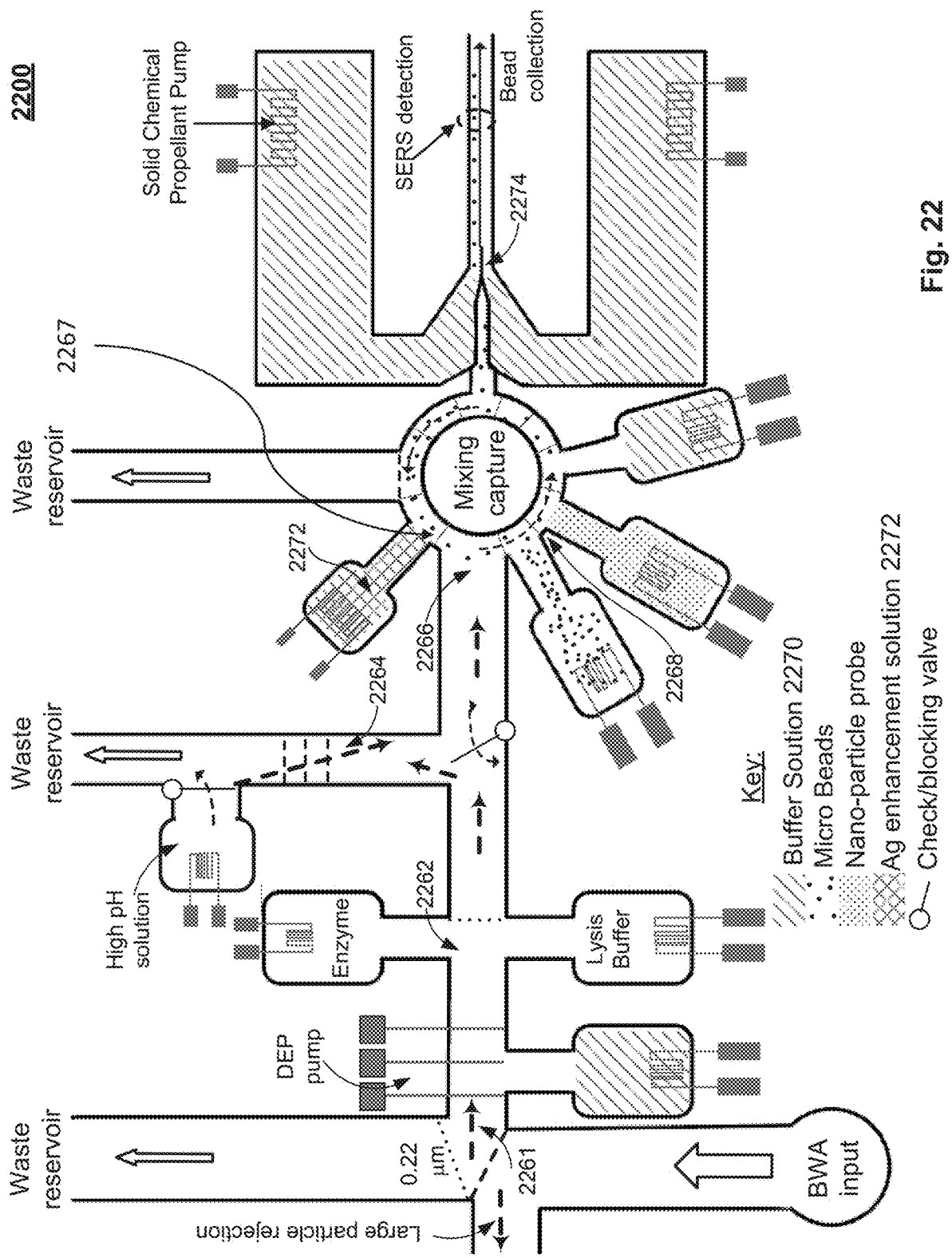
FIG. 22 is a schematic illustration of a random array assay solid state cartridge implementation of an embodiment system.

FIG. 22 is a schematic illustration of a design for a random array assay solid state cartridge implementation of an embodiment system 2200 or systems otherwise described herein. The operation is described hereinafter in reference to a bacterial input sample. However, the embodiment system 2220 can also be configured to analyze spores, viruses, and other pathogens or biomarkers. After input of the aqueous sample containing the target bacterium of interest, operation of the cartridge (i.e. method of use) is based on established laboratory scale procedures as follows:

1. BWA filtering at a filter 2261 to concentrate the target bacterium.
2. Cell lysis by lysis buffer and DNA fragmentation by enzyme, heat, or mechanical means at 2262.
3. Washing and separating DNA through the silica-gel membrane utilizing inherent silica affinity at 2264.
4. Transporting the target DNA at 2266 to the mixing and capture chamber
5. Injecting microbeads and nano-particle probes into the mixing/capture chamber at 2268 for circular flow mixing.
6. Incubation and capturing target DNA and nano-particle probes on microbeads with the aid of thermal cycling, also at 2268.
7. Washing using buffer solution 2270.
8. Flushing with an Ag enhancement solution 2272.
9. Washing again using buffer solution 2270.
10. Aligning the microbeads by fluidic focusing for SERS spectral analysis at 2274.
11. Analyzing a SERS spectrum to detect and identify biological warfare agents present.

The cartridge is non-mechanical—it incorporates only solid state microfluidic (e.g. configured for nanoliters, microliters, picoliters, femtoliters) components—and it is powered by the reader unit (not shown). A chemical lysis process has been selected over a process involving sonication, but in other embodiments, other processes such as thermal or mechanical lysing may be successfully employed.

The performance of an example commercially available mechanical cell lysing device for integration into a breadboard or microfluidic analysis system was investigated. Specifically, the efficiency of the lysing device was determined for *Bacillus subtilis* (BS) spores strain 168 (ATCC 23857) acquired from American Type Culture Collection (ATCC). The device tested was the commercially available OmniLyse® bead blender from Claremont BioSolutions (Upland, Calif.).

Cell lysing efficiency was determined by measuring the BS intact cell suspension concentration and comparing the result to the amount of DNA recovered following extraction and purification. The BS cell suspension was measured following the procedure of measuring the cell suspension turbidity using UV-Vis spectroscopy. The result was an absorbance measured at 290 nm of A290=0.255. The A290 value can be converted to concentration in g/L using Ccell=(A290/3.84 L/g)D where D is the solution dilution factor, 100 in this case. The result is 6.64 g/L. To convert this result to cells/mL, the wet density (1.223 g/cm$^3$) and volume (0.160 μm$^3$) of BS cells are used to obtain $3.4 \times 10^{10}$ cells/mL.

The amount of DNA recovered from the sample was obtained by measuring the absorbance of an aqueous solution at 260 nm to give A260=0.60. The measured absorbance value was converted to a concentration using [DNA]=A260D(50 m/mL), where D is the dilution factor (1 in this case) to give 30 μg/mL. Since the number of base pairs of BS double strand DNA (dsDNA) is known (U.S. Pat. No. 4,214,810) and the conversion factor of base pairs to molecular weight (MW) formula of MWdsDNA=4,214,810×607.4+157.9 is well established, the BS molecular weight is readily calculated to be $2.56 \times 10^9$ g/mole. The number of molecules of BS dsDNA measured was then calculated: NDNA=$(30 \times 10^{-6}$ g/mL$) \times (6.023 \times 10^{23}$/mole$)/2.56 \times 10^9$ g/mole$) = 7.06 \times 10^9$ mL$^{-1}$.

The efficiency of the DNA extraction process, which includes cell lysing, is the ratio of molecules of DNA per mL to the number of cells per mL, $7.06 \times 10^9$ mL-1/$3.4 \times 10^{10}$ mL$^{-1}$=0.21. It is also noteworthy that the lysing step was performed in only 3 minutes.

Key considerations in the assay array implementation include:

Sample Pre-Concentration.

The cartridge will include a component to concentrate organisms from liquid samples. This can be built using a set of filters with different pore sizes: the larger pore sized filters (e.g., 20 μm) can be used to filter out the large sized impurities and smaller pore sized filters (e.g., 0.22 μm) can be used to concentrate the target organisms. This step can be performed by or implemented in sample isolation modules as described herein.

Cell Lysis.

The bacteria cells are lysed by mixing with the lysis solution that is injected from its storage by the integrated solid chemical propellant pump. Alternatively, cells can be lysed by heating or mechanical blending or a combination of all. This step can be performed by or implemented in cell lysis modules as described herein.

DNA Fragmentation.

By injecting enzymes, the long ds-DNAs extracted from bacteria are fragmented into shorter pieces (such as less than 200 base pairs), which is important for the hybridization of Raman-reporter particles. This step can be performed by or implemented in cell lysis modules as described herein, or in other modules, wherein for example restriction enzymes can be added to the module for DNA fragmentation.

DNA Separation.

By filtering through a silica-gel membrane, the DNA fragments are absorbed onto the membrane in a high-salt buffer solution. After washing, the fragmented bacterial DNA will be released and collected from the membrane using a low-salt buffer solution. This step can be performed by or implemented in biological target isolation modules as described herein.

Microbead Complex Formation.

Isolated DNA fragments are hybridized to microbeads containing capture molecules and nanoparticles containing probe molecules coupled to the nanoparticles with a Raman dye. This step can be accomplished with the aid of heat, thermal cycling, mixing, bubbling, or other methods known in the art. Specific configuration of the microbead complexes and nanoparticle complexes can be realized by an end user according to the target molecule and desired analysis method. This step can be performed by or implemented in assay mixing modules as described herein, and the module can be configured according to the description herein. Movable separation walls (2267 in FIG. 22) can be incorporated into the device to aid in selective compartmentalization for microbead complex formation.

Transport and Analysis of the Microbead Complexes.

Transport of the microbead complexes (which can be a microbead coupled to a capture molecule hybridized to a target molecule, wherein the target molecule is also hybridized to a nanoparticles complex which comprises a nanoparticle coupled to a probe molecule via a dye) from an assay mixing module or the system otherwise to an analysis region where analysis can take place can be accomplished with a microfluidic channel as described herein.

Example 14—Examples of Procedures for Random Array DNA Analysis

Example 14.1: Bench Top Lysis/Assay Procedure

Lysis: Gram-Negative Bacteria (*Yersinia pestis* (VP), for example)

Collect cells (maximum $2\times10^9$ cells) in a microcentrifuge tube (Sample provided by ECBC) by centrifuging for 10 min at 5000 g (7500 rpm). Discard supernatant.

Resuspend pellet in 180 μL Buffer ATL (Qiagen DNeasy® Blood and Tissue Kit).

Add 20 μL Proteinase K (Qiagen, DNeasy®, 600 mAU/mL solution). Mix thoroughly by vortexing, and incubate at 56° C. for 1 hour (can be lysed overnight if necessary). Vortex occasionally during incubation to disperse the sample. Vortex a maximum of 15 pulses.

Add 4 μL RNase A (100 mg/ml), mix by vortexing (maximum, 15 pulses) and incubate for 2 min at room temperature.

Vortex a maximum of 15 pulses. Add 200 μL Buffer AL (Qiagen DNeasy® Blood and Tissue Kit) to the sample, and mix thoroughly by vortexing (maximum, 15 pulses).

Then add 200 μL ethanol (96-100% purity), and mix again thoroughly by vortexing (maximum, 15 pulses).

Pipet the mixture from the previous step (including any precipitate) into the silica gel column (DNeasy® Mini spin column) placed in a 2 mL collection tube. Centrifuge at 6000 g (8000 rpm) for 1 min. Discard flow-through and collection tube.

Place the silica gel spin column in a new 2 mL collection tube, add 500 μL Buffer AW1 (Qiagen DNeasy® Blood and Tissue Kit) and centrifuge for 1 min at 6000 g (8000 rpm). Discard flow-through and collection tube.

Place the silica gel spin column in a new 2 mL collection tube, add 500 μL Buffer AW2 (Qiagen DNeasy® Blood and Tissue Kit) and centrifuge for 3 min at 20,000 g (14,000 rpm) to dry the silica membrane. Discard flow-through and collection tube.

Place silica gel spin column in a clean 2 mL microcentrifuge tube and pipet 200 μL Buffer AE (Qiagen DNeasy® Blood and Tissue Kit) directly onto the silica membrane. Incubate at room temperature for 1 min, and then centrifuge for 1 min at 6000×g (8000 rpm) to elute. Collect flow-through for DNA SERS Assay.

Measure dilution of sample with UV-Vis for DNA quantification.

Lysis: Gram-Positive Bacteria (BA, or *Bacillus Anthracis* for Example)

Enzymatic lysis buffer:
20 mM Tris.Cl, pH 8.0
2 mM sodium EDTA
1.2% Triton® X-100
20 mg/mL lysozyme (Lysozyme from chicken egg white—Sigma Aldrich)

Do not add lysozyme until immediately before use.

Collect cells (maximum $2\times10^9$ cells) in a microcentrifuge tube (Sample provided by ECBC) by centrifuging for 10 min at 5000×g (7500 rpm). Discard supernatant.

Resuspend bacterial pellet in 180 μL enzymatic lysis buffer (recipe above). (Immediately before use, add lysozyme to the lysis buffer).

Incubate for at least 30 min at 37° C.

Add 25 μL Proteinase K and 200 μL Buffer AL (Qiagen DNeasy® Blood and Tissue Kit). Mix by vortexing (on maximum, 15 pulses).

Incubate at 56° C. for at least 30 min.

Add 200 μL ethanol (96-100% purity) to the sample and mix thoroughly by vortexing (maximum 15 pulses).

Pipet the mixture into the silica gel column (DNeasy® Mini spin column) placed in a 2 mL collection tube. Centrifuge at 6000×g (8000 rpm) for 1 min. Discard flow-through and collection tube.

Place the silica gel spin column in a new 2 mL collection tube, add 500 μL Buffer AW1 (Qiagen DNeasy® Blood and Tissue Kit) and centrifuge for 1 min at 6000×g (8000 rpm). Discard flow-through and collection tube.

Place the silica gel spin column in a new 2 mL collection tube, add 500 μL Buffer AW2 (Qiagen DNeasy® Blood and Tissue Kit) and centrifuge for 3 min at 20,000×g (14,000 rpm) to dry the silica membrane. Discard flow-through and collection tube.

Place the silica gel spin column in a clean 2 mL microcentrifuge tube and pipet 200 μL Buffer AE (Qiagen DNeasy® Blood and Tissue Kit) directly onto the DNeasy® membrane. Incubate at room temperature for 1 min, and then centrifuge for 1 min at 6000×g (8000 rpm) to elute. Collect flow-through for DNA SERS Assay.

Measure dilution of sample with UV-Vis for DNA quantification.

Preparation of the DNA-AuNP Probe Conjugates and Capture DNA Functionalized Glass Beads:

DNA-AuNP Probe Conjugates (for Small 4 mL Reaction):

Cleave/de-protect the Probe oligonucleotide:

Equilibrate the NAP10 column with 5 mL of 10 mM $PO_4^{3-}$ pH7.4 buffer and allow to pass through column; repeat 5-7 times.

Add 160 μL of 15.6 mM $PO_4^{3-}$ pH7.4 buffer to Probe stock (e.g. 90 μL of 100 μM stock; 9 nmole) to bring total solution volume to 250 μL and $PO_4^{3-}$ concentration to 10 mM. Add >10× molar equivalent of tris(2-carboxyethyl) phosphine (TCEP) (e.g. 2 μL of 100 mM; 200 nmole) to the Probe oligonucleotide solution. Allow reaction to proceed ~10 minutes at room temperature with occasional mixing.

Add the 250 μL of Probe oligonucleotide to the NAP10 column and allow the blue oligonucleotide solution to pass into the column. After soaking into column, add ~2 mL of 10 mM $PO_4^{3-}$ pH 7.4 buffer to the column and carefully observe the movement of the colored Probe band towards the bottom of column.

Count the clear drops eluting from the column; when the drops become blue in color, collect eluted oligonucleotide into a 1.5 mL tube until the drops become clear again.

Collect droplets #25-41; finally yield ~0.6 mL.

Mix AuNP (13±1 nm Diameter) with De-Protected Probe Oligonucleotide in Glass Vial:

Start with 0.55 mL de-protected Probe oligonucleotide (≤9 nmole) in 10 mM $PO_4^{3-}$ pH7.4 buffer (from step e above)

Add 1.118 mL of 16.1 nM AuNP (0.018 nmole). This yields AuNP:Probe to be 1:500 (mol:mol). Also add 1.218 mL of 10 mM and 13.5 μL 1 M $PO_4^{3-}$ pH7.4 buffer to bring final volume to 3 mL and buffer concentration to 10 mM.

Mix for 8 hours on orbital shaker

Add 104 μL of 1.5 M NaCl to yield 0.05 M Cl$^-$; mix for another 8 hours

Repeat step d until [Cl$^-$]=0.15 M; then add 521 μL to yield 0.3 M; mix for another 8 hours.

Centrifuge AuNP-Probes @ 13 k rpm for 20 min; discard supernatant and add 1 mL of 0.3 M Cl$^-$/10 mM $PO_4^{3-}$ pH 7.4, and mix Repeat step f two more times, but re-suspend in RNAse-free water; AuNP-Probe should be finally re-suspended in 100 μL RNAse-free water; store in refrigerator at ≥6° C.

Capture DNA-Functionalized Glass Beads

Functionalize Glass Beads with SMPB

Measure 0.35 g of glass beads

Place in 25 mL glass beaker, and add piranha solution (15 mL of $H_2SO_4$ and 5 mL of $H_2O_2$); heat on hot plate at ~130° C. for 20-30 minutes Allow to cool, pour out piranha solution and rinse 5-10 times with 18 MΩ·DI water Immerse glass beads in 5 mL of aqueous solution in polystyrene dish with1 % APS and 0.01% glacial acetic acid (by volume)

Rotate sample on an orbital shaker for 90 min at room temp

Wash the silane-treated modified glass beads 3× with DI water

Transfer glass beads to small glass beaker/vial and dry with $N_2$; then bake in oven at 130° C. for 10 min.

Promptly treat beads with 5 mL of 1 mM SMPB in 4:1 EtOH:DMSO solution in glass container.

Allow the coupling reaction to proceed for 3 h.

Rinse the beads 4× with EtOH and dry under $N_2$.

De-protect/reduce Capture oligonucleotide.

Equilibrate NAP10 column with 1×PBS and allow to elute through; repeat 5-7 times.

Thaw 190 μL aliquot of stock (100 μM) Capture oligonucleotide sequence and add 60 μL of 4.16×PBS buffer (diluted from 10× stock) to yield 250 μL of 140 mM Cl10 mM $PO_4^{3-}$. Add >10× molar equivalents of TCEP (e.g. 4 μL of 100 μM stock).

Allow to incubate at room temperature for 10-11 minutes with occasional mixing.

Add the 250 μL of Capture oligonucleotide to the NAP10 column and allow the oligonucleotide solution to pass into the column. After soaking into column, add ~2 mL of 1×PBS buffer Count the clear drops eluting from the column.

Couple the De-Protected Thiol Capture Oligonucleotide to the SMPB-Modified Glass Bead Add 2 mL of 1×PBS to each dish of dried beads For each Capture oligonucleotide, add 100, 550, and 150 μL from Tube 1, 2, and 3, respectively, to the functionalized beads Allow the reaction to proceed overnight at room temperature.

Rinse the beads 3× with 1×PBS

Example 14.2: SERS Bead DNA Assay Procedure

Hybridization Buffer=0.6 M NaCl, 0.01 M $PO_4^{3-}$, pH 7.4
$NO_3^-$ Buffer=0.6 M $NaNO_3$, 0.01 M $PO_4^{3-}$, pH 7.4
Assay (for low Target concentration)
Mix Capture Beads and Target and AuNP Probes in glass vial
1.980 mL of Hyb. Buffer
4 μL Capture Beads
21 μL of ssDNA synthetic Target
18.4 μL of AuNP probe
Incubate on shaker for 20 minutes (for heating see below)
Pipet and discard liquid
Wash
Add 3 mL of $NO_3^-$ Buffer, briefly swirl vial
Allow beads to settle, then pipet off wash liquid
Repeat steps 8a and 8b two more times
Ag development
Add 6 drops of Initiator, briefly swirl
Add 6 drops of Enhancer, briefly swirl
Incubate on shaker for 5-10 minutes
Wash
Carefully pipet off liquid, add several mL of deionized (DI) water, gently swirl
Pipet out beads and place into 1.5 mL tube, remove excess water
Add ~1 mL of DI water, gently mixing with pipet, then remove water
Repeat step 2-3 more times
Resuspend beads in DI water
Measure 20 individual beads in PDMS channel
Assay (for High Target Concentration)
Mix Capture Beads and Target in glass vial
1.980 mL of Hyb. Buffer
4 μL Capture Beads
21 μL of ssDNA synthetic Target
Incubate on shaker for 20 minutes (for heating see below)
Pipet and discard liquid
Wash
Add 3 mL of Hybridization Buffer, briefly swirl vial
Allow beads to settle, then pipet off wash liquid
Repeat steps 4a and 4b two more times
Mix Capture Beads/Target with AuNP Probes
Add 1.980 mL of Hybridization Buffer
18.4 μL of AuNP probe
Incubate on shaker for 20 minutes (for heating see below)
Pipet and discard liquid
Wash
Add 3 mL of $NO_3^-$ Buffer, briefly swirl vial
Allow beads to settle, then pipet off wash liquid
Repeat steps 8a and 8b two more times
Ag development
Add 6 drops of Initiator, briefly swirl
Add 6 drops of Enhancer, briefly swirl
Incubate on shaker for 5-10 minutes
Wash
Carefully pipet off liquid, add several mL of DI water, gently swirl
Pipet out beads and place into 1.5 mL tube, remove excess water
Add ~1 mL of DI water, gently mixing with pipette, then remove water
Repeat step 2-3 more times
Resuspend beads in DI water
Measure 20 individual beads in PDMS channel
For Heating:
Ensure water bath is up to temperature (e.g. 90° C.) before beginning assay
After adding all reagents to each vial, immerse the bottom portion of each vial in water bath and gently swirl the vial(s) for the specified heating time (e.g. 90 s)
Note: other samples that are not heated should be on shaker at room temperature while heated samples are in water bath; the total incubation time (20 min) should include the time for heating.

Example 14.3: Measuring SERS Beads

Using Peek Seeker Pro:
100 mW
10 s exposure
50× objective, Olympus microscope
Determine location of focused beam spot within video field of view
2. Each bead should be approximate size of beam spot
3. With video on (and laser off) position single isolated bead in the area where beam area; turn off light, acquire measurement; laser spot should make outline of the bead.

```
                       DNA Sequences Used

Id Name            5'->3'

BA-Target          ACA GAG GGA TTA TTG TTA AAT ATT GAT AAG GAT ATA
                   (SEQ ID No. 3)

BA-Probe-Strand    TAA CAA TAA TCC CTC TGT [Cy5] [Thiol C3]
                   (SEQ ID No. 4)

BA-Capture Strand  [Thiol C6] TAT ATC CTT ATC AAT ATT
                   (SEQ ID No. 5)

VEE-Target         TGA CAA GAC GTT CCC AAT CAT GTT GGA AGG GAA GAT
                   (SEQ ID No. 6)

VEE-Probe Strand   ATT GGG AAC GTC TTG TCA [Cy3.5] [Thiol C3]
                   (SEQ ID No. 7)

VEE-Capture Strand [Thiol C6] ATC TTC CCT TCC AAC ATG
                   (SEQ ID No. 8)

YP-Target          AGA GTA GGA TCA TAT ACC CGT TAG ATG CTG CTG GCG TTA
                   (SEQ ID No. 9)

YP-Capture Strand  [Thiol C6] TAA CGC CAG CAG CAT CTA ACG
                   (SEQ ID No. 10)

YP-Probe Strand    GGT ATA TGA TCC TAC TCT [Cy3] [Thiol C3]
                   (SEQ ID No. 11)
```

Example 15

FIG. 23, depicts an apparatus 1010 in which the systems, analysis systems, breadboard analysis systems, or other systems described herein may be coupled to in order to assist in automation of the system. The apparatus 1010 may be embodied in any one of a wide variety of wired and/or wireless computing devices, multiprocessor computing device, and so forth. As shown in FIG. 23, the apparatus 1010 comprises memory 214, a processing device 202, a number of input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the methods described herein (Labview, for example). In accordance with such embodiments, the application specific software is stored in memory 214 and executed by the processing device 202. One of ordinary skill in the art will appreciate that the memory 214 can, and typically will, comprise other components which have been omitted for purposes of brevity.

Input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, or other display device.

In the context of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 23, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices via the network interface 206 over a network. The apparatus 1010 may further comprise mass storage 226. The peripheral 211 interface supports various interfaces including, but not limited to IEEE-1394 High Performance Serial Bus (Firewire), USB, a serial connection, and a parallel connection.

Example 16

Systems as described herein for biological target analysis can be constructed from a combination of interchangeable elements or modules, as described herein. FIGS. 24A-24D demonstrate a few example schematic showing embodiments of systems that can be constructed as described herein. Fluid, such as gas or a liquid, that contains biological target molecules can flow through the modules according to the arrows presented. The examples show serial connection of modules, but multiple types of an individual module can be used, and serial connections as well as parallel connections (in some cases serial and parallel) can be utilized as well. Connections to controllers and/or computing devices are not shown in the FIGS. 24A-24D, but in some embodiments, the system (or modules therein) can have electrical and/or operational connections between pumps and/or valves within to a controller and/or computing device and be configured to receive instructions from the controller and/or computing device.

Example 17

Described herein are systems for detection of biologic targets that utilize interchangeable modules. FIGS. 25A-25F illustrate example configurations of basic, generic configurations that can be utilized to configure modules as described herein. As it's most basic, a module can have a sample chamber for sample processing as shown in FIGS. 25A-25F. A sample chamber can be any size or shape that can hold a sample in a fluid, such as a gas or liquid. A sample chamber can be a glass capillary tube, a plastic centrifuge tube (such as an Eppendorf 1.5 mL tube), Teflon tubing, and can contain a filter or a membrane, such as a 20 µm filter or a silica membrane. A sample chamber can hold biological samples to be processed, and can provide an volume where samples can be mixed with reagents in the module.

Reagents in the module can be stored in reagent vessels, chambers, or loops. Although reagent vessels are shown in FIGS. 25A-25F, a reagent vessel can also be a reagent loop, and can be a plastic container, such as a plastic bottle, or can be plastic tubing. Reagent storage vessels or loops can be in fluidic communication with a sample chamber by way of plastic tubing or Teflon tubing. Valves (one or more way valves) can direct or restrict fluid communication between a reagent storage vessel or loop and a sample chamber. Valves can be operated manually by an operator, or can be in electrical/operational connection with a controller and/or computing device for automated use. Fluid flow from a reagent vessel to a sample chamber can be driven by positive fluid pressure with the vessel or loop, or be driven by negative fluid pressure outside of a vessel or loop. Fluid pressure can be manipulated by one or more pumps, examples of which are described previously. Pumps can be operated manually or can be electrically and/or operationally coupled to a controller and/or computing device for automated use.

Figure 25A:
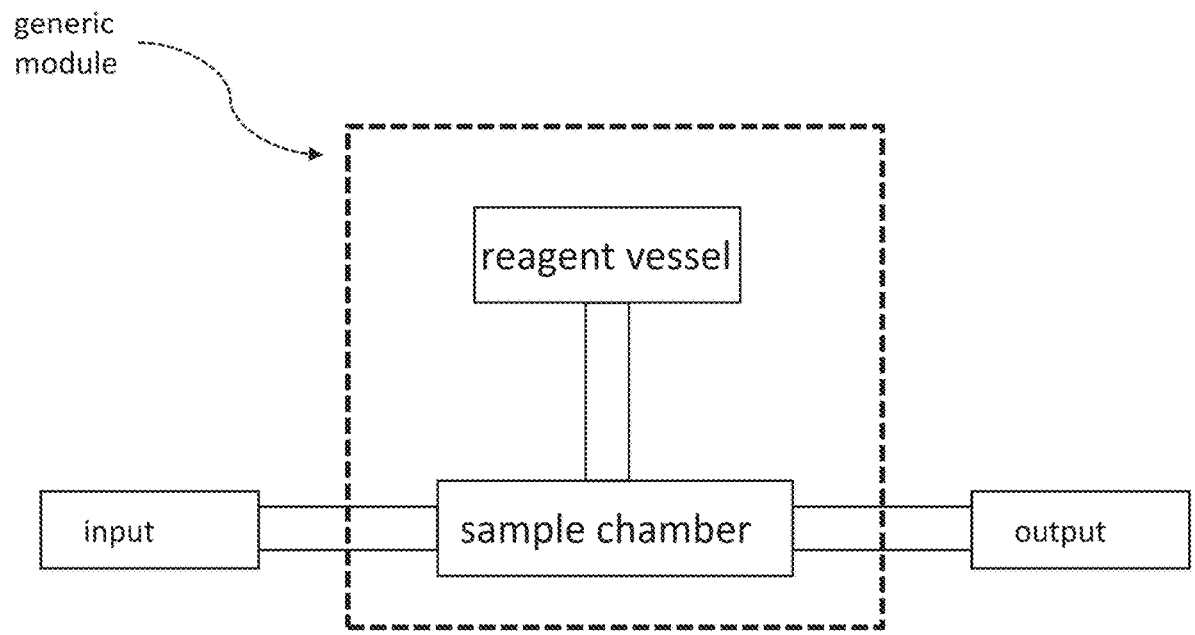
FIGS. 25A-25F are block diagrams demonstrating examples of generic configurations of modules of systems as described herein. Biological samples and/or targets can have unidirectional flow in a fluid from the input, through the sample chamber, to the output.
Figure 25B:
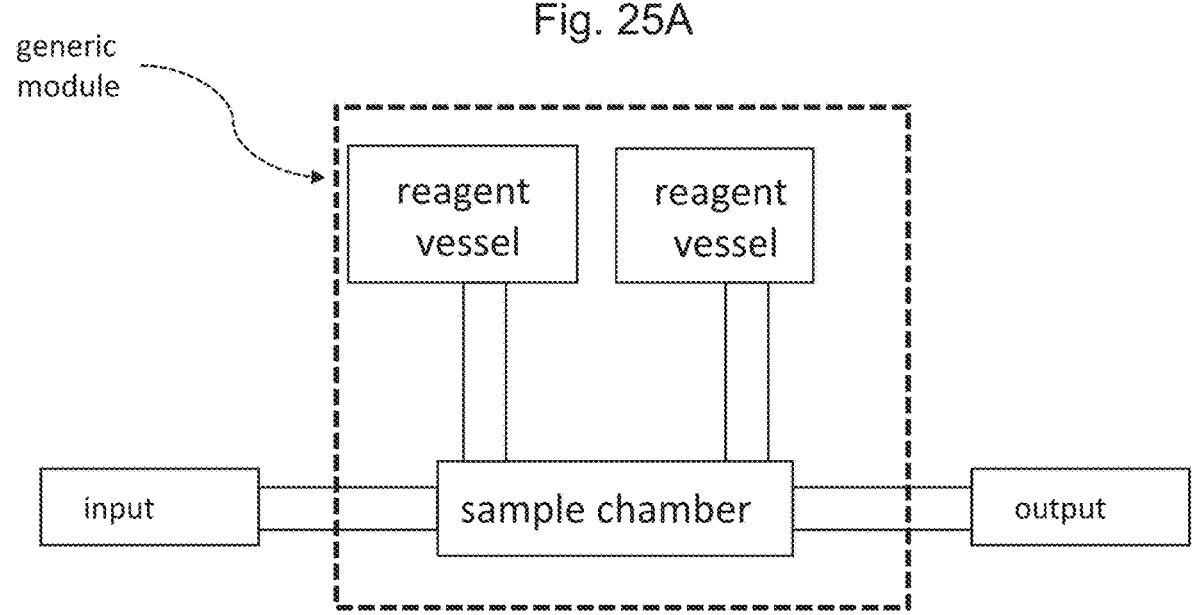
Figure 25C:
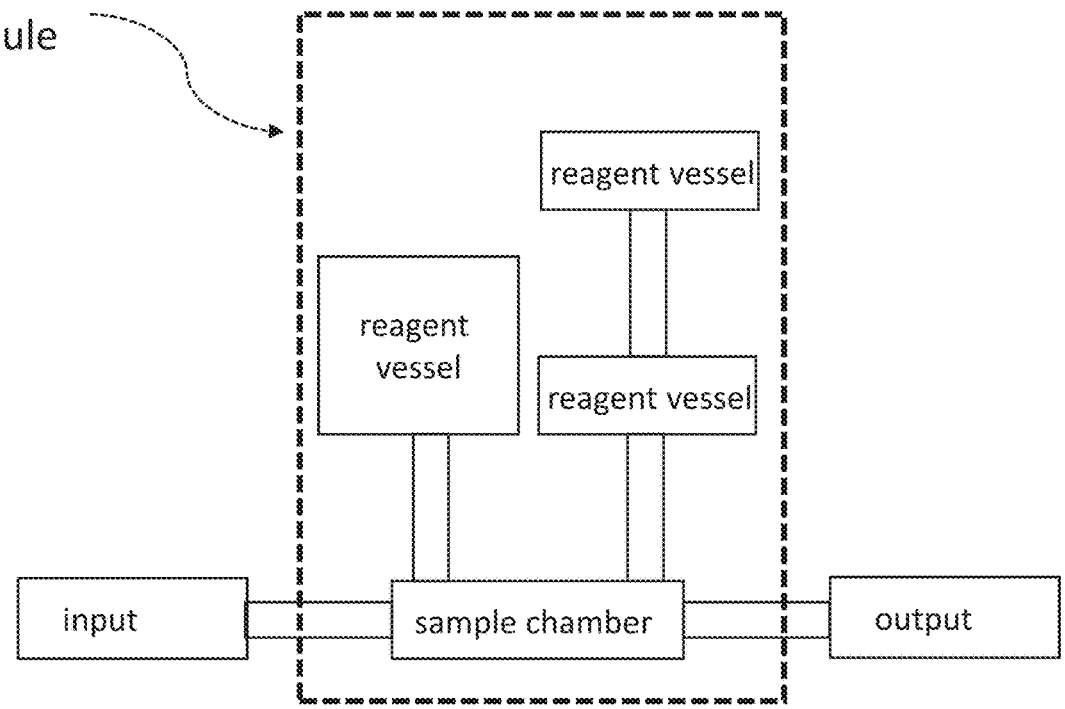

FIG. 25A shows a reagent vessel connected in series with a sample chamber (in parallel with the input/output fluid path to/from the module). Other configurations can be realized as shown in FIGS. 25B and 25C. Specific configuration of a module can be accomplished by one skilled in the art according to a desired lysis method and/or target molecule and isolation protocol.

Figure 25D:
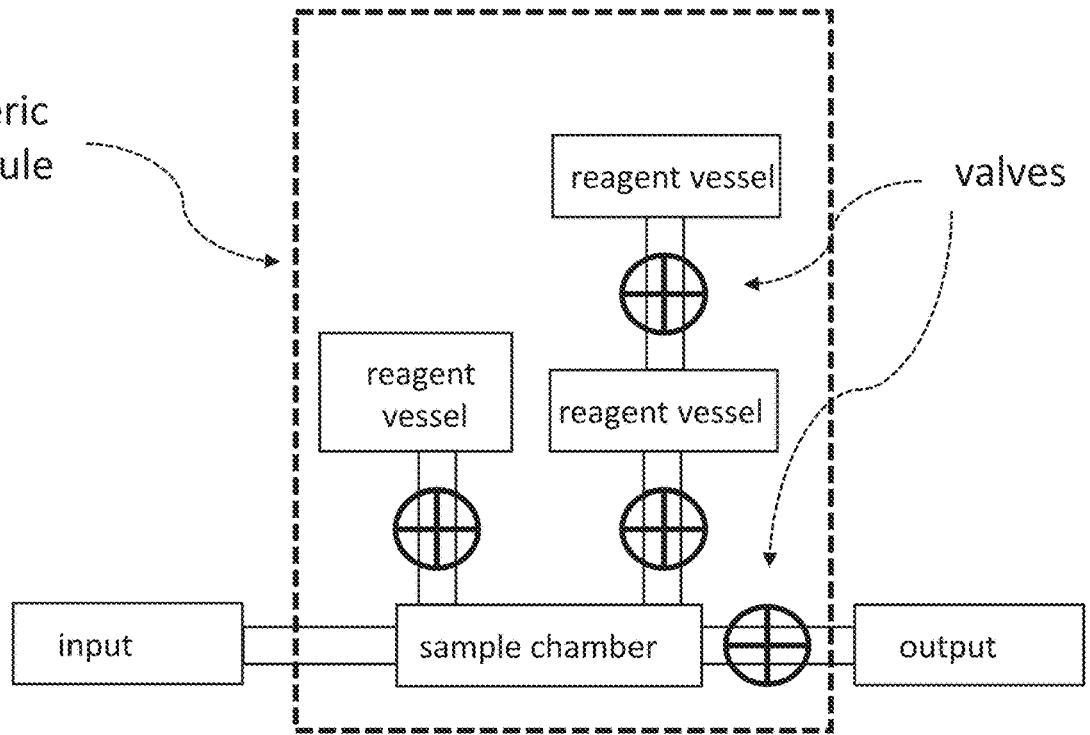
Figure 25E:
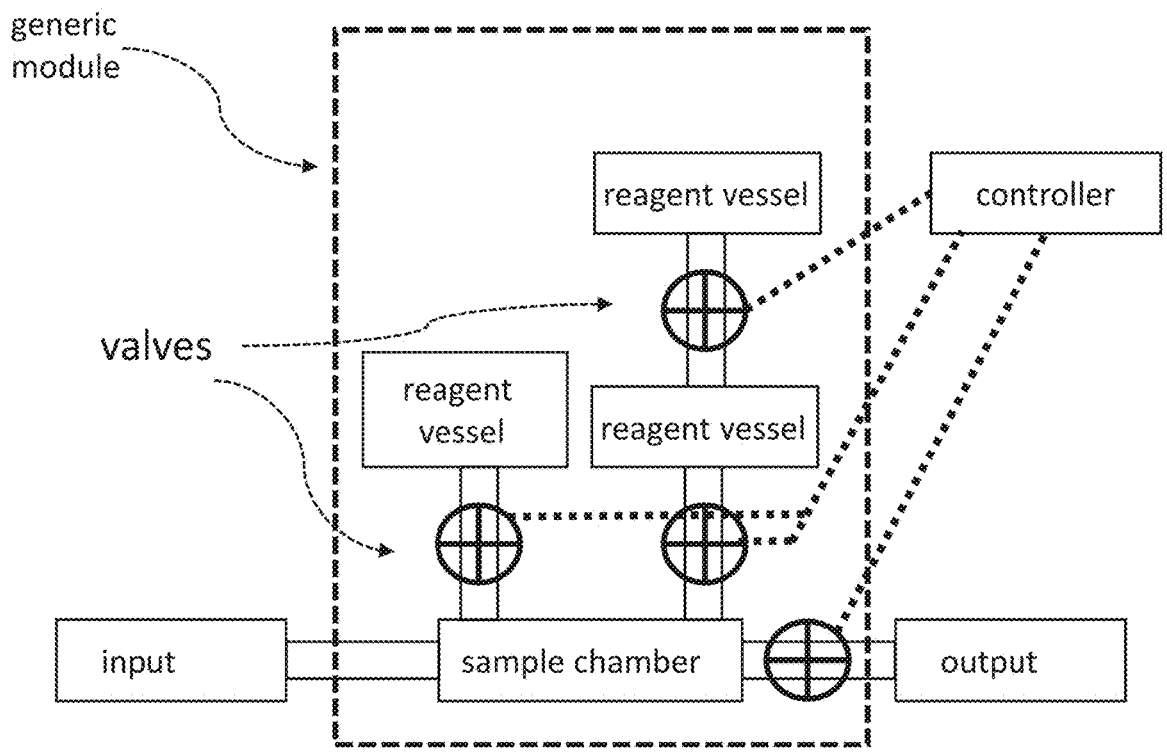
Figure 25F:
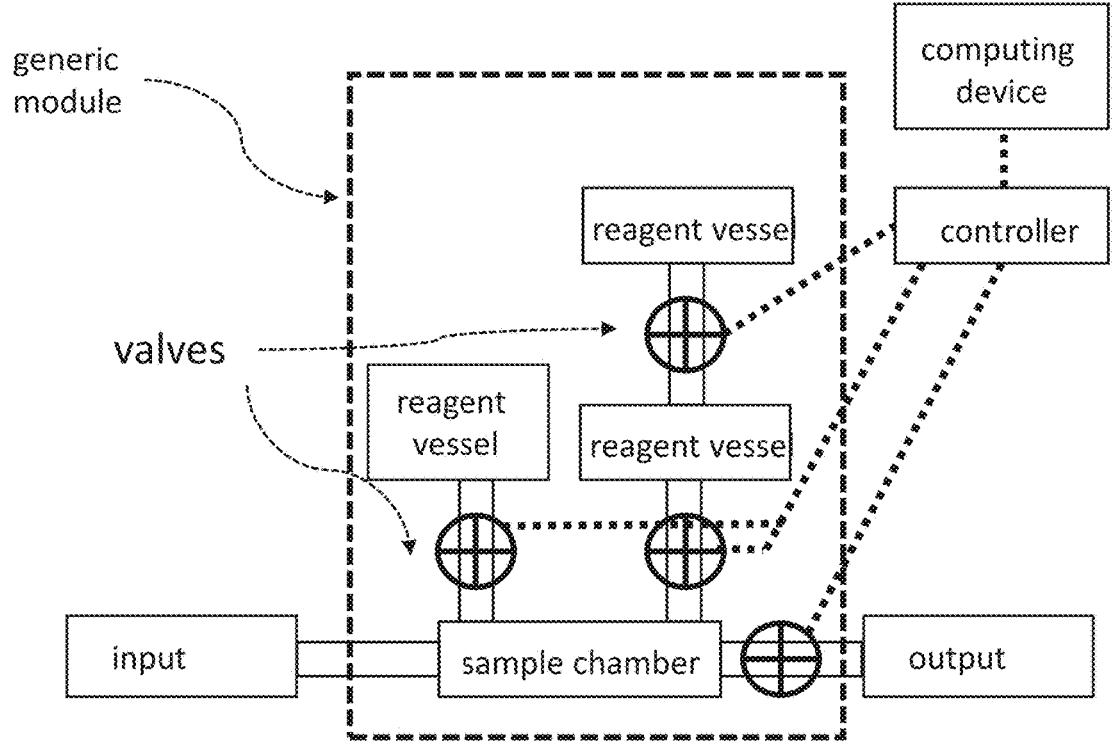

As previously mentioned, fluid control valves can be used to direct or restrict fluid between individual components within a model. FIGS. 25D-25F show example configurations of modules that employ valves, and valves connected to a controller and/or computing device.

FIG. 26 shows an embodiment of a cell lysis module in fluid connection with a biological target purification module. The embodiment of the cell lysis module is configured for thermal lysis, although other configurations can be realized. The embodiment of the biological target module is an embodiment wherein the configuration of the module is based on DNA extraction with a Qiagen DNeasy® kit and Qiagen DNeasy® extraction protocol. Other configurations can be realized according to the specific target molecule of interest and isolation methodology/protocol for that target. The module embodiment in FIG. 26 also employs optional optical sensors which can be used for manual or automated monitoring of the module during use i.e. procession of target purification. Optional electrical/operational connections to a controller are also shown for automated use, although these can be omitted for a manually operated module in areas where electrical power may not be readily available.

Figure 27:
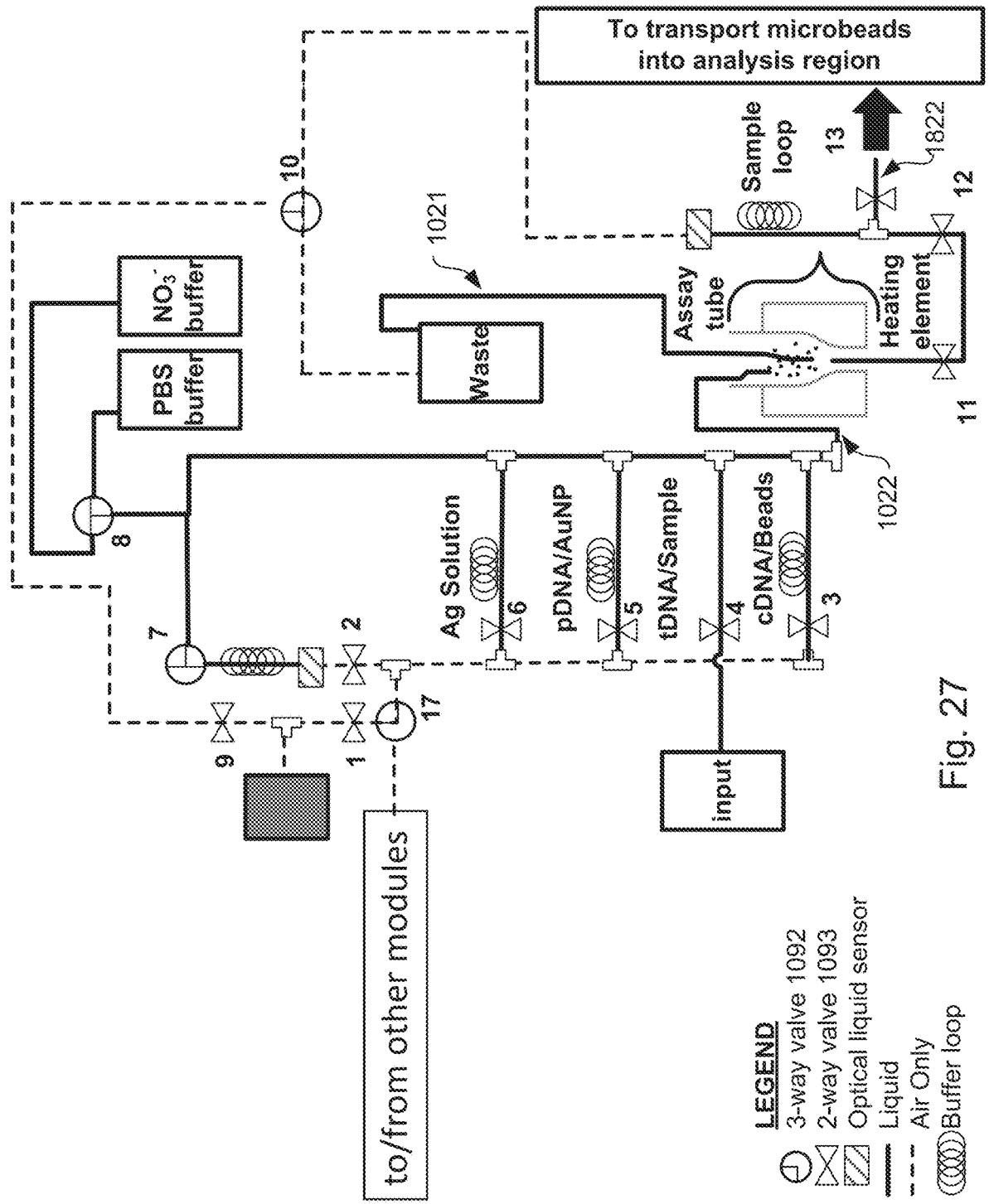
FIG. 27 is an embodiment of an assay mixing module configured for SERS detection of DNA target molecules.

FIG. 27 shows an embodiment of an assay mixing module according to the present disclosure. The configuration of the module utilizes reagent loops, and the module is configured for hybridization of biological target DNA to microbeads containing capture DNA and nanoparticles coupled to probe DNA through a spectroscopic label configured for SERS detection. The embodiment of FIG. 27 incorporates a thermal cycling heating element for efficient DNA hybridization, and can incorporate an element that injects gas into the assay tube to create bubbling, which can be beneficial for the mixing of reagents in the assay tube. Other configurations of this module can be realized according to the present disclosure by one skilled in the art according to a desired target molecule and detection or analysis procedure. Example 14 shows examples of assays the assay mixing module or other modules of a system could be configured to carry out.

Although now shown in FIGS. 25A-25F, pumps can be used to drive fluids within a module or between modules in the system. One or more pumps can be in fluid connection with a module via the input or output shown in FIGS. 25A-25F, and can create negative or positive pressure. Pumps can also be in fluid connection with or integrated into reagent vessels to drive reagent movement throughout a module. Examples of pumps that can be used can be syringe pumps, syringes, di-electrophoresis pumps, and solid propellant pumps, although other pumps known in the art can also be used. Pumps can be manually operated or can be operationally coupled to a controller and/or computing device via standard electronic connections for automated use.

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

Embodiments of the present disclosure will employ, unless otherwise indicated, techniques of separating, testing, and constructing materials, which are within the skill of the art. Such techniques are explained fully in the literature.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

At least the following is claimed:

1. A method of detecting a biological target, comprising:
providing one or more biological samples;
providing a fluid manipulation system comprising:
- a sample isolation module containing one or more filters with micro-scale pores configured to isolate one or more biological samples of a desired size,
  - wherein the sample isolation module is in fluidic communication with a sample lysis module,
  - wherein the sample isolation module is configured to receive samples containing the one or more biological samples from outside of the system and configured to send the one or more biological samples of a desired size to a sample lysis module;
- a sample lysis module configured to receive the one or more isolated biological samples,
  - wherein the sample lysis module is configured for thermal or enzymatic lysis to lyse cells and create products of cell lysis, the products of cell lysis comprising biological targets,
  - wherein the sample lysis module is configured to send biological targets to a biological target purification module;
- a biological target purification module configured to receive the products of cell lysis and isolate one or more biological targets with one or more silica membranes or capillaries,
  - wherein the biological target purification module comprises one or more reagent vessels,
  - wherein the biological target purification module is in fluidic communication with an assay mixing module and configured to send the one or more isolated biological targets to the assay mixing module;
- the assay mixing module comprising a plurality of microbead complex components for generating one or more non-stationary microbead complexes contained in one or more reagents,
  - wherein the assay mixing module is configured to mechanically and thermally mix the one or more isolated biological targets with the plurality of microbead complex components;
- a flow path in fluidic communication with the assay mixing module and configured to receive the one or more non-stationary microbead complexes;
- an analysis region comprising a microfluidic glass channel or microfluidic capillary configured to analyze the one or more non-stationary microbead complexes with a spectrometer;

introducing the one or more biological samples comprising biological targets into the sample isolation module;
isolating one or more biological targets from the one or more biological samples with the biological target purification module;
forming one or more non-stationary microbead complexes from the one or more isolated biological targets and the plurality of microbead complex components in a volume of fluid in the assay mixing module; and
detecting the one or more non-stationary microbead complexes in the volume of fluid in the analysis region.

2. The method of claim 1, wherein the plurality of microbead complex components comprise:
one or more microbeads with one or more capture molecules coupled thereto; and
one or more nanoparticles with one or more probe molecules coupled thereto by way of a label,
wherein the capture molecules and the probe molecule are configured to bind to the one or more isolated biological targets.

3. The method of claim 2, wherein the label is configured to provide a Raman spectrum to a portable Raman spectrometer.

4. The method of claim 1, wherein the volume of fluid is a femtoliter volume, a picoliter volume, a nanoliter volume, or microliter volume.

5. The method of claim 1, further comprising:
lysing cells in the one or more biological samples with the sample lysis module.

6. The method of claim 5, wherein isolating the one or more biological targets comprises isolating the one or more biological targets from the lysed cells.

7. The method of claim 1, wherein detecting the one or more non-stationary microbead complexes comprises analyzing the one or more non-stationary microbead complexes with a spectrometer.

* * * * *